US008748369B2

(12) United States Patent
Epperly et al.

(10) Patent No.: US 8,748,369 B2
(45) Date of Patent: Jun. 10, 2014

(54) USE OF TARGETED NITROXIDE AGENTS IN BONE HEALING

(75) Inventors: Michael W. Epperly, Pittsburgh, PA (US); Abhay Sudhir Gokhale, Galena, OH (US); Joel S. Greenberger, Sawickley, PA (US); Peter Wipf, Pittsburgh, PA (US); Julianne Glowacki, Jamaica Plain, MA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/320,999

(22) PCT Filed: Jun. 4, 2010

(86) PCT No.: PCT/US2010/037414
§ 371 (c)(1),
(2), (4) Date: Apr. 30, 2012

(87) PCT Pub. No.: WO2010/141824
PCT Pub. Date: Dec. 9, 2010

(65) Prior Publication Data
US 2012/0252733 A1    Oct. 4, 2012

Related U.S. Application Data

(60) Provisional application No. 61/184,497, filed on Jun. 5, 2009.

(51) Int. Cl.
*A61K 38/00* (2006.01)
*A61K 31/13* (2006.01)
*A01N 33/24* (2006.01)

(52) U.S. Cl.
USPC ............................................ 514/1.1; 514/645

(58) Field of Classification Search
CPC .................................................. A61K 31/00
See application file for complete search history.

(56) References Cited

U.S. PATENT DOCUMENTS

| | | | |
|---|---|---|---|
| 6,331,532 | B1 | 12/2001 | Murphy et al. |
| 6,939,880 | B2 | 9/2005 | Hansen et al. |
| 7,528,174 | B2* | 5/2009 | Wipf et al. ............ 514/645 |
| 7,718,603 | B1 | 5/2010 | Wipf et al. |
| 8,288,551 | B2* | 10/2012 | Wipf et al. ............ 546/242 |
| 2005/0020633 | A1 | 1/2005 | Maxwell et al. |
| 2007/0161544 | A1 | 7/2007 | Wipf et al. |
| 2007/0161573 | A1* | 7/2007 | Wipf et al. ............ 514/17 |
| 2008/0045470 | A1 | 2/2008 | Bielawska et al. |
| 2008/0161267 | A1 | 7/2008 | Taylor et al. |
| 2011/0039792 | A1 | 2/2011 | Wipf et al. |
| 2011/0172214 | A1 | 7/2011 | Wipf et al. |
| 2012/0004263 | A1 | 1/2012 | Niedernhofer et al. |
| 2012/0207687 | A1 | 8/2012 | Falo, Jr. et al. |

FOREIGN PATENT DOCUMENTS

| | | |
|---|---|---|
| WO | WO 2010/009389 | 1/2010 |
| WO | WO 2012/068081 | 5/2012 |
| WO | WO 2012/112851 | 8/2012 |

OTHER PUBLICATIONS

Hahn et al., Cancer Res., 1992, 52, 1750-1753.*
Fink et al., "Hemigramicidin-TEMPO conjugates: Novel mitochondria-targeted anti-oxidants," *Biochemical Pharmacology* 74(6):801-809, Sep. 15, 2007.
Hahn et al., "Tempol, a Stable Free Radical, Is a Novel Murine Radiation Protector," *Cancer Research* 52:1750-1753, 1992.
Hahn et al., "Potential Use of Nitroxides in Radiation Oncology," *Cancer Research* 54:2006s-2010s, 1994.
Jiang et al., "Structural Requirements for Optimized Delivery, Inhibition of Oxidative Stress, and Antiapoptotic Activity of Targeted Nitroxides," *The Journal of Pharmacology and Experimental Therapeutics* 320(3):1050-1060, Mar. 1, 2007.
Krishna et al., "Do Nitroxide Antioxidants Act as Scavengers of $O_2$ or as SOD Mimics?" *The Journal of Biological Chemistry* 271(42):26026-26031, 1996.
Macias et al., "Treatment with a Novel Hemigramicidin-TEMPO Conjugate Prolongs Survival in a Rat Model of Lethal Hemorrhagic Shock," *Annals of Surgery* 245(2):305-314, Feb. 1, 2007.
Mitchell et al., "Radiation, Radicals, and Images," *Annals New York Academy of Sciences* 899:28-43, 2000.
Wipf et al., "Convergent Approach to (E)-Alkene and Cyclopropane Peptide Isosteres," *Organic Letters* 7(1):103-106, 2005.
Wipf et al., "Mitochondrial Targeting of Selective Electron Scavengers: Synthesis and Biological Analysis of Hemigramicidin—TEMPO Conjugates," *JACS* 127(36):12460-12461, Sep. 1, 2005 (Published online Aug. 15, 2005).
European Supplemental Search Report from corresponding European Application No. 09798808.3 dated Feb. 22, 2012.
International Search Report from PCT Application No. PCT/US2009/051004, mailed Mar. 12, 2010.
Written Opinion of the International Search Authority from PCT Application No. PCT/US2009/051004, mailed Mar. 12, 2010.
International Preliminary Report on Patentability from PCT Application No. PCT/US2009/051004, dated Jan. 18, 2011.
International Preliminary Report on Patentability from PCT Application No. PCT/US2009/050983, dated Jan. 18, 2011.
International Search Report from PCT Application No. PCT/US2010/037414 dated Feb. 24, 2011.
Non-Final Office Action from corresponding U.S. Appl. No. 12/930,702 dated Feb. 1, 2013.
Non-Final Office Action from corresponding U.S. Appl. No. 13/006,640 dated Jan. 25, 2013.

* cited by examiner

*Primary Examiner* — Marcela M Cordero Garcia
*Assistant Examiner* — Kaipeen Yang
(74) *Attorney, Agent, or Firm* — Klarquist Sparkman LLP

(57) ABSTRACT

Provided herein are compositions and related methods useful for accelerating bone healing and growth. The compounds comprise a nitroxide-containing group attached to a mitochondria-targeting group. The compounds can be cross-linked into dimers without loss of activity.

30 Claims, 29 Drawing Sheets

Nitronyl nitroxide, LogP=1.7  Doxyl radical, LogP=2.6  3-carboxyl-PROXYL, LogP=1.4  TEMPO choline, LogP=2.5

3-Carbamoyl-PROXYL, LogP=0.9  4-Maleimido-TEMPO, LogP=2.9  4-(2-Bromoacetamido)-TEMPO, LogP=1.9

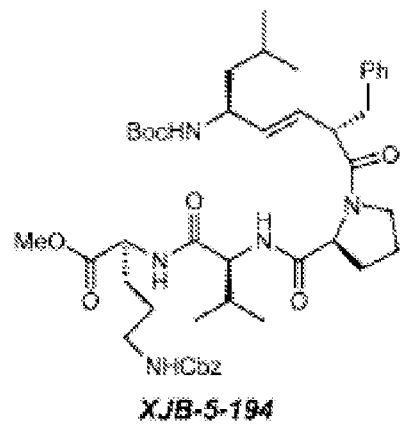
XJB-5-194
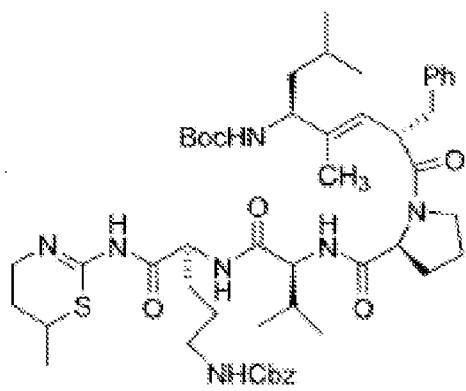
XJB-5-241
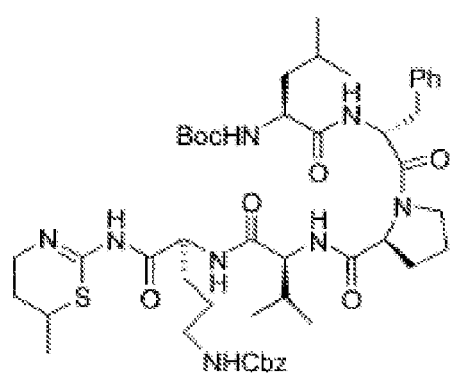
XJB-5-127
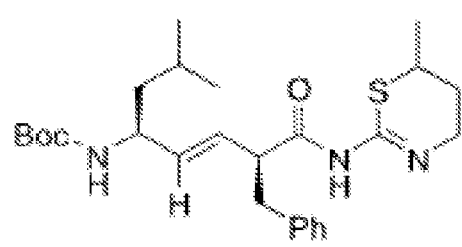
XJB-5-234
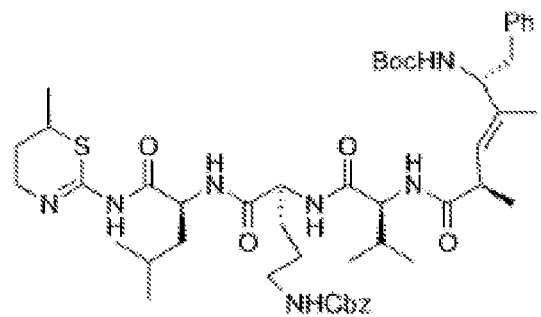
XJB-7-42
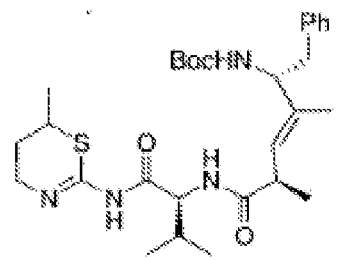
XJB-7-43
*Fig. 2-3*

1

2

3

4

USE OF TARGETED NITROXIDE AGENTS IN BONE HEALING

CROSS REFERENCE TO RELATED APPLICATIONS

This application is a National Stage of International patent application Ser. No. PCT/US2010/037414, filed Jun. 4, 2010, which claims the benefit of United States Provisional patent application Ser. No. 61/184,497, filed Jun. 5, 2009, which is herein incorporated by reference in its entirety.

Provided herein are methods of treating, healing or repairing bone injury, damage, deficiencies or bone defects in a subject caused by injury, pathology, defects etc. The methods include administration to the subject of an amount of a compound effective to treat or heal bone injury or pathology in the patient. The compounds comprise a mitochondria-targeting group attached to a nitroxide-containing group. These functions may also be used in dimerized form by attachment to a suitable bifunctional linker.

Currently, no drugs are known to speed up (accelerate) the healing of bone damage. Compounds described herein can protect or mitigate mice from whole body irradiation. We now find that administration of compounds described herein speeds up the healing time of the bones. No other compounds are known to do this.

The compounds described herein are among a group of mitochondria-targeting antioxidants, such as described in United States Patent Publication Nos. 20070161573 and 20070161544. In one embodiment, the compositions comprise membrane active peptidyl fragments having a high affinity with the mitochondria linked to cargo. The cargo may be selected from a large group of candidates. As shown below, the cargo is a nitroxide-containing antioxidant group, such as, without limitation, TEMPO, TEMPOL, TMIO and 1-Me-AZADO.

STATEMENT REGARDING FEDERAL FUNDING

This invention was made with government support under Grant No. NIAID U19 AI068021, awarded by the National Institutes of Health, and contract HHS010200800062C awarded by BARDA. The government has certain rights in the invention.

SUMMARY

Provided herein are compounds comprising a targeting group and a cargo that is a nitroxide-containing group and compositions comprising the compounds which are useful in accelerating bone healing due to any cause, including bone injury, pathology or degenerative condition, such as osteoporosis. Methods of repairing bone and increasing bone density also are provided, for example in subjects that have not been irradiated. As illustrated in the Examples, below, compounds and compositions described herein have use in acceleration of bone growth or repair and in increasing bone density.

BRIEF DESCRIPTION OF THE DRAWINGS

FIG. 5A shows an FD4 read-out of TEMPOL which is used as a "positive control" for the gut mucosal protection assay. FIG. 5B shows an FD4 read-out of TEMPO conjugate XJB-5-208 reflecting gut mucosal protection. FIG. 5C shows an FD4 read-out of XJB-5-125 which has the TEMPO payload, but fails to provide protection against gut barrier dysfunction induced by hemorrhage. FIG. 5D shows an FD4 read-out of XJB-5-127 which lacks the TEMPO payload and fails to provide protection against gut barrier dysfunction induced by hemorrhage. FIG. 5E shows an FD4 read-out of TEMPO conjugate XJB-5-131 reflecting gut mucosal protection. FIG. 5F shows an FD4 read-out of XJB-5-133 which lacks the TEMPO payload even though it possesses the same hemigramicidin mitochondria targeting moiety as the most active compound, XJB-5-131.

FIG. 5G shows an FD4 read-out of XJB-5-197 which has the TEMPO payload, but fails to provide protection against gut barrier dysfunction induced by hemorrhage. FIG. 5H shows an FD4 read-out of XJB-5-194 which lacks the TEMPO payload and fails to provide protection against gut barrier dysfunction induced by hemorrhage.

FIG. 6A is a graphical representation of superoxide production based upon mean fluorescence intensity from 10,000 ileal cells. FIG. 6B is a graphical representation of phosphatidylserine (PS) externalization as indicated by the percentage of annexin V-positive cells. FIG. 6C is a graphical representation of caspase-3 activity as indicated by amount of its specific substrate present, Z-DVED-AMC, in nmol/mg protein. FIG. 6D is a graphical representation of DNA fragmentation as indicated by propidium iodide fluorescence. FIG. 6E is a graphical representation of PS externalization at different concentrations of the compound 5a. FIG. 6F is a graphical representation of adenosine triphosphate (ATP) levels in mitochondria in the presence or absence of 5a or 2-deoxyglucose.

FIG. 7 illustrates the effects of intraluminal XJB-5-131 on hemorrhage-induced peroxidation of phospholipids in intestinal mucosa.

DETAILED DESCRIPTION

Figure 1:
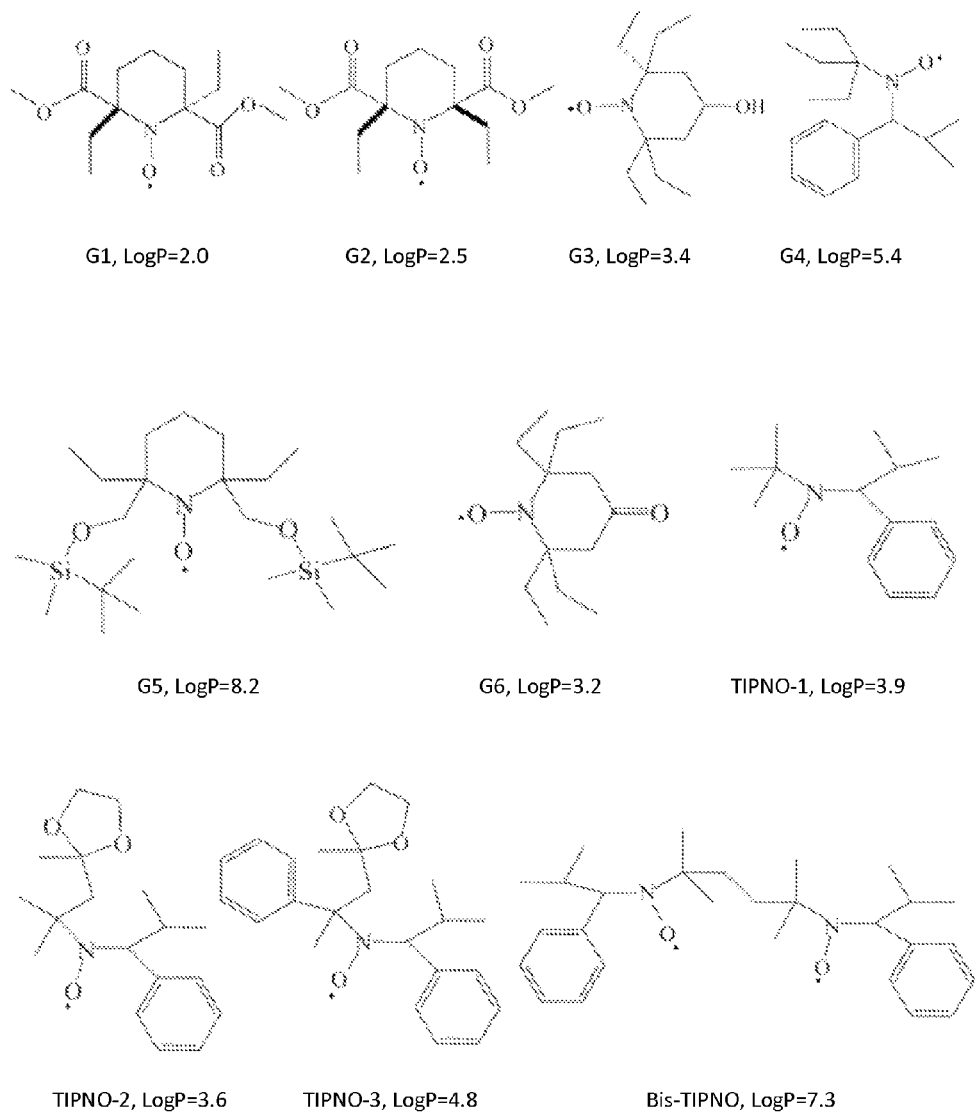
FIG. 1 provides non-limiting examples of certain nitroxides. The logP values were estimated using the online calculator of molecular properties and drug likeness on the Molinspirations Web site (www.molinspiration.com/cgi-bin/properties). TIPNO=tert-butyl isopropyl phenyl nitroxide.
Figure 1:
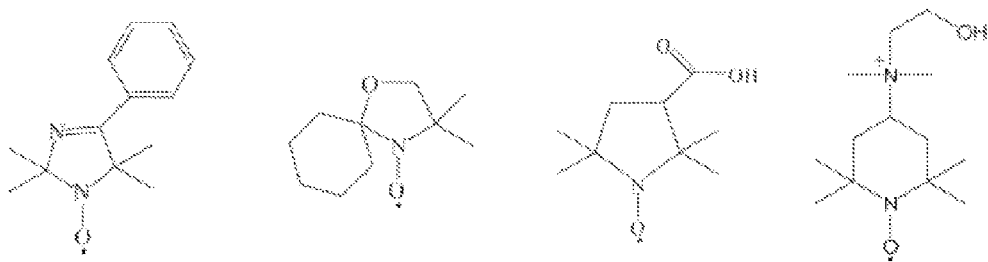

As used herein, the term "subject" refers to members of the animal kingdom including but not limited to human beings. The term "reactive oxygen species" ("ROS") includes, but is not limited to, superoxide anion, hydroxyl, and hydroperoxide radicals.

An antioxidant compound is defined herein as a compound that decreases the rate of oxidation of other compounds or prevents a substance from reacting with oxygen or oxygen containing compounds. A compound may be determined to be an antioxidant compound by assessing its ability to decrease molecular oxidation and/or cellular sequellae of oxidative stress, for example, and without limitation, the ability to decrease lipid peroxidation and/or decrease oxidative damage to protein or nucleic acid. In one embodiment, an antioxidant has a level of antioxidant activity between 0.01 and 1000 times the antioxidant activity of ascorbic acid in at least one assay that measures antioxidant activity.

Provided herein are compounds and compositions comprising a targeting group and a nitroxide-containing group. The cargo may be any useful compound, such as an antioxidant, as are well known in the medical and chemical arts. The cargo may comprise a factor having anti-microbial activity. For example, the targeting groups may be cross-linked to antibacterial enzymes, such as lysozyme, or antibiotics, such as penicillin. Other methods for attaching the targeting groups to a cargo are well known in the art. In one embodiment, the cargo is an antioxidant, such as a nitroxide-containing group. In another embodiment, the cargo transported by mitochondria-selective targeting agents may include an inhibitor of NOS activity. The cargo may have a property selected from the group consisting of antioxidant, radioprotective, protective, anti-apoptotic, therapeutic, ameliorative, NOS antagonist and combinations thereof, though in the context of the present disclosure, is capable of increasing or accelerating a rate of bone growth or repair, or increasing bone density in a therapeutic context when administered to a subject with the object of increasing or accelerating bone growth or repair rates or increasing bone density. It may be desirable to increase bone growth, repair rates or bone density in a subject for any number of reasons. Repair of trauma to the bone, such as breakage or removal of bone, whether accidental or as part of a surgical procedure, requires bone repair, and would benefit from a treatment that would accelerate bone repair rates. Accelerating bone repair rates also would be desirable in the context of disease states or pathologies in which bone degeneration is present, or bone repair is decreased, such as in diabetic patients or in patients suffering from osteoporosis. In another embodiment, the cargo may have the ability to inhibit nitric oxide synthase enzyme activity. It will be appreciated that a wide variety of cargos may be employed in the composition described herein. Non-limiting examples of cargos include: a 2-amino-6-methyl-thiazine, a ubiquinone analog, a ubiquinone analog fragment moiety, a ubiquinone analog fragment moiety lacking a hydrophilic tail, a superoxide dismutase mimetic, a superoxide dismutase biomimetic and a salen-manganese compound.

In one non-limiting embodiment, the compound has the structure:

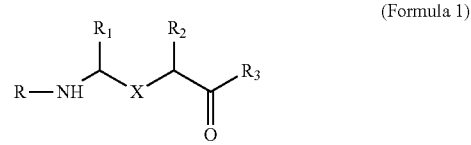

(Formula 1)

wherein X is one of

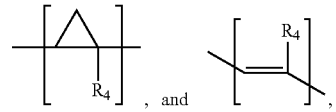

and $R_1$ and $R_2$ are, independently, $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl. $R_4$ is H or $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl. $R_3$ is —NH—$R_5$, —O—$R_5$ or —$CH_2$—$R_5$, where $R_5$ is an —N—O., —N—OH or N=O containing group. R is —C(O)—$R_6$ or —C(O)O—$R_6$, and $R_6$ is $C_1$-$C_6$ straight or branched-chain alkyl optionally comprising one or more phenyl (—$C_6H_5$) groups, and that optionally are methyl-, ethyl-, hydroxyl- or fluoro-substituted, including Boc (R=—C(O)O-tert-butyl) and Cbz (R=—C(O)O-benzyl (Bn)) groups. Excluded from this is the enantiomer XJB-5-208. R also may be a diphenylphosphate group, that is, R=

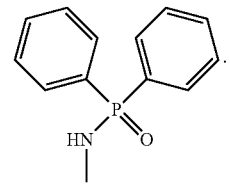 [SMILES: CNP(=O)(c1ccccc1)c1ccccc1]

In one embodiment, $R_3$ is

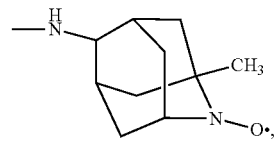

(1-Me-AZADO or 1-methyl azaadamantine N-oxyl).

In another embodiment $R_3$ is

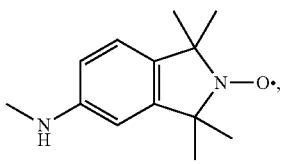

(TMIO; 1,1,3,3-trimethylisoidolin-2-yloxyl).

As used herein, unless indicated otherwise, for instance in a structure, all compounds and/or structures described herein comprise all possible stereoisomers, individually or mixtures thereof.

As indicated above, $R_5$ can be an —N—O•, —N—OH or —N═O containing group (not —N—O•, —N—OH or —N═O, but groups containing those moieties, such as TEMPO, etc, as described herein). As is known to one ordinarily skilled in the art, nitroxide and nitroxide derivatives, including TEMPOL and associated TEMPO derivatives are stable radicals that can withstand biological environments. Therefore, the presence of the 4-amino-TEMPO, TEMPOL or another nitroxide "payload" within the mitochondria membrane can serve as an effective and efficient electron scavenger of the ROS being produced within the membrane. Non-limiting examples of this include TEMPO (2,2,6,6-Tetramethyl-4-piperidine 1-oxyl) and TEMPOL (4-Hydroxy-TEMPO), in which, when incorporated into the compound described herein, form, for example, when $R_3$ is —NH—$R_5$, —O—$R_5$:

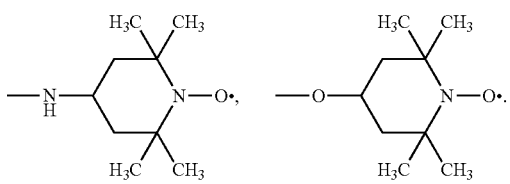

Additional non-limiting examples of —N—O•, —N—OH or N═O containing group are provided in Table 1 and in FIG. 1 (from Jiang, J., et al. "Structural Requirements for Optimized Delivery, Inhibition of Oxidative Stress, and Antiapoptotic Activity of Targeted Nitroxides", *The Journal Of Pharmacology and Experimental Therapeutics* (2007) 320(3):1050-60). A person of ordinary skill in the art would be able to conjugate (covalently attach) any of these compounds to the rest of the compound using common linkers and/or conjugation chemistries, such as the chemistries described herein. The following are non-limiting excerpts from a list of over 300 identified commercially-available —N—O•, —N—OH or N═O containing compounds that may be useful in preparation of the compounds or compositions described herein: trimethylamine N-oxide; N,N-dimethyldodecylamine N-oxide; N-benzoyl-N-phenylhydroxylamine; N,N-diethylhydroxylamine; N,N-dibenzylhydroxylamine; di-tert-butyl nitroxide; N,N-dimethylhydroxylamine hydrochloride; metobromuron; benzyl-di-beta-hydroxy ethylamine-N-oxide; bis(trifluoromethyl)nitroxide; triethylamine N-oxide; N-methoxy-N-methylcarbamate; N,N-bis(2-chloro-6-fluorobenzyl)-n-[(([2,2-dichloro-1-(1,4-thiazinan-4-yl)ethylidene]amino) carbonyl]amine]; tri-N-octylamine N-oxide; diethyl (N-methoxy-N-methylcarbamoylmethyl)phosphonate; N-methoxy-N-methyl-2-(triphenylphosphoranylidene)acetamide; N-methoxy-N-methyl-N'-[5-oxo-2-(trifluoromethyl)-5H-chromeno[2,3-B]pyridin-3-yl]urea; N-[(4-chlorobenzyl)oxy]-N-([5-oxo-2-phenyl-1,3-oxazol-4(5H)-yliden]methyl)acetamide; N-methylfurohydroxamic acid; N,N-dimethylnonylamine N-oxide; N-(tert-butoxycarbonyl)-L-alanine N'-methoxy-N'-methylamide; 1-(4-bromophenyl)-3-(methyl([3-(trifluoromethyl)benzoyl]oxy) amino)-2-Propen-1-one; 2-([[(anilinocarbonyl)oxy](methyl) amino]methylene)-5-(4-chlorophenyl)-1,3-cyclohexanedione; N-methoxy-N-methyl-2-(trifluoromethyl)-1,8-naphthyridine-3-carboxamide; N-methoxy-N-methyl-indole-6-carboxamide; desferrioxamin; AKOS 91254; N-[(3s,4r)-6-cyano-3,4-dihydro-3-hydroxy-2,2-dimethyl-2H-1-benzopyran-4-yl]-N-hydroxyacetamide; N-methoxy-N-methyl-1,2-dihydro-4-oxo-pyrrolo [3,2,1-ij]quinoline-5-carboxamide; FR-900098; 2,2'-(hydroxyimino)bis-ethanesulfonic acid disodium salt; Fmoc-N-ethyl-hydroxylamine; bis(N,N-dimethylhydroxamido) hydroxooxovanadate; pyraclostrobin; 1-Boc-5-chloro-3-(methoxy-methyl-carbamoyl)indazole; N-methoxy-N-methyl-thiazole-2-carboxamide; 4,4-difluoro-N-methyl-N-methoxy-L-prolinamide HCl; 3-fluoro-4-(methoxy(methyl) carbamoyl)phenylboronic acid; 1-isopropyl-N-methoxy-N-methyl-1H-benzo[D][1,2,3]triazole-6-carboxamide; (trans)-2-(4-chlorophenyl)-N-methoxy-N-methylcyclopropanecarboxamide; bicyclo[2.2.1]heptane-2-carboxylic acid methoxy-methyl-amide; AKOS Bc-0582; 3-(N,o-dimethylhydroxylaminocarbonyl)phenylboronic acid, pinacol ester; and 1-triisopropylsilanyl-1H-pyrrolo[2,3-B]pyridine-5-carboxylic acid methoxy-methyl-amide.

According to one embodiment, the compound has the structure

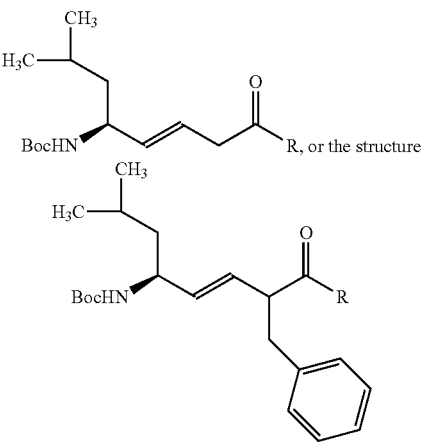

wherein R is —NH—$R_1$, —O—$R_1$ or —CH$_2$—$R_1$, and $R_1$ is an —N—O•, —N—OH or N═O containing group. In one embodiment, R is —NH—$R_1$, and in another R is —NH-TEMPO.

According to another embodiment, the compound has the structure:

(Formula 2)

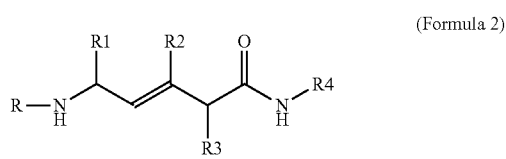

in which R1, R2 and R3 are, independently, $C_1$-$C_6$ straight or branched-chain alkyl, optionally including a phenyl ($C_6H_5$) group, that optionally is methyl-, hydroxyl- or fluoro-substituted, including 2-methyl propyl, benzyl, methyl-, hydroxyl- or fluoro-substituted benzyl, such as 4-hydroxybenzyl, and R2 may be H. R4 is an —N—O., —N—OH or N=O containing group. R is —C(O)—R5, —C(O)O—R5, or diphenyl phosphate, and R5 is $C_1$-$C_6$ straight or branched-chain alkyl, optionally comprising one or more phenyl (—$C_6H_5$) groups, and that optionally are methyl-, ethyl-, hydroxyl- or fluoro-substituted, including Boc and Cbz groups. In certain specific embodiments, in which R4 is TEMPO, the compound has one of the structures A, A1, A2, or A3 (Ac=Acetyl=$CH_3C(O)$—):

including a phenyl ($C_6H_5$) group, that optionally is methyl-, hydroxyl- or fluoro-substituted, including 2-methyl propyl, benzyl, methyl-, hydroxyl- or fluoro-substituted benzyl, such as 4-hydroxybenzyl. R4 is an —N—O., —N—OH or N=O containing group. R is —C(O)—R5 or —C(O)O—R5, and R5 is $C_1$-$C_6$ straight or branched-chain alkyl, optionally comprising one or more phenyl (—$C_6H_5$) groups, and that optionally are methyl-, ethyl-, hydroxyl- or fluoro-substituted, including Boc and Cbz groups. In certain specific embodiments, in which R4 is TEMPO, the compound has one of the structures D, D1, D2, or D3 (Ac=Acetyl=$CH_3C(O)$—):

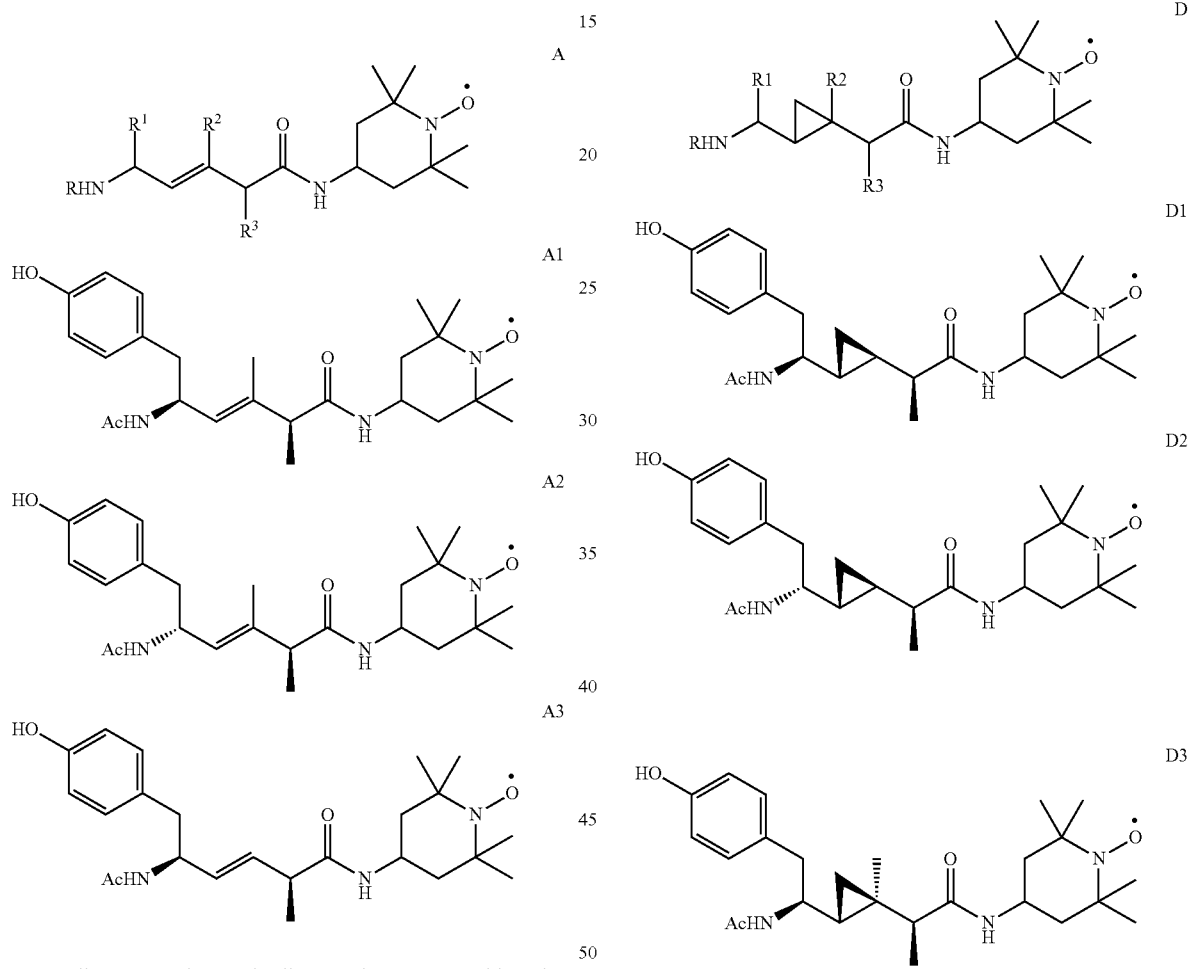

According to another embodiment, the compound has the structure

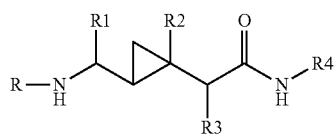

(Formula 3)

in which R1 and R3 are, independently, $C_1$-$C_6$ straight or branched-chain alkyl, optionally including a phenyl ($C_6H_5$) group, that optionally is methyl-, hydroxyl- or fluoro-substituted, including 2-methyl propyl, benzyl, methyl-, hydroxyl- or fluoro-substituted benzyl, such as 4-hydroxybenzyl. R2 is H or a $C_1$-$C_6$ straight or branched-chain alkyl, optionally The compounds described above, such as the compound of Formula 1, can be synthesized by any useful method. The compound JP4-039 was synthesized by the method of Example 8. In one embodiment, a method of making a compound of formula 1 is provided. The compounds are synthesized by the following steps:

A. reacting an aldehyde of structure $R_1$—C(O)—, wherein, for example and without limitation, $R_1$ is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl, with (R)-2-methylpropane-2-sulfinamide to form an imine, for example

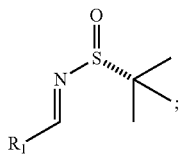

B. reacting a terminal alkyne-1-ol (CHC—R$_2$—C—OH), wherein, for example and without limitation, R$_2$ is not present or is branched or straight-chained alkylene, including methyl, ethyl, propyl, etc., with a tert-butyl)diphenylsilane salt to produce an alkyne, for example

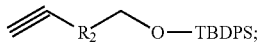

C. reacting (by hydrozirconation) the alkyne with the imine in the presence of an organozirconium catalyst to produce an alkene, for example

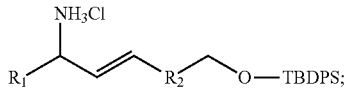

D. acylating the alkene to produce a carbamate, for example

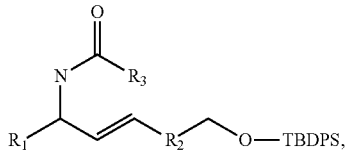

wherein, for example and without limitation, R$_3$ is C$_1$-C$_6$ straight or branched-chain alkyl, optionally including a phenyl (C$_6$H$_5$) group, that optionally is methyl-, hydroxyl- or fluoro-substituted, including including: methyl, ethyl, propyl, 2-propyl, butyl, t-butyl, pentyl, hexyl, benzyl, hydroxybenzyl (e.g., 4-hydroxybenzyl), phenyl and hydroxyphenyl;

E. removing the t-butyldiphenylsilyl group from the carbamate to produce an alcohol, for example

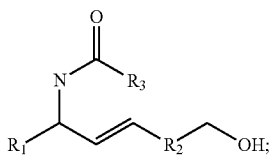

F. oxidizing the alcohol to produce a carboxylic acid, for example

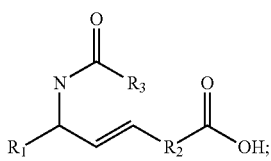

and

G. reacting the carboxylic acid with a nitroxide-containing compound comprising one of a hydroxyl or amine in a condensation reaction to produce the antioxidant compound, for example

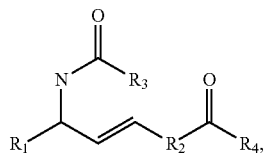

wherein R$_4$ is —NH—R$_4$ or —O—R$_4$, and R$_4$ is an —N—O., —N—OH or N=O containing group, such as described above.

Figure 2:
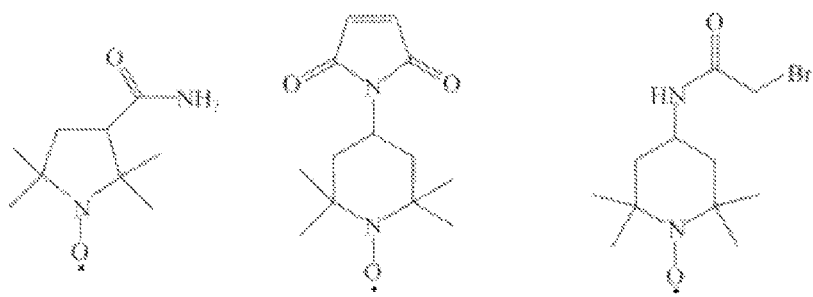
FIG. 2 provides examples of structures of certain mitochondria-targeting antioxidant compounds referenced herein, and the structure of TEMPOL.
Figures 1, 2:
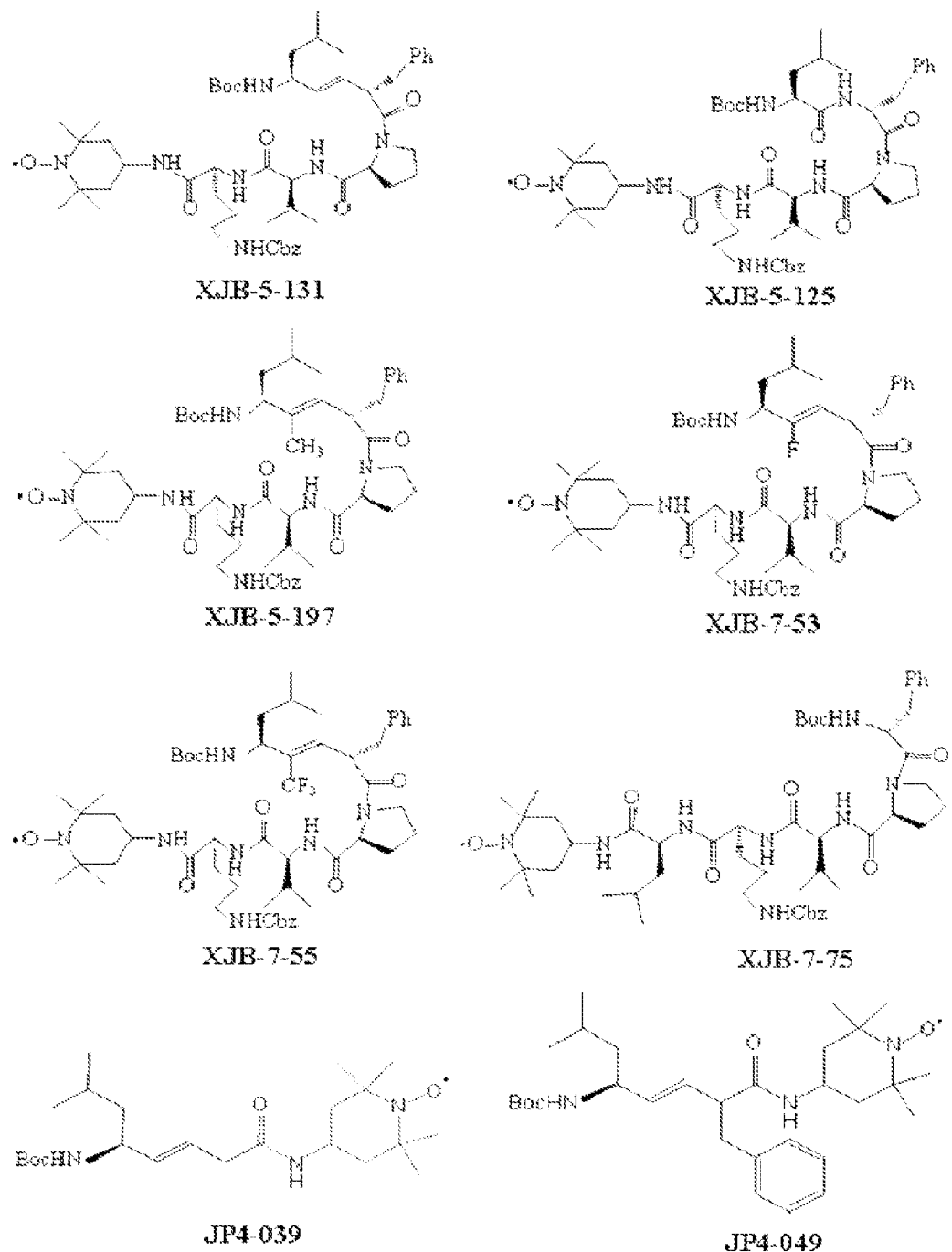
Figure 2:
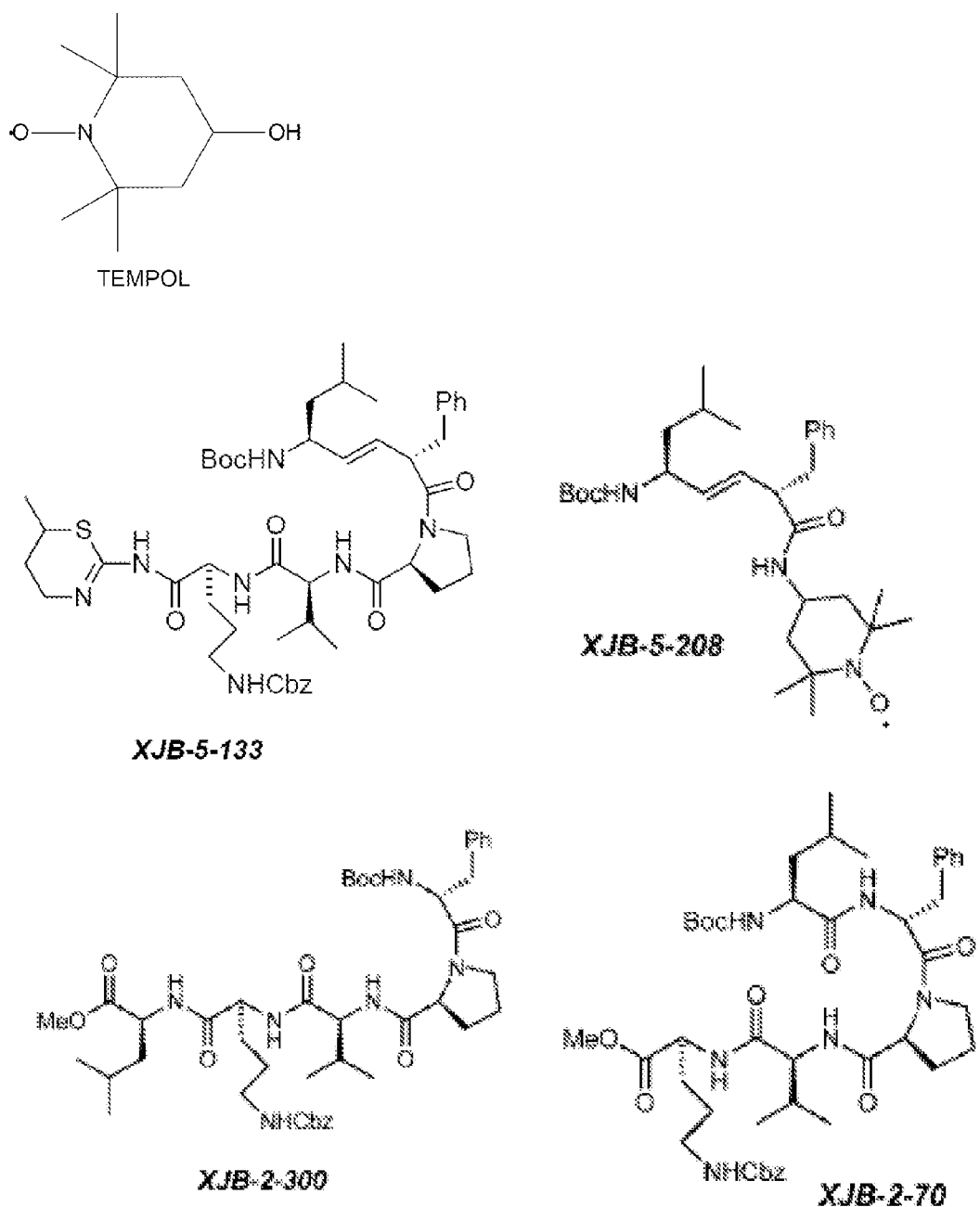

In another non-limiting embodiment, a compound is provided having the structure R1—R2—R3 in which R1 and R3 are a group having the structure —R4—R5, in which R4 is a mitochondria targeting group and R5 is —NH—R6, —O—R6 or —CH$_2$—R6, wherein R6 is an —N—O., —N—OH or N=O containing group, such as TEMPO. R1 and R2 may be the same or different. Likewise, R4 and R5 for each of R1 and R3 may be the same or different. R2 is a linker that, in one non-limiting embodiment, is symmetrical. In one embodiment, R1 and R2 have the structure shown in formulas 1, 2, or 3, above, with all groups as defined above, including structures A, A1, A2 A3, D, D1, D2 and D3, above, an example of which is compound JED-E71-58. Examples of gramicidin derivatives are provided herein, such as XJB-5-131 and XJB-5-125 (see, FIG. 2), and are further described both structurally and functionally in United States Patent Publication Nos. 20070161573 and 20070161544 as well as in Jiang, J, et al. (Structural Requirements for Optimized Delivery, Inhibition of Oxidative Stress, and Antiapoptotic Activity of Targeted Nitroxides, *The Journal of Pharmacology and Experimental Therapeutics* (2007) 320(3):1050-60, see also, Hoye, A T et al., Targeting Mitochondria, *Accounts of Chemical Research* (2008) 41(1):87-97, see also, Wipf, P, et al., Mitochondrial Targeting of Selective Electron Scavengers: Synthesis and Biological Analysis of Hemigramicidin-TEMPO Conjugates, (2005) *J. Am. Chem. Soc.* 2005, 127, 12460-12461). The XJB compounds can be linked into a dimer, for example and without limitation, by reaction with the nitrogen of the BocHN groups (e.g., as in XJB-5-131), or with an amine, if present, for instance, if one or more amine groups of the compound is not acylated to form an amide (such as NHBoc or NHCbx).

In Jiang, J, et al. (*The Journal of Pharmacology and Experimental Therapeutics* (2007) 320(3):1050-60), using a model of ActD-induced apoptosis in mouse embryonic cells, the authors screened a library of nitroxides to explore structure-activity relationships between their antioxidant/antiapoptotic properties and chemical composition and three-dimensional (3D) structure. High hydrophobicity and effective mitochondrial integration were deemed necessary but not sufficient for high antiapoptotic/antioxidant activity of a nitroxide conjugate. By designing conformationally preorganized peptidyl nitroxide conjugates and characterizing their 3D structure experimentally (circular dichroism and NMR) and theoretically (molecular dynamics), they established that the presence of the β-turn/β-sheet secondary structure is essential for the desired activity. Monte Carlo simulations in model lipid membranes confirmed that the conservation of the D-Phe-Pro reverse turn in hemi-GS analogs ensures the specific positioning of the nitroxide moiety at the mitochondrial membrane interface and maximizes their protective effects. These insights into the structure-activity relationships of nitroxide-peptide and -peptide isostere conjugates are helpful in the development of new mechanism-based therapeutically effective agents, such as those described herein.

Targeting group R4 may be a membrane active peptide fragment derived from an antibiotic molecule that acts by targeting the bacterial cell wall. Examples of such antibiotics include: bacitracins, gramicidins, valinomycins, enniatins, alamethicins, beauvericin, serratomolide, sporidesmolide, tyrocidins, polymyxins, monamycins, and lissoclinum peptides. The membrane-active peptide fragment derived from an antibiotic may include the complete antibiotic polypeptide, or portions thereof having membrane, and preferably mitochondria-targeting abilities, which is readily determined, for example, by cellular partitioning experiments using radiolabled peptides. Examples of useful gramicidin-derived membrane avctive peptide fragments are the Leu-D-Phe-Pro-Val-Orn and D-Phe-Pro-Val-Orn-Leu hemigramicidin fragments. As gramicidin is cyclic, any hemigramicidin 5-mer is expected to be useful as a membrane active peptide fragment, including Leu-D-Phe-Pro-Val-Orn, D-Phe-Pro-Val-Orn-Leu, Pro-Val-Orn-Leu-D-Phe, Val-Orn-Leu-D-Phe-Pro and Orn-Leu-D-Phe-Pro-Val (from Gramicidin S). Any larger or smaller fragment of gramicidin, or even larger fragments containing repeated gramicidin sequences (e.g., Leu-D-Phe-Pro-Val-Orn-Leu-D-Phe-Pro-Val-Orn-Leu-D-Phe-Pro) are expected to be useful for membrane targeting, and can readily tested for such activity. In one embodiment, the Gramicidin S-derived peptide comprises a β-turn, which appears to confer to the peptide a high affinity for mitochondria. Derivatives of Gramicidin, or other antibiotic fragments, include isosteres (molecules or ions with the same number of atoms and the same number of valence electrons—as a result, they can exhibit similar pharmacokinetic and pharmacodynamic properties), such as (E)-alkene isosteres (see, United States Patent Publication Nos. 20070161573 and 20070161544 for exemplary synthesis methods). As with Gramicidin, the structure (amino acid sequence) of bacitracins, other gramicidins, valinomycins, enniatins, alamethicins, beauvericin, serratomolide, sporidesmolide, tyrocidins, polymyxins, monamycins, and lissoclinum peptides are all known, and fragments of these can be readily prepared and their membrane-targeting abilities can easily be confirmed by a person of ordinary skill in the art.

Alkene isosteres such as (E)-alkene isosteres of Gramicidin S (i.e., hemigramicidin) were used as part of the targeting sequence. See FIG. 3 for a synthetic pathway for (E)-alkene isosteres and reference number 2 for the corresponding chemical structure. First, hydrozirconation of alkyne (FIG. 3, compound 1) with $Cp_2ZrHCl$ is followed by transmetalation to $Me_2Zn$ and the addition of N-Boc-isovaleraldimine. The resulting compound (not shown) was then worked up using a solution of tetrabutylammonium fluoride ("TBAF") and diethyl ether with a 74% yield. The resulting compound was then treated with acetic anhydride, triethylamine (TEA), and 4-N,N$^1$-(dimethylamino) pyridine ("DMAP") to provide a mixture of diastereomeric allylic amides with a 94% yield which was separated by chromatography. Finally, the product was worked up with $K_2CO_3$ in methanol to yield the (E)-alkene, depicted as compound 2. The (E)-alkene, depicted as compound 2 of FIG. 3, was then oxidized in a multi-step process to yield the compound 3 (FIG. 2)—an example of the (E)-alkene isostere.

Figure 3:
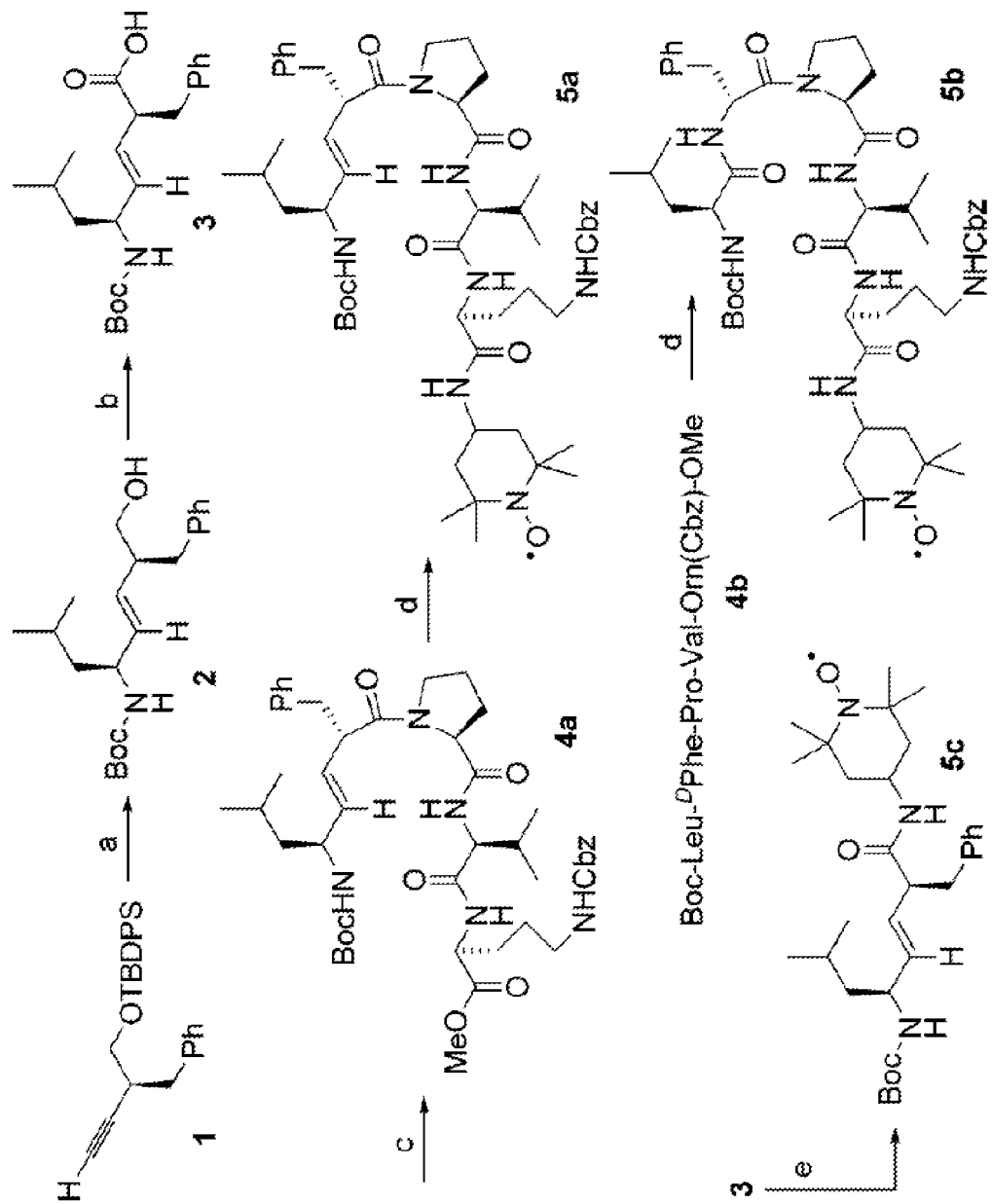
FIG. 3 depicts an example of a synthetic pathway for the TEMPO-hemigramicidin conjugates.

The compound 3 of FIG. 3 was then conjugated with the peptide H-Pro-Val-Orn (Cbz)-OMe using 1-ethyl-3-(3-dimethylaminopropyl carbodimide hydrochloride) (EDC) as a coupling agent. The peptide is an example of a suitable targeting sequence having affinity for the mitochondria of a cell. The resulting product is shown as compound 4a in FIG. 3. Saponification of compound 4a followed by coupling with 4-amino-TEMPO (4-AT) afforded the resulting conjugate shown as compound 5a in FIG. 3, in which the Leu-$^D$Phe peptide bond has been replaced with an (E)-alkene.

In an alternate embodiment, conjugates 5b in FIG. 3 was prepared by saponification and coupling of the peptide 4b (Boc-Leu-$^D$Phe-Pro-Val-Orn(Cbz)-OMe) with 4-AT. Similarly, conjugate 5c in FIG. 3 was prepared by coupling the (E)-alkene isostere as indicated as compound 3 in FIG. 3 with 4-AT. These peptide and peptide analogs are additional examples of suitable targeting sequences having an affinity to the mitochondria of a cell.

In another embodiment, peptide isosteres may be employed as the conjugate. Among the suitable peptide isosteres are trisubstituted (E)-alkene peptide isosteres and cyclopropane peptide isosteres, as well as all imine addition products of hydro- or carbometalated internal and terminal alkynes for the synthesis of di and trisubstituted (E)-alkene and cyclopropane peptide isosteres. See Wipf et al. *Imine additions of internal alkynes for the synthesis of trisubstituted (E)-alkene and cyclopropane isosteres*, ADV. SYNTH. CATAL. 347, 1605-1613 (2005). These peptide mimetics have been found to act as β-turn promoters. See Wipf et al. *Convergent Approach to (E)-Alkene and Cyclopropane Peptide Isosteres*, Organic Letters, VOL. 7, No. 103-106 (2005).

The linker, R2, may be any useful linker, chosen for its active groups, e.g., carboxyl, alkoxyl, amino, sulfhydryl, amide, etc. Typically, aside from the active groups, the remainder is non-reactive (such as saturated alkyl or phenyl), and does not interfere, sterically or by any other physical or chemical attribute, such as polarity or hydrophobicity/hydrophilicity, in a negative (loss of function) capacity with the activity of the overall compound. In one embodiment, aside from the active groups, the linker comprises a linear or branched saturated $C_4$-$C_{20}$ alkyl. In one embodiment, the linker, R2 has the structure

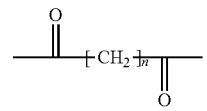

in which n is 4-18, including all integers therebetween, in one embodiment, 8-12, and in another embodiment, 10.

A person skilled in the organic synthesis arts can synthesize these compounds by crosslinking groups R1 and R3 by any of the many chemistries available. In one embodiment, R1 and R3 are to R2 by an amide linkage (peptide bond) formed by dehydration synthesis (condensation) of terminal carboxyl groups on the linker and an amine on R1 and R3 (or vice versa). In one embodiment, R1 and R3 are identical or different and are selected from the group consisting of: XJB-5-131, XJB-5-125, XJB-7-75, XJB-2-70, XJB-2-300, XJB-5-208, XJB-5-197, XJB-5-194, JP4-039 and JP4-049, attached in the manner shown in FIGS. 26A and 26B.

In a therapeutic embodiment, a method of accelerating bone repair or increasing bone density (e.g. an osteoporosis patient) in a subject (e.g., a patient in need of treatment to accelerate bone repair or increase bone density, such as a patient having a bone injury, pathology or degenerative condition, such as osteoporosis, in which bone repair is desired)

is provided, comprising administering to the subject an amount of a compound described above and having a free-radical scavenging group, such as a nitroxide-containing group effective to accelerate bone healing, repair, growth, etc. As described above, a number of diseases, conditions or injuries involving bone injury can be ameliorated or otherwise treated or prevented by administration of such compounds as those described herein. In one embodiment, the subject is non-irradiated or minimally-irradiated, meaning that the subject has either not been exposed to radiation or has not been exposed to 1-10 Gy or more of radiation within 14, 7, 6, 5, 4, 3, 2, or 1 days of administration of the compound. The subject may have been minimally irradiated, and thus has received diagnostic amounts of radiation, typically including insignificant amounts of radiation less than 1 Gy, 5 Gy or 10 Gy, and typically in the milliGy or milliSv range, such as in exposure to x-rays for diagnostic purposes or during air travel, as opposed to chemotherapeutic doses which typically are much higher.

In any case, as used herein, any agent or agents used for accelerating bone healing (including bone growth and/or repair and/or increasing bone density) in a subject is administered in an amount effective to accelerate bone healing or increasing bone density, namely in an amount and in a dosage regimen effective to accelerate bone repair or to reduce the duration and/or severity of bone injury or deficiency caused by an injury, pathology or degenerative condition. According to one non-limiting embodiment, an effective dose ranges from 0.1 or 1 mg/Kg to 100 mg/Kg, including any increment or range therebetween, including 1 mg/Kg, 5 mg/Kg, 10 mg/Kg, 20 mg/Kg, 25 mg/Kg, 50 mg/Kg, and 75 mg/Kg. However, for each compound described herein, an effective dose or dose range is expected to vary from that of other compounds described herein for any number of reasons, including the molecular weight of the compound, bioavailability, specific activity, etc. For example and without limitation, where XJB-5-131 is the antioxidant, the dose may be between about 0.1 and 20 mg/kg, or between about 0.3 and 10 mg/kg, or between about 2 and 8 mg/kg, or about 2 mg/kg and where either JP4-039, JED-E71-37 or JED-E71-58 is the antioxidant, the dose may be between about 0.01 and 50 mg/kg, or between about 0.1 and 20 mg/kg, or between about 0.3 and 10 mg/kg, or between about 2 and 8 mg/kg, or about 2 mg/kg. The therapeutic window between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding bone healing, growth, repair, etc. Different concentrations of the agents described herein are expected to achieve similar results, with the drug product administered, for example and without limitation, once prior to an expected bone injury, such as prior to surgery, during bone injury (such as during a surgical procedure), or after bone injury in any effective dosage regimen. For osteoporosis or similar conditions, the composition may be administered prophylactically, such as in a susceptible population, for example in postmenopausal women. The compounds can be administered continuously, such as intravenously, one or more times daily, once every two, three, four, five or more days, weekly, monthly, etc., including increments therebetween. A person of ordinary skill in the pharmaceutical and medical arts will appreciate that it will be a matter of simple design choice and optimization to identify a suitable dosage regimen for prevention, mitigation or treatment of bone injury and/or for bone healing (including growth or repair).

Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, inracardiac, subcutaneous, intraosseous, intradermal, intratheceal, intraperitoneal, transdermal, iontophoretic, transmucosal, epidural and intravitreal, with oral, intravenous, intramuscular and transdermal approaches being. preferred in many instances.

The compounds may be compounded or otherwise manufactured into a suitable composition for use, such as a pharmaceutical dosage form or drug product in which the compound is an active ingredient (see, for example, Example 18, below). Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disinegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

In one embodiment, the dosage form is a transdermal device, or "patch". The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matric fromed from a non-woven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies. As is shown in Example 12, below, certain formulations that may be useful as permeation enhancers include, without limitation: DMSO; 95% Propylene Glycol+5% Linoleic Acid; and 50% ETOH+40% HSO+5% Propylene Glycol+5% Brij30.

EXAMPLE 1

Materials. All chemicals were from Sigma-Aldrich (St Louis, Mo.) unless otherwise noted. Heparin, ketamine HCl and sodium pentobarbital were from Abbott Laboratories (North Chicago, Ill.). Dulbecco's modified Eagle medium ("DMEM") was from BioWhittaker (Walkersville, Md.). Fetal bovine serum (FBS; <0.05 endotoxin units/ml) was from Hyclone (Logan, Utah). Pyrogen-free sterile normal saline solution was from Baxter (Deerfield, Ill.).

General. All moisture-sensitive reactions were performed using syringe-septum cap techniques under an $N_2$ atmosphere and all glassware was dried in an oven at 150° C. for 2 h prior to use. Reactions carried out at −78° C. employed a $CO_2$-acetone bath. Tetrahydrofuran (THF) was distilled over sodium/benzophenone ketyl; $CH_2Cl_2$, toluene and $Et_3N$ were distilled from $CaH_2$. $Me_2Zn$ was purchased from Aldrich Company.

Reactions were monitored by thin layer chromatography ("TLC") analysis (EM Science pre-coated silica gel 60 F254 plates, 250 µm layer thickness) and visualization was accomplished with a 254 nm UV light and by staining with a Vaughn's reagent (4.8 g $(NH_4)_6Mo7O_{24}.4H_2O$, 0.2 g $Ce(SO_4)_2.4H_2O$ in 10 mL conc. $H_2SO_4$ and 90 mL $H_2O$). Flash chromatography on $SiO_2$ was used to purify the crude reaction mixtures.

Melting points were determined using a Laboratory Devices Mel-Temp II. Infrared spectra were determined on a Nicolet Avatar 360 FT-IR spectrometer. Mass spectra were obtained on a Waters Autospec double focusing mass spectrometer ("EI") or a Waters Q-T of mass spectrometer ("ESI"). LC-MS data were obtained on an Agilent 1100 instrument, using a Waters Xterra MS CH 3.5 µm RP column (4.6×100 mm).

Synthesis, Example I Prepared as a colorless oil (FIG. 3, compound 1) according to the literature procedure, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf P. et al., *Convergent Approach to (E)-Alkene and Cyclopropane Peptide Isosteres* ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127: 5742 (2005).

A solution of 2.20 g (5.52 mmol) of compound 1 (FIG. 3) in 20.0 mL of dry $CH_2Cl_2$ was treated at room temperature with 1.85 g (7.17 mmol) of $Cp_2ZrHCl$. The reaction mixture was stirred at room temperature for 5 min, $CH_2Cl_2$ was removed in vacuo and 20.0 mL of toluene was added. The resulting yellow solution was cooled to −78° C. and treated over a period of 30 min with 2.76 mL (5.52 mmol) of $Me_2Zn$ (2.0 M solution in toluene). The solution was stirred at −78° C. for 30 min, warmed to 0° C. over a period of 5 min and treated in one portion with 2.05 g (11.1 mmol) of N-Boc-isovaleraldimine, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf, P. et al., *Convergent Approach to (E)-Alkene and Cyclopropane Peptide Isosteres* J. ORG. LETT. 7:103 (2005); see also Xiao et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005).

The resulting mixture was stirred at 0° C. for 2 h, quenched with saturated $NH_4Cl$, diluted with EtOAc, filtered through a thin pad of Celite, and extracted with EtOAc. The organic layer was dried ($MgSO_4$), concentrated in vacuo, and purified by chromatography on $SiO_2$ (20:1, hexane/EtOAc) to yield 3.13 g (97%) as a colorless, oily 1:1 mixture of diastereomers.

A solution of 4.19 g (7.15 mmol) of product in 100 mL of dry tetrahydrofuran ("THF") was treated at 0° C. with 9.30 mL (9.30 mmol) of tetrabutylammoniumflouride (TBAF, 1.0 M solution in THF). The reaction mixture was stirred at room temperature for 20 h, diluted with EtOAc, and washed with brine. The organic layer was dried ($MgSO_4$), concentrated in vacuo, and purified by chromatography on $SiO_2$ (4:1, hexane/EtOAc) to yield 1.89 g (76%) as a light yellowish, foamy 1:1 mixture of diastereomers.

A solution of 1.86 g (5.23 mmol) of product in 40.0 mL of dry $CH_2Cl_2$ was treated at 0° C. with 1.46 mL (10.5 mmol) of triethylamine ("TEA"), 2.02 mL (21.4 mmol) of $Ac_2O$, and 63.9 mg (0.523 mmol) of 4-N,N'-(dimethylamino) pyridine ("DMAP"). The reaction mixture was stirred at 0° C. for 15 min and at room temperature for 3 h, diluted with EtOAc, and washed with brine. The organic layer was dried ($MgSO_4$), concentrated in vacuo, and purified by chromatography on $SiO_2$ (20:1, hexane/$Et_2O$) to yield 1.97 g (94%) of acetic acid (2S)-benzyl-(5R)-tert-butoxycarbonylamino-7-methyloct-(3E)-enyl ester (807 mg, 38.7%), acetic acid (2S)-benzyl-(5S)-tert-butoxycarbonylamino-7-methyloct-(3E)-enyl ester (826 mg, 39.6%), and a mixture of the aforementioned species (337 mg, 16.2%).

A solution of 350 mg (0.899 mmol) of acetic acid (2S)-benzyl-(5S)-tert-butoxycarbonylamino-7-methyloct-(3E)-enyl ester in 8.00 mL of MeOH was treated at 0° C. with 62.0 mg (0.449 mmol) of $K_2CO_3$. The reaction mixture was stirred at 0° C. for 1 h and at room temperature for an additional 4 h, diluted with EtOAc, and ashed with $H_2O$. The organic layer was dried ($MgSO_4$), concentrated in vacuo, and purified by chromatography on $SiO_2$ (4:1, hexane/EtOAc) to yield 312 mg (quant.) of compound 2 (FIG. 3) as a colorless oil.

A solution of 23.0 mg (66.2 µmol) of compound 2 (FIG. 3) in 2.00 mL of dry $CH_2Cl_2$ was treated at 0° C. with 42.1 mg (99.3 mol) of Dess-Martin Periodinane. The reaction mixture was stirred at 0° C. for 1 h and at room temperature for an additional 4 h, quenched with saturated $Na_2S_2O_3$ in a saturated $NaHCO_3$ solution, stirred for 30 min at room temperature, and extracted with $CH_2Cl_2$. The organic layer was dried ($Na_2SO_4$), concentrated in vacuo to give a colorless foam and subsequently dissolved in 3.00 mL of THF, and treated at 0° C. with 300 nt (600 µmol) of 2-methyl-2-butene (2.0 M solution in THF) followed by another solution of 18.0 mg (199 µmol) of $NaClO_2$ and 18.2 mg (132 µmol) of $NaH_2PO_4.H_2O$ in 3.00 mL of $H_2O$. The reaction mixture was stirred at 0° C. for 1 h and at room temperature for an additional 3 h, extracted with EtOAc, and washed with $H_2O$. The organic layer was dried ($Na_2SO_4$) and concentrated in vacuo to yield compound 3 (FIG. 3) as a crude colorless foam that was used for the next step without purification.

A solution of crude compound 3 (FIG. 3) (66.2 µmol) in 3.00 mL of $CHCl_3$ was treated at 0° C. with 10.7 mg (79.2 µmol) of 1-hydroxybenzotrizole ("HOBt") and 14.0 mg (73.0 µmol) of 1-ethyl-3-(3-dimethylaminopropyl) carbodiimide hydrochloride ("EDC"), followed by a solution of 62.9 mg (132 µmol) of H-Pro-Val-Orn(Cbz)-OMc, see Edmonds, M. K. et al. *Design and Synthesis of a Confomiationally Restricted Trans Peptide Isostere Based on the Bioactive Conformations of Saquinavir and Nelfinavir* J. ORG. CHEM. 66:3747 (2001); see also Wipf P. et al., *Convergent Approach to (E)-Alkene and Cyclopropane Peptide Isosteres* J. ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005), in 1.00 mL of $CHCl_3$ and 0.8 mg (6.6 µmol) of DMAP. The reaction mixture was stirred at room temperature for 2 d, diluted with $CHCl_3$, and washed with $H_2O$. The organic layer was dried ($Na_2SO_4$), concentrated in vacuo, and purified by chromatography on $SiO_2$ (from 2:1, hexanes/EtOAc to 20:1, $CHCl_3$/MeOH) to yield 51.3 mg (94%) of compound 4a (FIG. 3) as a colorless foam.

A solution of 53.7 mg (65.5 μmol) of compound 4a (FIG. 3) in 2.00 mL of MeOH was treated at 0° C. with 655 μL (655 μmol) of 1 N NaOH. The reaction mixture was stirred at room temperature for 6 h, and treated with 655 μL (655 μmol) of 1 N HCl. The solution was extracted with $CHCl_3$ and the organic layer was dried ($Na_2SO_4$) and concentrated in vacuo to give the crude acid as a colorless form. This acid was dissolved in 5.00 mL of $CHCl_3$ and treated at room temperature with 10.6 mg (78.4 μmol) of HOBt, 15.1 mg (78.8 μmol) of EDC, 20.2 mg (118 μmol) of 4-amino-TEMPO and 8.0 mg (65.5 μmol) of DMAP. The reaction mixture was stirred at room temperature for 36 h, diluted with $CHCl_3$, and washed with $H_2O$. The organic layer was dried ($Na_2SO_4$), concentrated in vacuo, and purified by chromatography on $SiO_2$ (from 1:1, hexane/EtOAc to 20:1, $CHCl_3$/MeOH) to yield 62.0 mg (99%) of compound 5a (FIG. 3) as a colorless solid. The following characterization data were obtained: LC-MS (Rt 8.81 min, linear gradient 70% to 95% $CH_3CN(H_2O)$ in 10 min, 0.4 mL/min; m/z=959.5 [M+H]$^+$, 981.5 [M+Na]$^+$) and HRMS (ESI) m/z calculated for $C_{53}H_{80}N_7O_9Na$ (M+Na) 981.5915, found 981.5956.

A solution of 60.0 mg (71.7 μmol) of compound 4b (FIG. 3), see Tamaki, M. et al. I. BULL. CHEM. SOC. JPN, 66:3113 (1993), in 2.15 mL of MeOH was treated at room temperature with 717 tL (717 μmol) of 1 N NaOH. The reaction mixture was stirred at room temperature for 5 h, and treated at 0° C. with 717 μL (717 μmol) of 1 N HCl. The solution was extracted with $CHCl_3$ and the organic layer was dried ($Na_2SO_4$) and concentrated in vacuo to give the crude acid as colorless foam. The acid was dissolved in 6.04 mL of $CHCl_3$ and treated at room temperature with 11.6 mg (85.8 μmol) of HOBt, 16.5 mg (85.1 μmol) of EDC, 18.5 mg (108 μmol) of 4-amino-TEMPO and 8.8 mg (72.0 μmol) of DMAP. The reaction mixture was stirred at room temperature for 20 h, diluted with $CHCl_3$, and washed with $H_2O$. The organic layer was dried ($Na_2SO_4$), concentrated in vacuo, and purified by chromatography on $SiO_2$ (from 2:1, hexane/EtOAc; to 20:1, $CHCl_3$/MeOH) to yield 69.6 mg (99%) of compound 5b (FIG. 3) as a yellowish solid. The following characterization data were obtained: LC-MS (Rt 7.02 min, linear gradient 70% to 95% $CH_3CN(H_2O)$ in 10 min, 0.4 mL/min; m/z=976.5 [M+H], 998.4 [M+Na]$^+$) and HRMS (ESI) m/z calculated for $C_{52}H_{79}N_8O_{10}Na$ (M+Na) 998.5817, found 998.5774.

A solution of crude compound 3 (FIG. 3) (40.3 μmol) in 3.00 mL of $CH_2Cl_2$ was treated at 0° C. with 10.4 mg (60.7 μmol) of 4-amino-TEMPO, 7.7 mg (40.2 μmol) of EDC, and 5.4 mg (44.2 μmol) of DMAP. The reaction mixture was stirred at room temperature for 20 h, diluted with $CHCl_3$, and washed with $H_2O$. The organic layer was dried ($Na_2SO_4$), concentrated in vacuo, and purified by chromatography on $SiO_2$ (from 4:1 to 1:1, hexane/EtOAc) to yield 18.8 mg (91%) of compound 5c (FIG. 3) as a yellowish solid. The following characterization data were obtained: LC-MS (Rt 7.01 min, linear gradient 70% to 95% $CH_3CN(H_2O)$ in 10 min, 0.4 mL/min; m/z=537.3 [M+Na]$^+$) and HRMS (ESI) m/z calculated for $C_{30}H_{48}N_3O_4Na$ (M+Na) 537.3543, found 537.3509.

Determination of Intracellular Superoxide Radicals Oxidation-dependent fluorogenic dye, dihydroethidium ("DHE", Molecular Probes) was used to evaluate intracellular production of superoxide radicals. DHE is cell permeable and, in the presence of superoxide, is oxidized to fluorescent ethidium which intercalates into DNA. The fluorescence of ethidium was measured using a FACscan (Becton-Dickinson, Rutherford, N.J.) flow cytometer, equipped with a 488-nm argon ion laser and supplied with the Cell Quest software. Mean fluorescence intensity from 10,000 cells were acquired using a 585-nm bandpass filter (FL-2 channel).

Determination of Intracellular ATP levels. Cells were incubated with 10 μm of compound 5a (FIG. 3) for indicated periods of time (2, 4, 6, 12, and 14 h). At the end of incubation, cells were collected and the content of intracellular ATP was determined using a bioluminescent somatic cell assay kit (Sigma, St. Louis, Mass.). As a positive control, cells were incubated with 2 mM of 2-dexy-glucose, a glucose analogue which competitively inhibits cellular uptake and utilization of glucose, for 12 and 14 h.

Cells. Caco-2BBe human enterocyte-like epithelial cells were obtained from the American Type Culture Collection (Manassas, Va.). Cells were routinely maintained at 37° C. in under a humidified atmosphere containing 8% CO2 in air. The culture medium was DMEM supplemented with 10% FBS, non-essential amino acids supplement (Sigma-Aldrich catalogue #M7145), sodium pyruvate (2 mM), streptomycin (0.1 mg/ml), penicillin G (100 U/ml) and human transferrin (0.01 mg/ml). The culture medium was changed 3 times per week.

Surgical Procedures to Obtain Vascular Access. All study protocols using rats followed the guidelines for the use of experimental animals of the US National Institutes of Health and were approved by the Institutional Animal Care and Use Committee at the University of Pittsburgh.

Male specific pathogen-free Sprague Dawley rats (Charles River Laboratories, Wilmington, Mass.), weighing 150-250g, were housed in a temperature-controlled environment with a 12-h light/dark cycle. The rats had free access to food and water. For experiments, rats were anesthetized with intramuscular ketamine HCl (30 mg/kg) and intraperitoneal sodium pentobarbital (35 mg/kg). Animals were kept in a supine position during the experiments. Lidocaine (0.5 ml of a 0.5% solution) was injected subcutaneously to provide local anesthesia at surgical cut-down sites. In order to secure the airway, a tracheotomy was performed and polyethylene tubing (PE 240; Becton Dickinson, Sparks, Md.) was introduced into the trachea Animals were allowed to breathe spontaneously.

The right femoral artery was cannulated with polyethylene tubing (PE 10). This catheter was attached to a pressure transducer that allowed instantaneous measurement of mean arterial pressure (M A P) during the experiment. For experiments using the pressure-controlled hemorrhagic shock (HS) model, the right jugular vein was exposed, ligated distally, and cannulated with polyethylene tubing (PE 10) in order to withdraw blood. For experiments using the volume-controlled hemorrhagic shock (HS) model, the jugular catheter was used to infuse the resuscitation solution and the right femoral vein, which was cannulated with a silicon catheter (Chronic-Cath, Norfolk Medical, Skokie, Ill.), was used to withdraw blood.

All animals were instrumented within 30 min Heparin (500 U/kg) was administered immediately after instrumentation through the femoral vein Animals were placed in a thermal blanket to maintain their body temperature at 37° C. The positioning of the different devices aforementioned was checked postmortem.

Intestinal Mucosal Permeability Assay. Animals were allowed access to water but not food for 24 h prior to the experiment in order to decrease the volume of intestinal contents. The rats were instrumented as described above. A midline laparotomy was performed and the small intestine was exteriorized from the duodenojejunal junction to the ileocecal valve. A small incision was made on the antimesenteric aspect of the proximal small intestine and saline solution (1.5 ml) was injected. The bowel was ligated proximally and distally to the incision with 4-0 silk (Look, Reading, Pa.).

The small intestine was compressed gently in aboral direction along its length to displace intestinal contents into the colon. Starting 5 cm from the ileocecal valve, the ileum was partitioned into six contiguous water-tight segments. Each segment was 3 cm long and was bounded proximally and distally by constricting circumferential 4-0 silk sutures. Care was taken to ensure that the vascular supply to intestine was not compromised, and each segment was well-perfused.

Two randomly selected segments in each rat were injected with 0.3 ml of vehicle and served as "no treatment" controls. In order to fill the segments, a small incision was made and the solution was injected using a Teflon catheter (Abbocath 16Ga, Abbot Laboratories).

The remaining four other segments were injected with solutions containing either 4-hydroxy-2,2,6,6-tetramethylpiperidine-N-oxyl (TEMPOL) or one of the Gramicidin S-based compounds. Four different final concentrations of TEMPOL in normal saline were evaluated: 0.1, 1, 5 and 20 mM. The hemigramicidin-based compounds were dissolved in a mixture of dimethylsulfoxide (DMSO) and normal saline (1:99 v/v) and injected at final concentrations of 0.1, 1, 10 or 100 µM.

After the segments were loaded with saline or the test compounds, the bowel was replaced inside the peritoneal cavity and the abdominal incision was temporarily closed using Backhaus forceps.

After a 5 min stabilization period, hemorrhagic shock was induced by withdrawing blood via the jugular catheter. MAP was maintained at 30±3 mm Hg for 2 hours. The shed blood was re-infused as needed to maintain MAP within the desired range.

After 2 h of shock, the animals were euthanized with an intracardiac KCl bolus injection. The ileum was rapidly excised from the ileocecal valve to the most proximal gut segment. The tips of each segment were discarded. In order to assay caspases 3 and 7 activity and phospholipids peroxidation, mucosa samples were collected from gut segments immediately after hemorrhage and stored at −80° C. For permeability measurements, each segment was converted into an everted gut sac, as previously described by Wattanasirichaigoon et al., see Wattanasirichaigoon, S. et al., *Effect of mesenteric ischemia and reperfusion or hemorrhagic shock on intestinal mucosal permeability and ATP content in rats*, SHOCK, 12:127-133 (1999).

Briefly, as per the Wattanasirichaigoon protocol referenced above, the sacs were prepared in ice-cold modified Krebs-Henseleit bicarbonate buffer ("KHBB"), pH 7.4. One end of the gut segment was ligated with a 4-0 silk suture; the segment was then everted onto a thin plastic rod. The resulting gut sac was mounted on a Teflon catheter (Abbocath 16GA, Abbot Laboratories) connected to a 3 ml plastic syringe containing 1.5 ml of KHBB. The sac was suspended in a beaker containing KHBB plus fluorescein-isothiocyanate labeled dextran (average molecular mass 4 kDa; FD4; 0.1 mg/ml). This solution was maintained at 37° C., and oxygenated by bubbling with a gas mixture ($O_2$ 95%/$CO_2$ 5%). After 30 min, the fluid within the gut sac was collected. The samples were cleared by centrifugation at 2000 g for 5 min.

Fluorescence of FD4 in the solution inside the beaker and within each gut sac was measured using a fluorescence spectrophotometer (LS-50, Perkin-Elmer, Palo Alto, Calif.) at an excitation wavelength of 492 nm and an emission wavelength of 515 nm. Mucosal permeability was expressed as a clearance normalized by the length of the gut sac with units of $nL \cdot min^{-1} \cdot cm^2$, as previously described, see Yang, R. et al., *Ethyl pyruvate modulates inflammatory gene expression in mice subjected to hemorrhagic shock*, AM. J. PHYSIOL. GASTROINTEST. LIVER PHYSIOL. 283:G212-G22 (2002).

Results for a specific experimental condition (i.e., specific test compound at a single concentration) were expressed as relative change in permeability calculated according to this equation: Relative change in permeability (%)=($C_{Hs\ exp}$−$C_{normal}$)/$C_{Hs\ cont}$−$C_{normal}$)×100, where $C_{HS\ exp}$ is the clearance of FD4 measured for a gut segment loaded with the experimental compound, $C_{normal}$ is the clearance of FD4 measured in 6 gut segments from 3 normal animals not subjected to hemorrhagic shock, and $C_{Hs\ cont}$ is the mean clearance of FD4 measured in 2 gut segments filled with vehicle from the same animal used to measure $C_{HS\ exp}$.

Measurement of Permeability of Caco-2 Monolayers. Caco-$2_{BBe}$ cells were plated at a density of $5×10^4$ cells/well on permeable filters (0.4 µm pore size) in 12-well bicameral chambers (Transwell, Costar, Corning, N.Y.). After 21 to 24 days, paracellular permeability was determined by measuring the apical-to-basolateral clearance of FD4.

Briefly, the medium on the basolateral side was replaced with control medium or medium containing menadione (50 µM final). Medium containing FD4 (25 mg/ml) was applied to the apical chamber. In some cases, one of the gramicidin S-based compounds, XJB-5-131, also was added to the apical side at final concentrations of 0.1, 1, 10 or 100 µM. After 6 hours of incubation, the medium was aspirated from both compartments. Permeability of the monolayers was expressed as a clearance ($pL \cdot h^{-1} \cdot cm^{-2}$), see Han, X. et al., *Proinflammatory cytokines cause NO dependent and independent changes in expression and localization of tight junction proteins in intestinal epithelial cells*, SHOCK 19:229-237 (2003).

Caspases 3 and 7 Activity Assay. Caspases 3 and 7 activity was measured using a commercially available assay kit, Caspase Glo™ 3/7 assay kit (Promega, Madison, Wis.). Briefly, 50 µl of rat gut mucosa homogenate (20 jug protein) was mixed with 50 µl of Caspase-Glo™ reagent and incubated at room temperature for 1 hour. At the end of incubation period, the luminescence of each sample was measured using a plate reading chemiluminometer (ML1000, Dynatech Laboratories, Horsham, Pa.). Activity of caspases 3 and 7 was expressed as luminescence intensity (arbitrary units per mg protein). Protein concentrations were determined using the BioRad assay (Bio-Rad Laboratories, Inc., Hercules, Calif.).

Assay for peroxidation of phospholipids. Gut mucosal samples were homogenized. Lipids were extracted from homogenates using the Folch procedure, see M. Lees and G. H. Sloan-Stanley, *A simple method for isolation and purification of total lipids from animal tissue*, J. BIOL. CHEM. 226:497-509 (1957), and resolved by 2D HPTLC (High Performance Thin Layer Chromatography) as previously described, see Kagan, V. E. et al., *A role for oxidative stress in apoptosis: Oxidation and externalization of phosphatidylserine is required for macrophage clearance of cell undergoing Fas-mediated apoptosis*, J. IMMUMOL. 169:487-489 (2002). Spots of phospholipids were scraped from HPTLC plates and phospholipids were extracted from silica. Lipid phosphorus was determined by a micro-method, see Bottcher, C. J. F. et al., *A rapid and sensitive sub-micro phosphorus determination*, ANAL. CHIM. ACTA 24: 203-204 (1961).

Oxidized phospholipids were hydrolyzed by pancreatic phospholipase A2 (2U/µl) in 25 mM phosphate buffer containing 1 mM $CaCl_2$, 0.5 mM EDTA and 0.5 mM sodium dodecyl sulfate (SDS) (pH 8.0, at room temperature for 30 min). Fatty acid hydroperoxides formed were determined by fluorescence HPLC of resorufin stoichiometrically formed during their microperoxidase 11-catalized reduction in presence of Amplex Red (for 40 min at 4° C.) (8). Fluorescence HPLC (Eclipse XDB-C18 column, 5 µm, 150×4.6 mm, mobile phase was composed of 25 mM disodium phosphate buffer (pH 7.0)/methanol (60:40 v/v); excitation wavelength 560 nm, emission wavelength 590 nm) was performed on a Shimadzu LC-100AT HPLC system equipped with fluorescence detector (RF-10Axl) and autosampler (SIL-10AD).

Survival of Rats Subjected to Volume-controlled Hemorrhagic Shock. Following surgical preparation and a 5-min stabilization period to obtain baseline readings, rats were subjected to hemorrhagic shock. Bleeding was carried out in 2 phases.

Initially, 21 ml/kg of blood was withdrawn over 20 min. Immediately thereafter, an additional 12.5 ml/kg of blood was withdrawn over 40 min. Thus, hemorrhage occurred over a total period of 60 min and the total blood loss was 33.5 ml/kg or approximately 55% of the total blood volume. Rats were randomly assigned to receive XJB-5-131 (2 µmmol/kg) or its vehicle, a 33:67 (v/v) mixture of DMSO and normal saline. XJB-5-131 solution or vehicle alone was administered as a continuous infusion during the last 20 min of the hemorrhage period. The total volume of fluid infused was 2.8 ml/kg and it was administered intravenously using a syringe pump (KD100, KD Scientific, New Hope, Pa.). Rats were observed for 6 hours or until expiration (defined by apnea for >1 min). At the end of the 6 hour observation period, animals that were still alive were euthanized with an overdose of KCl.

Blood pressure was recorded continuously using a commercial strain-gauge transducer, amplifier, and monitor (590603a, SpaceLabs, Redmond, Wash.). Blood samples (0.5 ml) were collected from the jugular vein at the beginning of hemorrhage (baseline), at the end of hemorrhage (shock) and at the end of resuscitation (resuscitation). Hemoglobin concentration [Hb], lactate and glucose concentration were determined using an auto-analyzer (Model ABL 725, Radiometer Copenhagen, Westlake, Ohio).

Data Presentation and Statistics. All variables are presented as means±Standard Error Mean (SEM). Statistical significance of differences among groups was determined using ANOVA (analysis of variance) and LSD (Least Significant Difference) tests, or Kruskal-Wallis and Mann-Whitney tests as appropriate. Survival data were analyzed using the log-rank test. Significance was declared for p values less than 0.05.

EXAMPLE 2

Selective delivery of TEMPO to mitochondria could lead to therapeutically beneficial reduction of ROS; therefore, investigation of the use of conjugates of 4-amino-TEMPO ("4-AT") was explored. In order to selective target the mitochondria, a targeting sequence using the membrane active antibiotic Gramicidin S ("GS") as well as corresponding alkene isosteres, shown in FIGS. 2 and 3. Accordingly, using the Gramicidin S peptidyl fragments and alkene isosteres as "anchors," the TEMPO "payload" could be guided into the mitochondria.

The Leu-$^D$Phe-Pro-Val-Orn fragment of hemigramicidin was used as a targeting sequence. Alkene isosteres such as (E)-alkene isosteres of Gramicidin S (i.e., hemigramicidin) were used as part of the targeting sequence. See FIG. 3 for the synthetic pathway for (E)-alkene isosteres and compound 3 for the corresponding chemical structure. The (E)-alkene as depicted in compound 2 of FIG. 3 was then oxidized in a multi-step process to yield the compound as depicted in compound 3 an example of the (E)-alkene isostere.

Then, the compound depicted as compound 3 of FIG. 3 was conjugated with the tripeptide H-Pro-Val-Orn(Cbz)-OMe using 1-ethyl-3-(3-dimethylaminopropyl) carbodiimide hydrochloride ("EDC") as a coupling agent. The tripeptide is an example of a suitable targeting sequence having affinity for the mitochondria of a cell. The resulting product is shown as compound 4a in FIG. 3. Saponification of compound 4a followed by coupling with 4-amino-TEMPO ("4-AT") afforded the resulting conjugates shown as compound 5a in FIG. 3, in which the Leu-$^D$Phe peptide bond has been replaced with an (E)-alkene.

Figure 4:
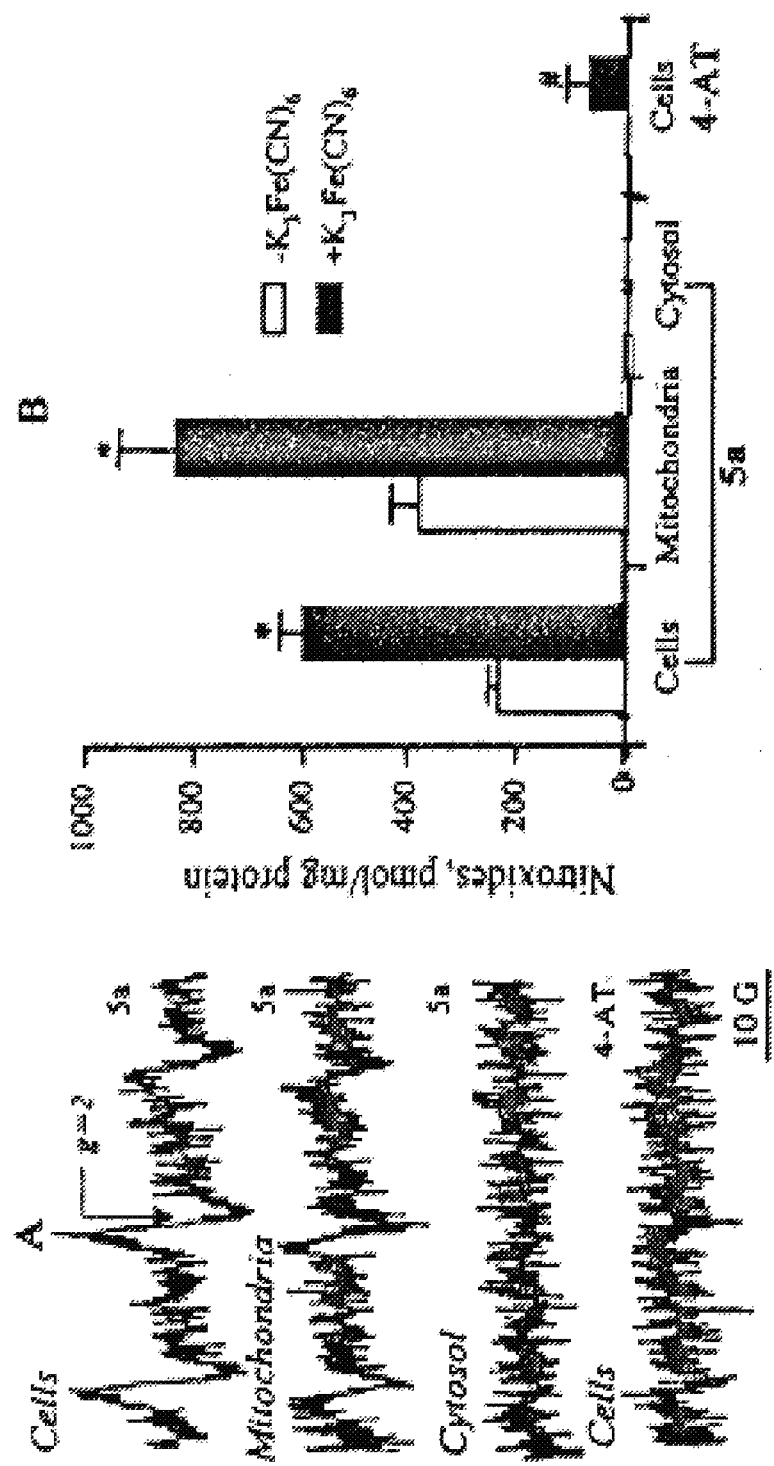
FIG. 4 shows an EPR-based analysis of integration and reduction of nitroxide Gramicidin S peptidyl-TEMPO conjugates in MECs.

In an alternate embodiment, conjugates 5b and 5c in FIG. 3 by coupling the peptide 4b (Boc-Leu-$^D$Phe-Pro-Val-Orn (Cbz)-OMe) and the (E)-alkene isostere as indicated as compound 3 in FIG. 3 to 4-AT. The peptide is another example of a suitable targeting sequence having an affinity with the mitochondria of a cell.

Electron paramagnetic resonance ("EPR") spectroscopy was used to monitor the cellular delivery of compounds 5a and 5b shown in FIG. 3 in mouse embryonic cells ("MEC").

The following conditions were used during the EPR-based analysis of the integration and reduction of nitroxide Gramicidin S-peptidyl conjugates in MECs. The MECs at a concentration of 10 million MECs per mL were incubated with 10 µM of 4-AT and compound 5a, respectively. Recovered nitroxide radicals in whole cells, mitochondria, and cytosol fractions were resuspended in phosphate buffer saline ("PBS") in the presence and absence, respectively, of 2 µM $K_3Fe(CN)_6$. In brief, FIG. 4A shows a representative EPR spectra of compound 5a in different fractions of MECs in the presence of $K_3Fe(CN)_6$. Further, FIG. 4B shows an assessment of integrated nitroxides.

Distinctive characteristic triplet signals of nitroxide radicals were detected in MECs incubated with 10 µM of compound 5a (FIG. 3) as well as in mitochondria isolated from these cells. The cytosolic function did not elicit EPR signals of nitroxide radicals; similar results were observed with conjugate 5b (FIG. 3) (data not shown).

Incubation of MECs with compound 5a (FIG. 3) resulted in integration and one-electron reduction of compound 5a, as evidenced by a significant increase in magnitude of the EPR signal intensity upon addition of a one-electron oxidant, ferricyanide (FIG. 4B). (Note: EPR results for incubation of MECs with 5b are not shown in FIG. 4; however, EPR results for 5b were similar when compared to 5a). In contrast to 5a and 5b, however, 4-amino-TEMPO (4-AT) did not effectively permeate cells or the mitochondria, as shown by the absence of significant amplitude change in the EPR results for 4-AT.

The ability of 5a, 5b (FIG. 3), and 4-AT to prevent intracellular superoxide generation by flow cytometric monitoring of oxidation of dihydroehtidium ("DHE") to a fluorescent ethidium was tested. The ability of 5a, 5b, and 4-AT to protect cells against apoptosis triggered by actinomycin D ("ActD") was also tested. MECs were pretreated with 10 µM 4-AT, 5a, or 5b then incubated with ActD at a concentration of 100 ng/mL. It was found that 5a and 5b completely inhibited nearly two-fold intracellular superoxide generation in MECs (sec FIG. 6A). 4-AT had no effect on the superoxide production in MECs.

Apoptotic cell responses were documented using three biomarkers: (1) externalization of phosphatidylserine ("PS") on the cell surface (by flow cytometry using an FITC-labeled PS-binding protein, annexin V, see FIGS. 6B and 6E); (2) activation of caspase-3 by cleavage of the Z-DEVD-AMC substrate (see FIG. 6C), and, (3) DNA fragmentation by flow cytometry of propidiium iodide stained DNA (see FIG. 6D).

Phosphatidylserine ("PS") is an acidic phospholipid located exclusively on the inner leaflet of the plasma membrane; exposure of PS on the cell surface is characteristic of cell apoptosis. Externalization of PS was analyzed by flow cytometry using an annexin V kit. Cells were harvested by trypsinization at the end of incubation and then stained with annexin V-FITC and propidium iodide ("PS"). Ten thousand cell events were collected on a FACScan flow cytometer. Cells that annexin V-positive and PI-negative were considered apoptotic.

Activation of capase-3, a cystein protease only activated in the execution phase of apoptosis, was determined using an EnzChek capsase-3 assay kit.

Further, calcium and magnesium dependent nucleases are activated that degrade DNA during apoptosis. These DNA fragments are eluted, stained with propidium iodide and analyzed using flow cytometry. A cell population with decreased DNA content was considered a fraction of apoptotic cells.

Figure 6:
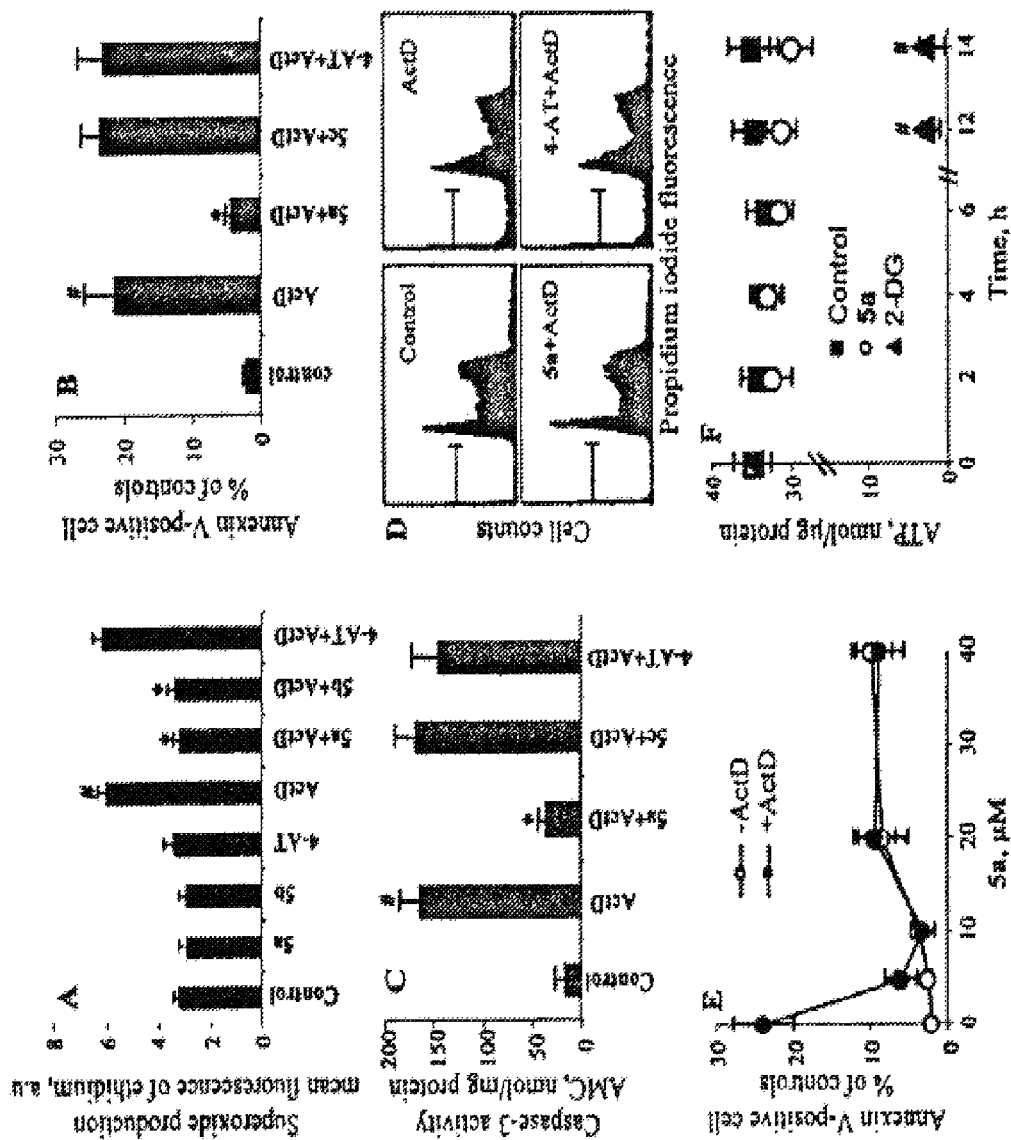
FIG. 6 shows graphical representations of the effect of nitroxide conjugates on ActD-induced apoptosis.
Figure 7B:
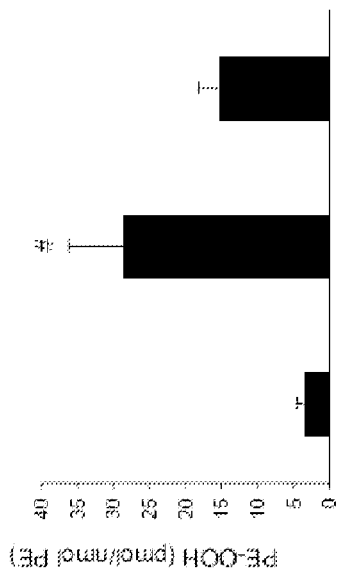
FIG. 7B is a graphical representation of peroxidation activity with respect to phosphatidylethanolamine ("PE").
Figure 7D:
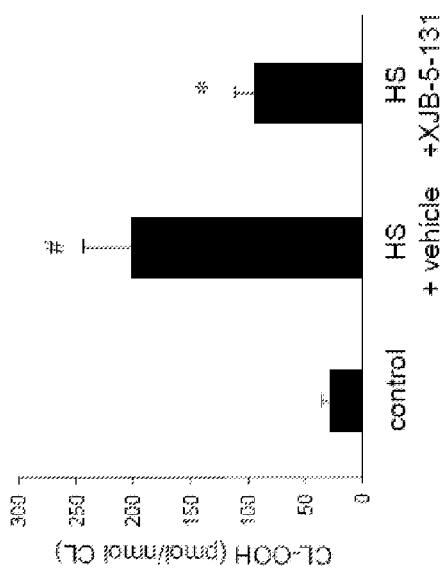
FIG. 7D is a graphical representation of peroxidation activity with respect to cardiolipin ("CL").
Figure 7A:
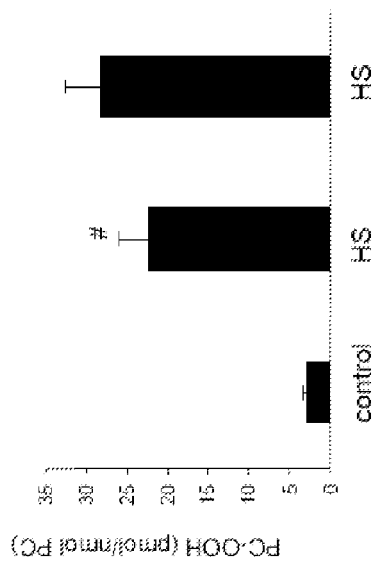
FIG. 7A is a graphical representation of the peroxidation of phosphatidylcholine ("PC").
Figure 7C:
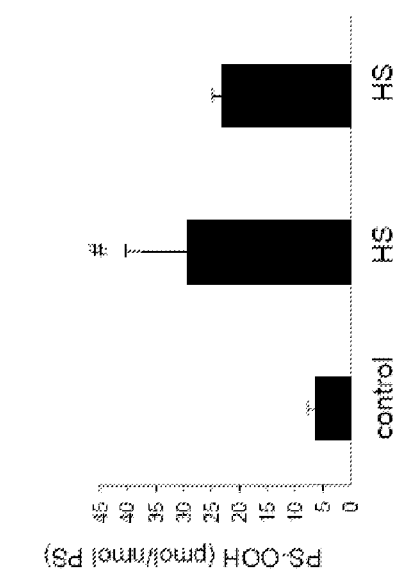
FIG. 7C is a graphical representation of peroxidation activity with respect to phosphatidylserine ("PS").

Anti-apoptotic effects of compounds 5a and 5b were observed at relatively low concentrations of 10 µM. Compounds 5a and 5b (FIG. 3) reduced the number of annexin V-positive cells as shown in FIG. 6B, prevented caspase-3 activation as shown in FIG. 6C, and prevented DNA fragmentation as shown in FIG. 6D. At concentrations in excess of 10 µM, both 5a and 5b were either less protective or exhibited cytotoxicity (FIG. 6E). In contrast, 4-AT afforded no protection.

In contrast, compound 5c, which does not have a complete targeting moiety, was ineffective in protecting MECs against ActD-induced apoptosis (FIGS. 6B and 6C) at low concentrations. Accordingly, the hemigramicidin peptidyl targeting sequence is essential for anti-apoptotic activity of nitroxide conjugates such as those containing TEMPO.

Finally, the reduction of compounds 5a and 5b could also cause inhibition of mitochondrial oxidative phosphorylation, so the ATP levels of MECs treated with these compounds were tested. As is known to one ordinarily skilled in the art, ATP serves as the primary energy source in biological organisms; reduction of ATP levels would greatly impair normal cell function. ATP levels in MECs in the presence or absence of 5a or 2-deoxyglucose ("2-DG") were used as a positive control (see FIG. 6F). At concentrations at which anti-apoptotic effects were maximal (~10 µM, FIG. 6E), nitroxide conjugates did not cause significant changes in the cellular ATP level. Therefore, synthetic GS-peptidyl conjugates migrate into cells and mitochondria where they are reduced without affecting the ability of the mitochondria to produce ATP.

EXAMPLE 3

In an in vivo assay, the ileum of rats was divided into a series of well-vascularized components in a manner akin to links of sausage. The lumen of each ileal compartment was filled with a 3 µL aliquot of test solution. Two of the ileal compartments were filled with vehicle alone (i.e., a solution containing at least in part the TEMPO derivative). These two components served as internal controls to account for individualistic variations in the severity of shock or the response of the mucosa to the shock.

Figure 5:
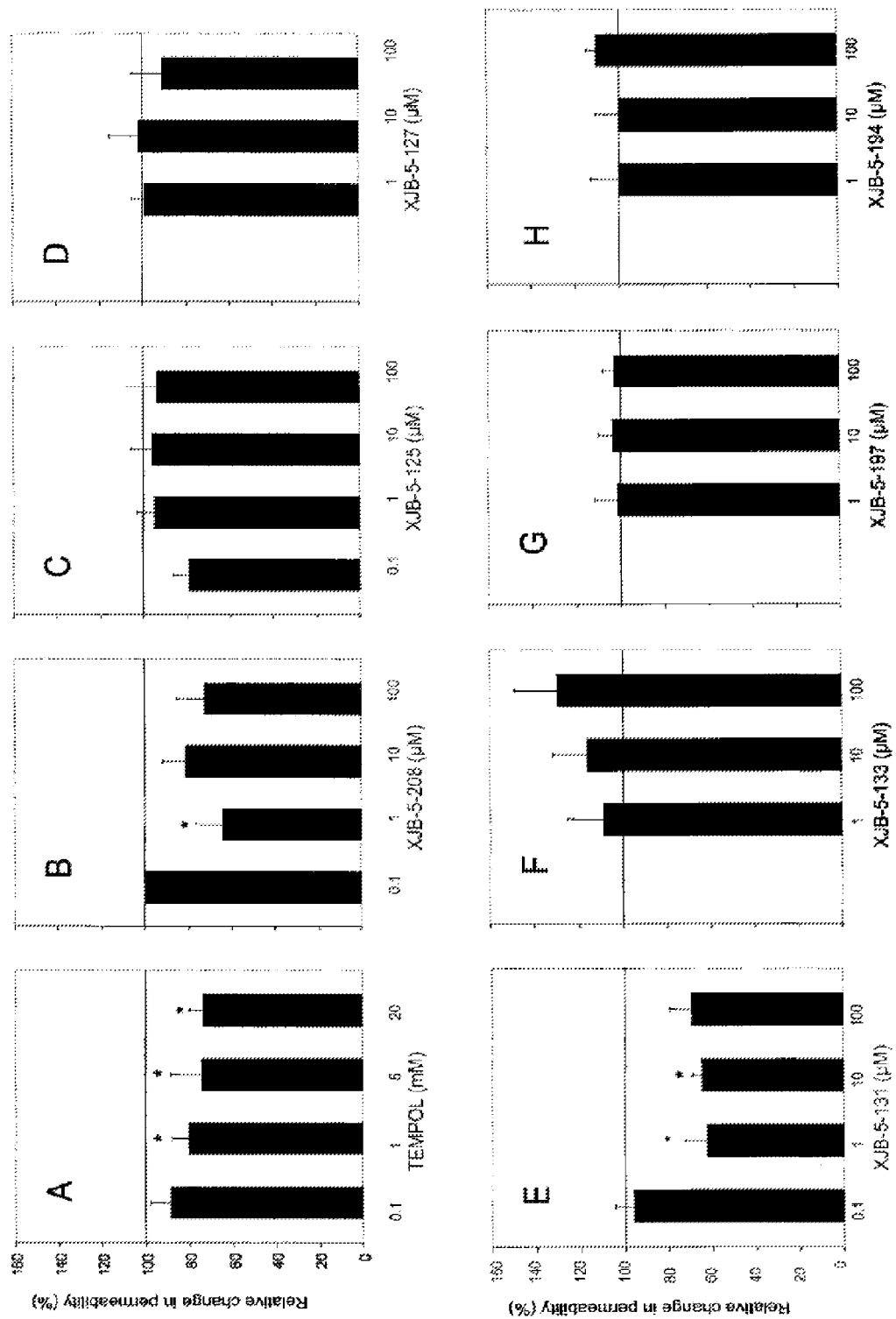
FIG. 5 shows a flourescein isothiocyanate-dextran (FD4) read-out which reflects the effect of Gramicidin-S TEMPO conjugates on rat ileal mucosal permeability following profound hemorrhagic shock. Data are expressed as a percentage of the change permeability relative to that observed in simultaneously assayed control segments loaded during shock with normal saline solution.

Using this assay system, eight compounds were evaluated as shown in FIG. 5: TEMPOL (FIG. 5A), one dipeptidic TEMPOL analog (FIG. 5B-XJB-5-208), 3 hemigramicidin-TEMPO conjugates (FIGS. 5C XJB-5-125, 5E XJB-5-131, and 5G XJB-5-197), and 3 hemigramicidin compounds that do not have the TEMPO moiety (FIGS. 5D-XJB-5-127, 5F-XJB-5-133, and 5H -XJB-5-194).

Hemorrhagic shock in rats leads to marked derangements in intestinal mucosal barrier function—in other words, the mucosal permeability of shocked intestinal segments was significantly greater than the permeability of segments from normal rats (52.3+0.5 versus 6.9+0.1 nL·min$^{31}$ $^{1}$·cm$^{-2}$, respectively; p<0.01). Accordingly, mice were subjected to 2 hours of shock (Mean Arterial Pressure ("MAP")=30 f 3 mm Hg), the gut segments were harvested and mucosal permeability to flourescein isothiocyanate-dextran ("FD4") measured ex vivo. Data in FIG. 5 are expressed as a percentage of the change permeability relative to that observed in simultaneously assayed control segments loaded during shock with normal saline solution.

Accordingly, intraluminal TEMPOL was used as a "positive control" for gut mucosal protection assay. TEMPOL concentrations >1 mM in the gut lumen ameliorated hemorrhagic shock-induced ileal mucosal hyperpermeability (FIG. 5A). Two of the TEMPO conjugates, namely XJB-5-208 (FIG. 5B) and XJB-5-131 (FIG. 5C), also significantly ameliorated hemorrhagic shock-induced ileal mucosal hyperpermeability. The lowest effective concentration for XJB-5-208 (FIG. 5B) and XJB-5-131 (FIG. 5E) was 1 µM; i.e., both of these compounds were ~1000-fold more potent than TEMPOL. Two other compounds carrying the TEMPO payload, XJB-5-125 (FIG. 5C) and XJB-5-197 (FIG. 5G) failed to provide protection against gut barrier dysfunction induced by hemorrhage. XJB-5-133 (FIG. 5F) has the same (hemigramicidin-based) mitochondrial targeting moiety as XJB-5-131 (FIG. 5E) but lacks the TEMPO payload. It is noteworthy, therefore, that XJB-5-133 (FIG. 5F) did not afford protection from the development of ileal mucosal hyperpermeability.

Ineffective as well were the two other hemigramicidin-based compounds that also lacked the TEMPO payload, XJB-5-127 (FIG. 5D) and XJB-5-194 (FIG. 5H). Of the compounds screened, XJB-5-131 (FIG. 5E) appeared to be the most effective, reducing hemorrhagic shock-induced mucosal hyperpermeability to approximately 60% of the control value.

Based upon the results as reflected in FIGS. 5A-5H, both the TEMPO payload and the "anchoring" hemigramicidin fragment are requisite moieties that should be present in order for effective electron scavenging activity by the XJB-5-131 compound. Accordingly, it was found that XJB-5-131 ameliorates peroxidation of mitochondrial phosopholipids (i.e., ROS activity) in gut mucosa from rats subject to hemorrhagic shock.

In the subsequent series of in vivo studies, the affect of intraluminal XJB-5-131 on hemorrhage-induced peroxidation of phospholipids in intestinal mucosa was examined. Isolated segments of the ileum of rats were divided into a series of well-vascularized components in a manner akin to sausage and the lumen of each ileal compartment was filled with the same volume of test solution containing either vehicle or a 10 µM solution of XJB-5-131, which was previously indicated to be the most active of the hemigramicidin-TEMPO conjugates. In a preferred embodiment, 0.3 mL of test solution filled the lumen of each ileal compartment.

After two hours of HS, samples of ileal mucosa from the gut sacs filled with the vehicle and XJB-5-131 were obtained and compared with ileal mucosa of normal MECs. All samples were assayed with caspase 3 or caspase 7 activity as well as the peroxidation of phosphatidylcholine ("PC"), phosphatidylethanolamine ("PE"), phosphatidylserine ("PS"), and cardiolipin ("CL"), summarized in FIG. 7.

As can be seen in FIGS. 7A-7D, treatment with XJB-5-131 significantly ameliorated hemorrhage-induced peroxidation of CL, the only phospholipid tested found in mitochondria.

However, treatment with XJB-5-131 only had a small effect on PE peroxidation and no effect on peroxidation of PC and PS. Based upon these trends, hemorrhagic shock is associated with substantial oxidative stress even in the absence of resuscitation. Further, this data also establishes that XJB-5-131 is an effective ROS scavenger as it localizes predominantly in mitochondria and protects CL from peroxidation.

Figure 8:
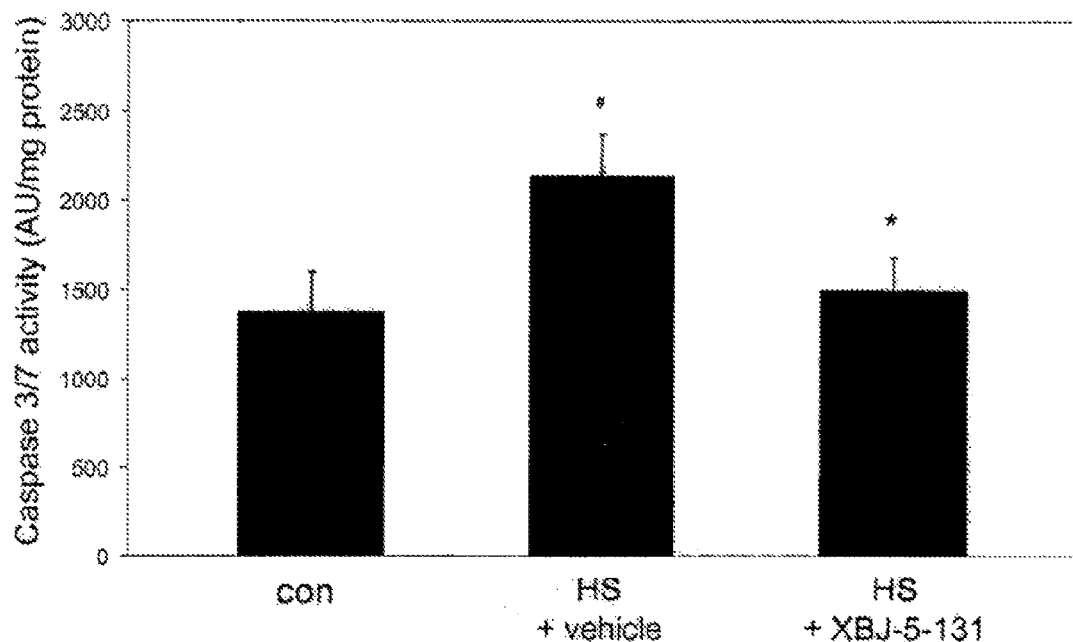
FIG. 8 is a graphical representation of caspase 3 and 7 activity that illustrates the effects of intraluminal XJB-5-131.

Relative to the activity measured in samples from normal animals, the activity of caspases 3 and 7 was markedly increased in vehicle-treated mucosal samples from hemorrhaged rats (FIG. 8). However, when the ileal segments were filled with XJB-5-131 solution instead of its vehicle, the level of caspase 3 and 7 activity after hemorrhagic shock was significantly decreased. Accordingly, hemorrhagic shock is associated with activation of pro-apoptotic pathways in gut mucosal cells. Moreover, the data support the view that this process is significantly ameliorated following mitochondrial treatment with XJB-5-131.

EZAMPLE 4

In another series of experiments, monolayers of enterocyte-like cells, Caco-$2_{BBe}$, were studied for physiological and pathophysiological purposes for determining intestinal barrier function. Just as with the prior Examples with respect to ROS exposure, the permeability of Caco-$2_{BB}$, monolayers increases when the cells are incubated with the ROS, hydrogen peroxide, or menadione (a redox-cycling quinine that promotes the formation of superoxide anion radicals).

Figure 9:
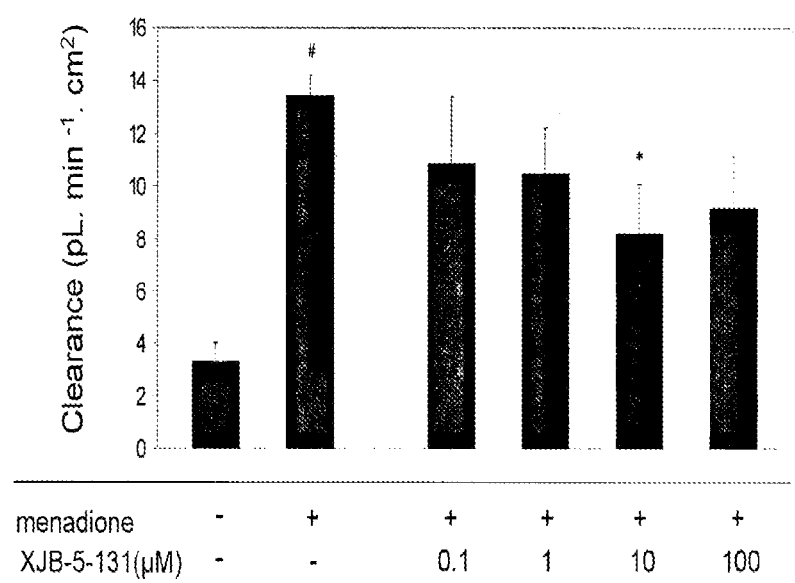
FIG. 9 is a graphical representation of permeability of XJB-5-131 with respect to Caco-2$_{BBe}$ human enterocyte-like monolayers subjected to oxidative stress. The permeability of the monolayers is expressed as a clearance ($pL \cdot h^{-1} \cdot cm^2$).

Due to the results with respect to XJB-5-131 and its amelioration of hemorrhage-induced CL peroxidation in mucosal cells in vivo (see aforementioned Examples I and II), a possible treatment using XJB-5-131 was investigated to determine if menadione-induced epithelial hyperpermeability could be ameliorated in vitro. Consistent with the prior in vivo observations, Caco-$2_{BB}$, monolayers were incubated in the absence and in the presence of menadione, respectively. After 6 hours, incubation of Caco-$2_{BB}$, monolayers with menadione caused a marked increase in the apical-basolateral clearance of FD4 (FIG. 9). Treatment with 10 µM XJB-5-131 provided significant protection against menadione-induced hyperpermeability.

EXAMPLE 5

As reflected by the above in vivo and in vitro studies, XJB-5-131 had significantly beneficial effects on several biochemical and physiological read-outs. Accordingly, systemic administration of XJB-5-131 was investigated with respect to whether it would prolong survival of patients subjected to profound periods of hemorrhagic shock with massive blood loss in the absence of standard resuscitation with blood and crystalloid solution. As in the above studies, rats were utilized as test patients.

A total of sixteen rats were tested in this study. Rats were treated with 2.8 ml/kg of vehicle or the same volume of XJB-5-131 solution during the final 20 min of the bleeding protocol. The total dose of XJB-5-131 infused was 2 µmol/kg. Following profound hemorrhagic shock consistent with the protocol described above for the prior studies, thirteen survived for at least 60 min and received the full dose of either XJB-5-131 solution or the vehicle, a 33:67 (v/v) mixture of DMSO and normal saline. As shown in Table 2, blood glucose, lactate and hemoglobin concentrations were similar in both groups at baseline and before and immediately after treatment. None of the between-group differences were statistically significant.

TABLE 2

| Parameter | Compound | Baseline | End of first phase of hemorrhage | End of second phase of hemorrhage |
|---|---|---|---|---|
| Blood glucose concentration (mg/dL) | Vehicle | 143 ± 5 | 255 ± 30 | 219 ± 26 |
| | XJB-5-131 | 134 ± 4 | 228 ± 24 | 201 ± 38 |
| Blood lactate concentration (mEq/L) | Vehicle | 1.8 ± 0.4 | 606 ± 0.8 | 5.9 ± 1.3 |
| | XJB-5-131 | 1.8 ± 0.2 | 5.7 ± 0.8 | 5.6 ± 1.2 |
| Blood Hb concentration (g/dL) | Vehicle | 12.7 ± 0.5 | 11.1 ± 0.3 | 9.4 ± 0.2 |
| | XJB-5-131 | 12.7 ± 0.3 | 10.7 ± 0.3 | 9.4 ± 0.3 |

Figure 10A:
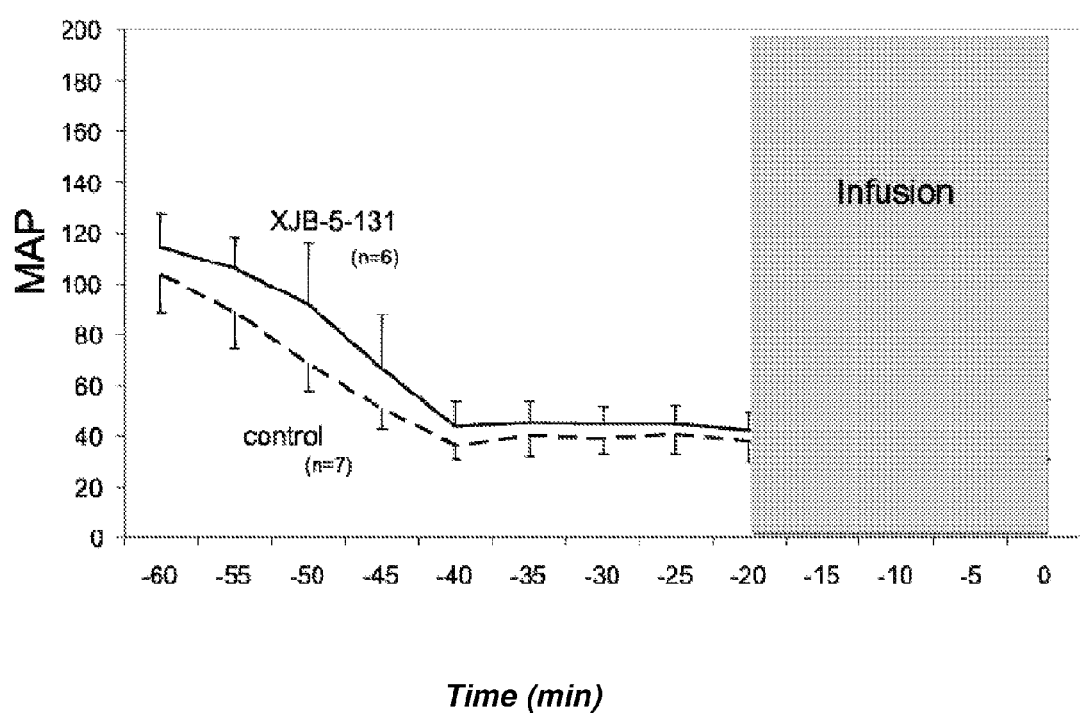
FIG. 10A is a graphical representation of the effects of intravenous treatment with XJB-5-131 on MAP (mean arterial pressure, mm Hg) of rates subjected to volume controlled hemorrhagic shock.
Figure 10B:
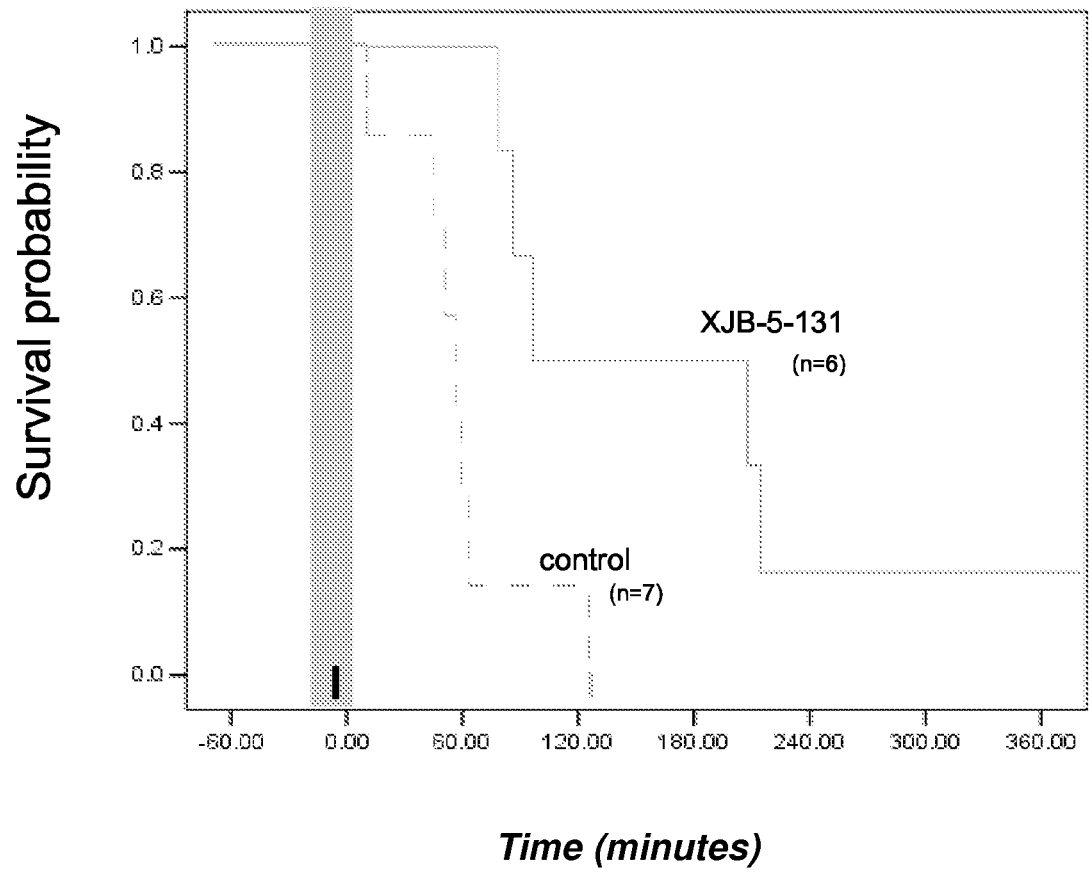
FIG. 10B is a graphical representation of the effects of intravenous treatment with XJB-5-131 on survival probability of rates subjected to volume controlled hemorrhagic shock.

Shortly after treatment was started, mean arterial pressure ("MAP") increased slightly in both groups (see FIG. 10A). In both groups, mean arterial pressure ("MAP") decreased precipitously during the first phase of the hemorrhage protocol and remained nearly constant at 40 mm Hg during the beginning of the second phase. Six of the seven animals in the vehicle-treated (control) group died within one hour of the end of the bleeding protocol and all were dead within 125 minutes (FIG. 10B). Rats treated with intravenous XJB-5-131 survived significantly longer than those treated with the vehicle. Three of the six rats survived longer than 3 hours after completion of the hemorrhage protocol; one rat survived the whole 6 hour post-bleeding observation period (FIG. 10B).

Accordingly, analysis of the XJB-5-131 studies indicate that exposure of the patient to the compound prolongs the period of time that patients can survive after losing large quantities of blood due to traumatic injuries or other catastrophes (e.g., rupture of an abdominal aortic aneurysm).

By extending the treatment window before irreversible shock develops, treatment in the field with XJB-5-131 might "buy" enough time to allow transport of more badly injured patients to locations where definitive care, including control of bleeding and resuscitation with blood products and non-sanguineous fluids, can be provided. The results using a rodent model of hemorrhagic shock also open up the possibility that drugs like XJB-5-131 might be beneficial in other conditions associated with marked tissue hypoperfusion, such as stroke and myocardial infarction.

The results presented here also support the general concept that mitochondrial targeting of ROS scavengers is a reasonable therapeutic strategy. Although previous studies have shown that treatment with TEMPOL is beneficial in rodent HS situations, a relatively large dose of the compound was required (30 mg/kg bolus+30 mg/kg per h). In contrast, treatment with a dose of XJB-5-131 that was about 300 fold smaller (~0.1 mg/kg) was clearly beneficial. The greater potency of XJB-5-131 as compared to TEMPOL presumably reflects the tendency of XJB-5-131 to localize in mitochondrial membranes, a key embodiment of the invention. As indicated above, two hemigramicidin-4-amino-TEMPO conjugates (namely XJB-5-208 and XJB-5-131, see FIG. 2) are concentrated in the mitochondria of cultures mouse embryonic cells following incubation with solutions of the compounds.

Further, the use of XJB-5-131 significantly prolonged the survival of the rats subjected to massive blood loss, even though the animals were not resuscitated with either blood or other non-sanguineous fluids and they remained profoundly hypotensive.

In light of the above, synthetic hemigramicidin peptidyl-TEMPO conjugates permeate through the cell membrane and also the mitochondrial membrane where they act as free radical scavengers for ROS such as, but not limited to, superoxide anion radicals. The conjugates are then reduced within the mitochondria by electron-transport proteins which are involved with the cellular respiration pathway, thereby coupling the decoupled ROS species. These conjugates also have the advantage, as discussed above, of being anti-apoptotic, especially in the case of compounds such as 5a and 5b.

By effectively reducing the amount of ROS species, a patient's condition, including an illness or other medical condition, may be ameliorated and, in some cases, survival may be prolonged as described above. Examples of such conditions, including diseases and other medical conditions, include (but are not limited to) the following medical conditions which include diseases and conditions: myocardial ischemia and reperfusion (e.g., after angioplasty and stenting for management of unstable angina or myocardial infarction), solid organ (lung liver, kidney, pancreas, intestine, heart) transplantation, hemorrhagic shock, septic shock, stroke, tissue damage due to ionizing radiation, lung injury, acute respiratory distress syndrome (ARDS), necrotizing pancreatitis, and necrotizing enterocolitis.

EXAMPLE 6

In a further embodiment, in support of the inter-changeability of cargoes of the mitochondria-targeting groups, a composition for scavenging radicals in a mitochondrial membrane is provided comprising a radical scavenging agent or an NOS inhibitor and a membrane active peptidyl fragment having a high affinity with the mitochondrial membrane. The membrane active peptidyl fragment preferably has a property selected from the group consisting of antioxidant, radioprotective, protective, anti-apoptotic, therapeutic, ameliorative, NOS antagonist and combinations thereof. In a related embodiment, with respect to compounds with antibiotic properties, it is generally preferable to employ compounds whose mode of action includes bacterial wall targets.

In another embodiment, the membrane active compound is preferably selected from the group consisting of bacitracins, gramicidins, valinomycins, enniatins, alamethicins, beauvericin, serratomolide, sporidesmolide, tyrocidins, polymyxins, monamycins, and lissoclinum peptides.

In a related embodiment, the NOS antagonist is selected from the group consisting of XJB-5-234 (a), XJB-5-133 (b), XJB-5-241 (c), and XJB-5-127 (d), comprising AMT NOS antagonist cargos:

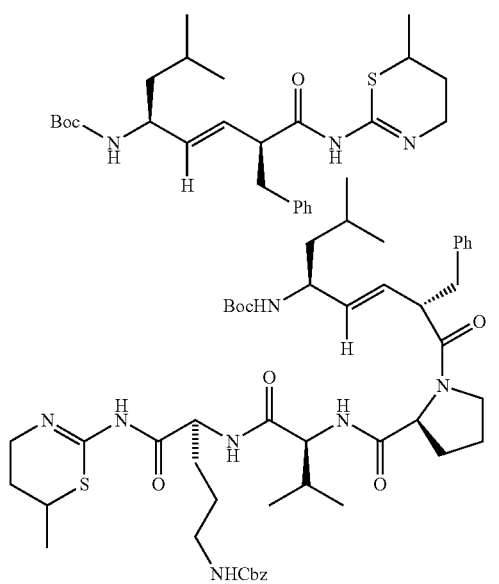

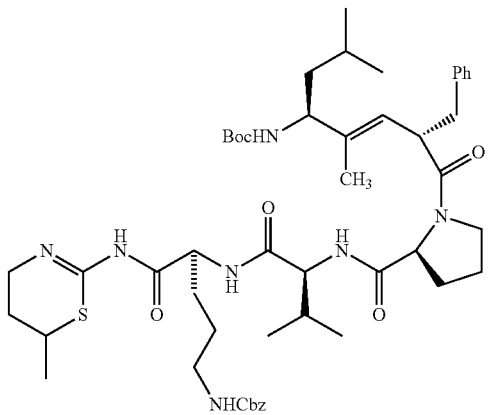

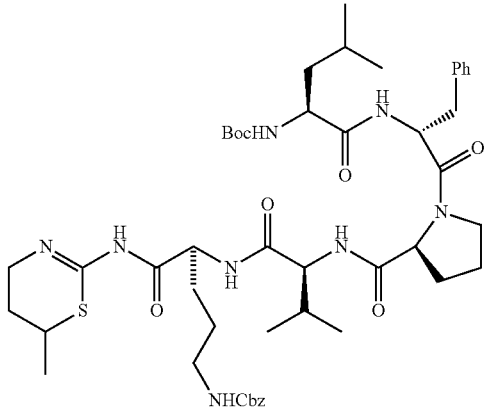

EXAMPLE 7

The following examples provide protocols for additional cargo usable in compounds described herein which serve as NOS antagonists.

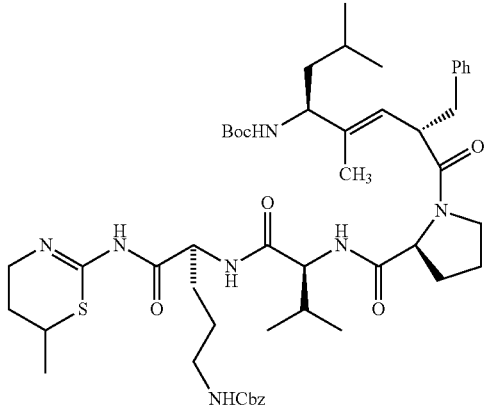

Compound (1) is Boc-Leu-104 [(E)-C(CH$_3$)=CH]-$^D$Phe-Pro-Val-Orn(Cbz)-AMT (XJB-5-241) and was prepared according to the following protocol. A solution of 11.0 mg (13.2 μmol) of Boc-Leu-ψ[(E)-C(CH$_3$)=CH]-$^D$Phe-Pro-Val-Orn(Cbz)-OMe (2-48) in 400 μL of MeOH was treated at 0° C. with 132 μL (132 μmol) of 1 N NaOH. The reaction mixture was stirred at room temperature for 8 h, and treated with 132 μL (132 μmol) of 1 N HCl. The solution was extracted with CHCl₃ and the organic layer was dried (Na₂SO₄) and concentrated in vacuo to give the crude acid as a colorless form. This acid was dissolved in 2.00 mL of CHCl₃ and treated at room temperature with 2.1 mg (16 μmol) of HOBt, 3.0 mg (16 μmol) of EDC, 3.3 mg (20 μmol) of 2-amino-5,6-dihydro-6-methyl-4H-1,3-thiazine.HCl and 3.5 mg (27 μmol) of DMAP. The reaction mixture was stirred at room temperature for 48 h, diluted with CHCl₃, and washed with H₂O. The organic layer was dried (Na₂SO₄), concentrated in vacuo, and purified by chromatography on SiO₂ (1:1, hexanes/EtOAc followed by 20:1, CHCl₃/MeOH) to yield 11 mg (89%) of XJB-5-241 as a colorless powder. The following characterization data were obtained: LC-MS (R$_t$, 8.37 min, linear gradient 70% to 95% CH₃CN(H₂O) in 10 min, 0.4 mL/min; m/z=932.4 [M+H]⁺, 954.3 [M+Na]⁺) and HRMS (ESI) m/z calculated for C₅₀H₇₄N₇O₈S (M+H) 932.5320, found 932.5318.

(2)

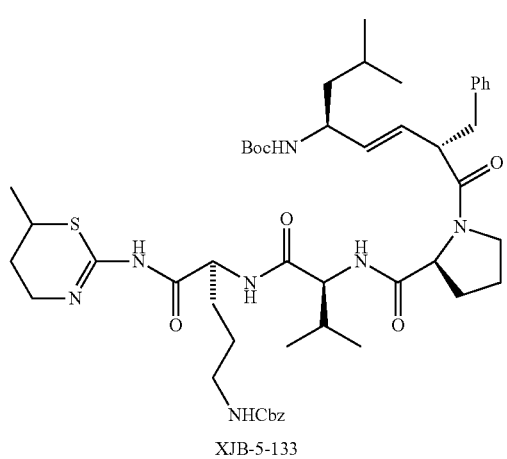

XJB-5-133

Compound (2) is Boc-Leu-ψ[(E)-CH=CH]-ᴰPhe-Pro-Val-Orn(Cbz)-AMT (XJB-5-133) and was prepared according to the following protocol. A solution of 20.0 mg (24.3 μmol) of 2-85 (XJB-5-194) in 800 μL of MeOH was treated at 0° C. with 243 mL (243 μmol) of 1 N NaOH. The reaction mixture was stirred at room temperature for 6 h, and treated with 243 μL (243 μmol) of 1 N HCl. The solution was extracted with CHCl₃ and the organic layer was dried (Na₂SO₄) and concentrated in vacuo to give the crude acid as a colorless form. This acid was dissolved in 1.00 mL of CHCl₃ and treated at room temperature with 3.9 mg (29 μmol) of HOBt, 5.6 mg (29 μmol) of EDC, 6.1 mg (37 μmol) of 2-amino-5,6-dihydro-6-methyl-4H-1,3-thiazine.HCl and 7.4 mg (61 μmol) of DMAP. The reaction mixture was stirred at room temperature for 20 h, diluted with CHCl₃, and washed with H₂O. The organic layer was dried (Na₂SO₄), concentrated in vacuo, and purified by chromatography on SiO₂ (1:1, hexanes/EtOAc followed by 20:1, CHCl₃/MeOH) and an additional preparative C₁₈ reverse phase HPLC purification was performed: 80% to 100% CH₃CN(H₂O) in 20 min, 5.0 mL/min) to afford 12.9 mg (58%) of XJB-5-133 as a colorless powder. The following characterization data were obtained: LC-MS (R$_t$, 7.89 min, linear gradient 70% to 95% CH₃CN (H₂O) in 10 min, 0.4 mL/min; m/z=918.3 [M+H]⁺, 940.3 [M+Na]⁺) and HRMS (ESI) m/z calculated for C₄₉H₇₂N₇O₈S (M+H) 918.5163, found 918.5185.

(3)

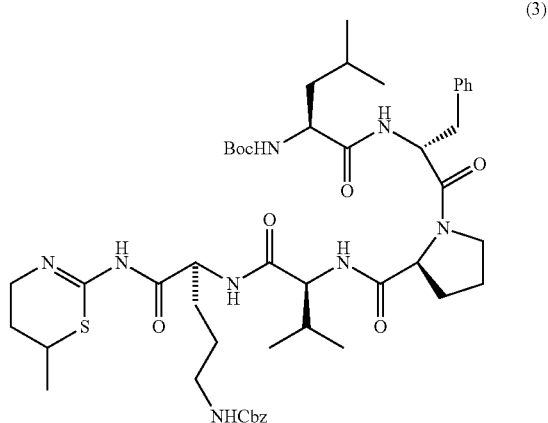 [SMILES: CC(C)C[C@H](NC(=O)OC(C)(C)C)C(=O)N[C@H](Cc1ccccc1)C(=O)N1CCC[C@H]1C(=O)N[C@H](C(=O)N[C@@H](CCCNC(=O)OCc1ccccc1)C(=O)NC1=NCCC(C)S1)C(C)C]

Compound (3) is Boc-Leu-ᴰPhe-Pro-Val-Orn(Cbz)-AMT (XJB-5-127). According to the following protocol. A solution of 24.0 mg (28.7 μmol) of Boc-Leu-ᴰPhe-Pro-Val-Orn(Cbz)-OMe in 800 μL of MeOH was treated at room temperature with 287 μL (287 μmol) of 1 N NaOH. The reaction mixture was stirred at room temperature for 5 h, and treated at 0° C. with 287 μL (287 μmol) of 1 N HCl. The solution was extracted with CHCl₃ and the organic layer was dried (Na₂SO₄) and concentrated in vacuo to give the crude acid as a colorless foam. The crude acid was dissolved in 2.00 mL of CHCl₃ and treated at room temperature with 4.6 mg (34 μmol) of HOBt, 6.6 mg (34 μmol) of EDC, 5.7 mg (34 μmol) of 2-amino-5,6-dihydro-6-methyl-4H-1,3-thiazine.HCl and 8.8 mg (72.0 μmol) of DMAP. The reaction mixture was stirred at room temperature for 24 h, diluted with CHCl₃, and washed with H₂O. The organic layer was dried (Na₂SO₄), concentrated in vacuo, and purified by chromatography on SiO₂ (2:1, hexanes/EtOAc followed by 20:1, CHCl₃/MeOH) to yield 17.0 mg (63%) of XJB-5-127 as a colorless powder. The following characterization data were obtained: LC-MS (R$_t$ 6.32 min, linear gradient 70% to 95% CH₃CN(H₂O) in 10 min, 0.4 mL/min; m/z=935.3 [M+H]⁺, 957.3 [M+Na]⁺) and HRMS (ESI) m/z calculated for C₄₈H₇₁N₈O₉S (M+H) 935.5065, found 935.5044.

(4)

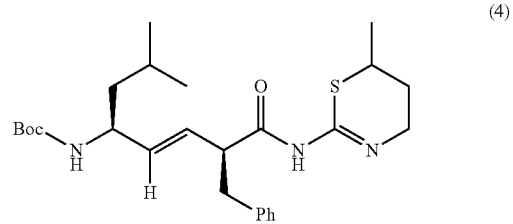 [SMILES: CC(C)C[C@@H](/C=C/[C@H](Cc1ccccc1)C(=O)NC1=NCCC(C)S1)NC(=O)OC(C)(C)C]

Compound (4) is Boc-Leu-ψ[(E)-CH=CH]-ᴰPhe-AMT (XJB-5-234). A solution of crude Boc-Leu-w[(E)-CH=CH]-ᴰPhe-OH (2-84) (30.5 μmol) in 2.00 mL of CH₂Cl₂ was treated at 0° C. with 6.1 mg (37 μmol) of 2-amino-5,6-dihydro-6-methyl-4H-1,3-thiazine.HCl, 7.0 mg (37 μmol) of EDC, 4.9 mg (37 μmol) of HOBt, and 9.3 mg (76 μmol) of DMAP. The reaction mixture was stirred at room temperature overnight, concentrated in vacuo, and purified by chromatography on SiO₂ (2:1, CH₂Cl₂/EtOAc) to yield 9.1 mg (63%) of XJB-5-234 as a colorless foam. The following characterization data were obtained: LC-MS (R$_t$ 8.42 min, linear gradient 70% to 95% CH₃CN(H₂O) in 10 min, 0.4 mL/min;

m/z=474.5 [M+H]$^+$) and HRMS (ESI) m/z calculated for C$_{26}$H$_{40}$N$_3$O$_3$S (M+H) 474.2790, found 474.2781.

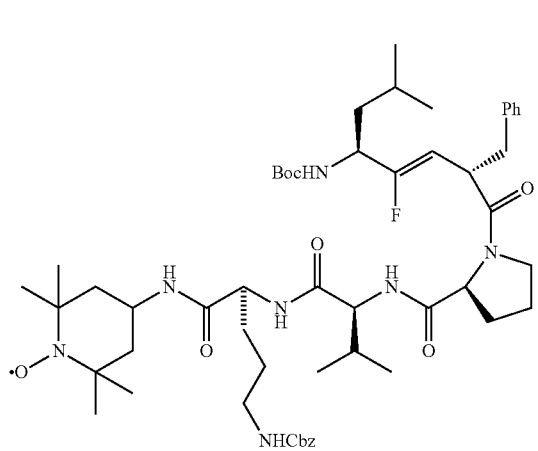

(5)

Compound (5) is Boc-Leu-ψ[(Z)-CF=CH]-$^D$Phe-Pro-Val-Orn(Cbz)-TEMPO (XJB-7-53). A solution of 3.4 mg (4.1 μmol) of Boc-Leu-ψ[(Z)-CF=CH]$^D$Phe-Pro-Val-Orn(Cbz)-OMe XJB-5-66) in 400 μL of MeOH was treated at 0° C. with 41 μL (41 μmol) of 1 N NaOH. The reaction mixture was stirred at room temperature for 12 h, and treated with 41 μL (41 μmol) of 1 N HCl. The solution was extracted with CHCl$_3$ and the organic layer was dried (Na$_2$SO$_4$) and concentrated in vacuo to give the crude acid as a colorless form. This acid was dissolved in 400 μL of CHCl$_3$ and treated at room temperature with 0.7 mg (5 μmol) of HOBt, 0.9 mg (5 μmol) of EDC, 0.5 mg (4 μmol) of 4-amino-TEMPO and 1.1 mg (6 μmol) of DMAP. The reaction mixture was stirred at room temperature for 12 h, diluted with CHCl$_3$, and washed with H$_2$O. The organic layer was dried (Na$_2$SO$_4$), concentrated in vacuo, and purified by chromatography on SiO$_2$ (1:1, hexanes/EtOAc followed by 20:1, CHCl$_3$/MeOH) to yield 3.6 mg (91%) of XJB-7-53 as a colorless powder. The following characterization data were obtained: LC-MS (R$_t$ 8.45 min, linear gradient 70% to 95% CH$_3$CN(H$_2$O) in 10 min, 0.4 mL/min; m/z=977.5 [M+H]$^+$, 999.5 [M+Na]$^+$) and HRMS (ESI) m/z calculated for C$_{53}$H$_{79}$FN$_7$O$_9$Na (M+Na) 999.5821.

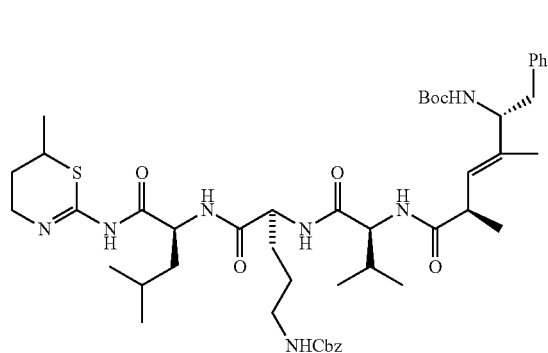

(6)

Compound (6) is Boc-$^D$Phe-ψ[(E)-C(CH$_3$)=CH]-Ala-Val-Orn(Cbz)-Leu-AMT (XJB-7-42) and was prepared according to the following protocol. A solution of 4.5 mg (5.6 μmol) of Boc-$^D$Phe-ψ[(E)-C(CH$_3$)=CH]-Ala-Val-Orn(Cbz)-Leu-OMe (2-119) in 0.35 mL of MeOH was treated at 0° C. with 56 μL (56 μmol) of 1 N NaOH. The reaction mixture was stirred at room temperature for 12 h, and treated with 56 μL (56 μmol) of 1 N HCl. The solution was extracted with CHCl$_3$ and the organic layer was dried (Na$_2$SO$_4$) and concentrated in vacuo to give the crude acid as a colorless form. This acid was dissolved in 0.80 mL of CHCl$_3$ and treated at room temperature with 0.9 mg (6.7 μmol) of HOBt, 1.3 mg (6.7 μmol) of EDC, 1.4 mg (8.4 μmol) of 2-amino-5,6-dihydro-6-methyl-4H-1,3-thiazine.HCl and 1.7 mg (14 μmol) of DMAP. The reaction mixture was stirred at room temperature for 36 h, concentrated in vacuo, and purified by chromatography on Sift (20:1, CHCl$_3$/MeOH) to yield 5.0 mg (99%) of XJB-7-42 as a colorless foam. The following characterization data were obtained: LC-MS (R$_t$ 6.61 min, linear gradient 70% to 95% CH$_3$CN(H$_2$O) in 10 min, 0.4 mL/min; m/z=907.3 [M+H]$^+$, 929.4 [M+Na]$^+$) and HRMS (ESI) m/z calculated for C$_{48}$H$_{72}$N$_7$O$_8$S (M+H) 906.5163, found 906.5190.

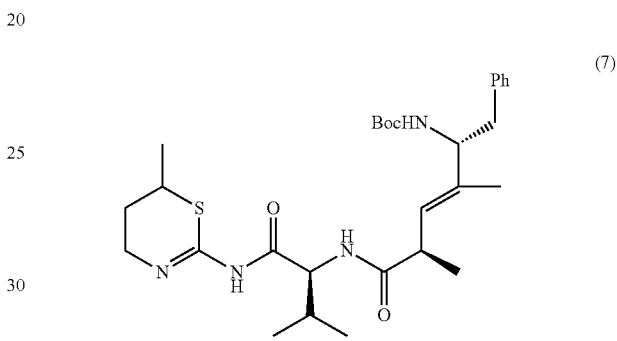

(7)

Compound (7) is Boc-$^D$Phe-ψ[(E)-C(CH$_3$)=CH]-Ala-Val-AMT (XJB-7-43). A solution of 14.3 μmol of crude Boc-$^D$Phe-ψ[(E)-C(CH$_3$)=CH]-Ala-Val-OMe (2-111) in 1.00 mL of CHCl$_3$ was treated at room temperature with 2.3 mg (17 μmol) of HOBt, 3.3 mg (17 μmol) of EDC, 3.6 mg (22 μmol) of 2-amino-5,6-dihydro-6-methyl-4H-1,3-thiazine-.HCl and 4.4 mg (36 μmol) of DMAP. The reaction mixture was stirred at room temperature for 36 h, concentrated in vacuo, and purified by chromatography on SiO$_2$ (20:1, CHCl$_3$/MeOH) to yield 7.5 mg (96%) of XJB-7-43 as a colorless foam. The following characterization data were obtained: LC-MS (R$_t$ 5.41 min, linear gradient 70% to 95% CH$_3$CN(H$_2$O) in 10 min, 0.4 mL/min; m/z=545.3 [M+H]$^+$, 567.3 [M+Na]$^+$) and HRMS (ESI) m/z calculated for C$_{29}$H$_{44}$N$_4$O$_4$S (M+Na) 567.2981, found 567.2971.

Among the preferred radical scavenging agents are a material selected from the group consisting of a ubiquinone analog, a ubiquinone analog fragment moiety, a ubiquinone analog fragment moiety lacking a hydrophilic tail, a superoxide dismutase mimetic, a superoxide dismutase biomimetic or a salen-manganese compound.

As is known to one ordinarily skilled in the art, ionizing radiation activates a mitochondrial nitric oxide synthase ("mtNOS"), leading to inhibition of the respiratory chain, generation of excess superoxide radicals, peroxynitrite production and nitrosative damage. The damage done by ionizing radiation is believed to be alleviated. The composition of this embodiment is characterized by the property of inhibiting mtNOS, thereby resisting generation of excess superoxide radicals, peroxynitrite and nitrosative damage.

Protection again irradiation damage using systemic drug delivery can result in unwanted side effects. One approach to limit or prevent these adverse side effects is to target drug delivery to the mitochondria using a peptide carrier strategy.

In one embodiment, a potent NOS inhibitor, the non-arginine analog of 2-amino-6-methyl-thiazine ("A M T"), was selected as a cargo. Irradiation of the ureopithelium results in increased production of superoxide and nitric oxide ("NO"), mouse bladders were instilled with AMT or 4-amino-TEMPO to determine if inhibition of NO or scavenging free radicals is more radioprotective.

An unconjugated and conjugated NOS antagonist, (AMT, 100 μM) and an unconjugated and conjugated nitroxide derivative (4-amino-TEMPO, 100 μM) were incubated for two hours at 37° C. with 32D c13 hemopoietic cells.

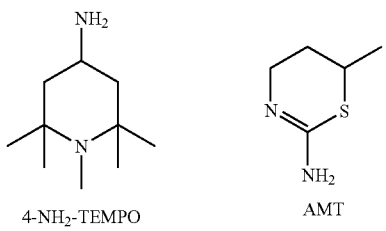

4-NH$_2$-TEMPO     AMT

Following incubation, the cells were lysed and the mitochondria isolated for a mass spectrometry analysis where compounds isolated from mitochondria were identified as Na+ adducts. The resulting spectra (not shown) demonstrate that 4-amino-TEMPO only permeate the mitochondrial membrane with the assistance of the attached GS-derived targeting sequence. Further spectra (not shown) indicate that unconjugated AMT do not enter the mitochondria membrane in substantial quantities. Thus, the targeting peptides successfully direct a NOS antagonist and a nitroxide to the mitochondria.

Further physiological studies were conducted to determine the effects of peptide-targeted AMT and 4-amino-TEMPO on NO and peroxynitrite production in irradiated uroepithelial cells. The cells were cultured in an 8-well slide chamber for 3 days and then microsensor measurements were taken 24 hours after irradiation.

In untreated irradiated cells and cells treated with unconjugated 4-amino-TEMPO (100 μM) or unconjugated AMT (10 μM), capsaicin evoked NO production and resulted in the formation of comparable amount of peroxynitrite. In cells treated with high-dose conjugated 4-amin-TEMPO (100 μM), peroxynitrite production was decreased by approximately 4-fold. In non-radiated cells or cells treated with conjugated AMT (10 μM), NO induced peroxynitrite formation was nearly completely inhibited. This suggested that peptides conjugates couple or covalently link with membrane impermeant 4-amino-TEMPO or AMT and facilitate the transport of 4-amin-TEMPO across the mitochondrial membrane. Furthermore, this data suggests that the peptide conjugates do not interfere with the NOS inhibitory activity of AMT or the free radical scavenging activity of 4-amino-TEMPO and that AMT is a more effective radioprotectant [Kanai, A. J. et al., Mitochondrial Targeting of Radioprotectants Using Peptidyl Conjugates, ORGANIC AND BIOMOLECULAR CHEMISTRY (in press)].

Quantitative mass spectrometry studies were used to compare the effectiveness of several AMT peptide conjugates in permeating the mitochondrial membrane, specifically XJB-5-234, XJB-5-133, XJB-5-241, and XJB-5-127. The Fmole/10 μM mitochondrial protein ratio provides a relative quantification of conjugate concentration at the target site. Table 3 indicates that the most efficacious conjugate was compound XJB-5-241.

TABLE 3

| Compound | Fmole/1 0 M mitochondrial protein |
|---|---|
| XJB-5-234 | 1.45 |
| XJB-5-133 | 89.8 |
| XJB-5-241 | 103.3 |

The trisubstituted (E)-alkene moiety embedded in XJB-5-241 has a stronger conformational effect that the less biologically active disubstituted (E)-alkene XJB-5-133 or the GS peptidyl fragment XJB-5-127. The data indicates that a defined secondary structure and an appropriate conformational preorganization is important in accomplishing mitochondrial permeation of compounds that reduce nitrosative and oxidative effects.

The presence of a non-hydrolyzable alkene isostere functions in place of labile peptide bonds and is significant for a prolonged mechanism of action. The relatively rigid (E)-alkenes (ψ[(E)-C(R)=CH]) represent useful, conformationally preorganized structural mimetics and have been used as surrogates of hydrolytically labile amide bonds in a number of enzyme inhibitors. The primary objective of this strategy is the accurate mimicry of the geometry of the peptide bond; however, (E)-alkenes also modulate the physicochemical properties, solubility, and lipophilicity, number of hydrogen donors and acceptors, etc, of the parent structures, and therefore generally have a different metabolic fate than simple peptides.

A targeted delivery strategy employed in this invention is advantageous since some neuronal NOS (nNOS) antagonists and most antioxidants, including nitroxide derivatives, are poorly cell-permeable and require therapeutically effective concentrations greater than 100 μM if used without a conjugate.

The method related to this embodiment of the invention delivers a composition to mitochondria comprising transporting to said mitochondria a desired cargo which may, for example, be (a) a radical scavenging agent by use of a membrane active peptidyl fragment preferably having has a β-turn motif having a high affinity for the mitochondrial membrane or (b) a nitric oxide synthase antagonist bonded to the membrane active peptidyl fragment.

EZAMPLE 8

Figure 11A:
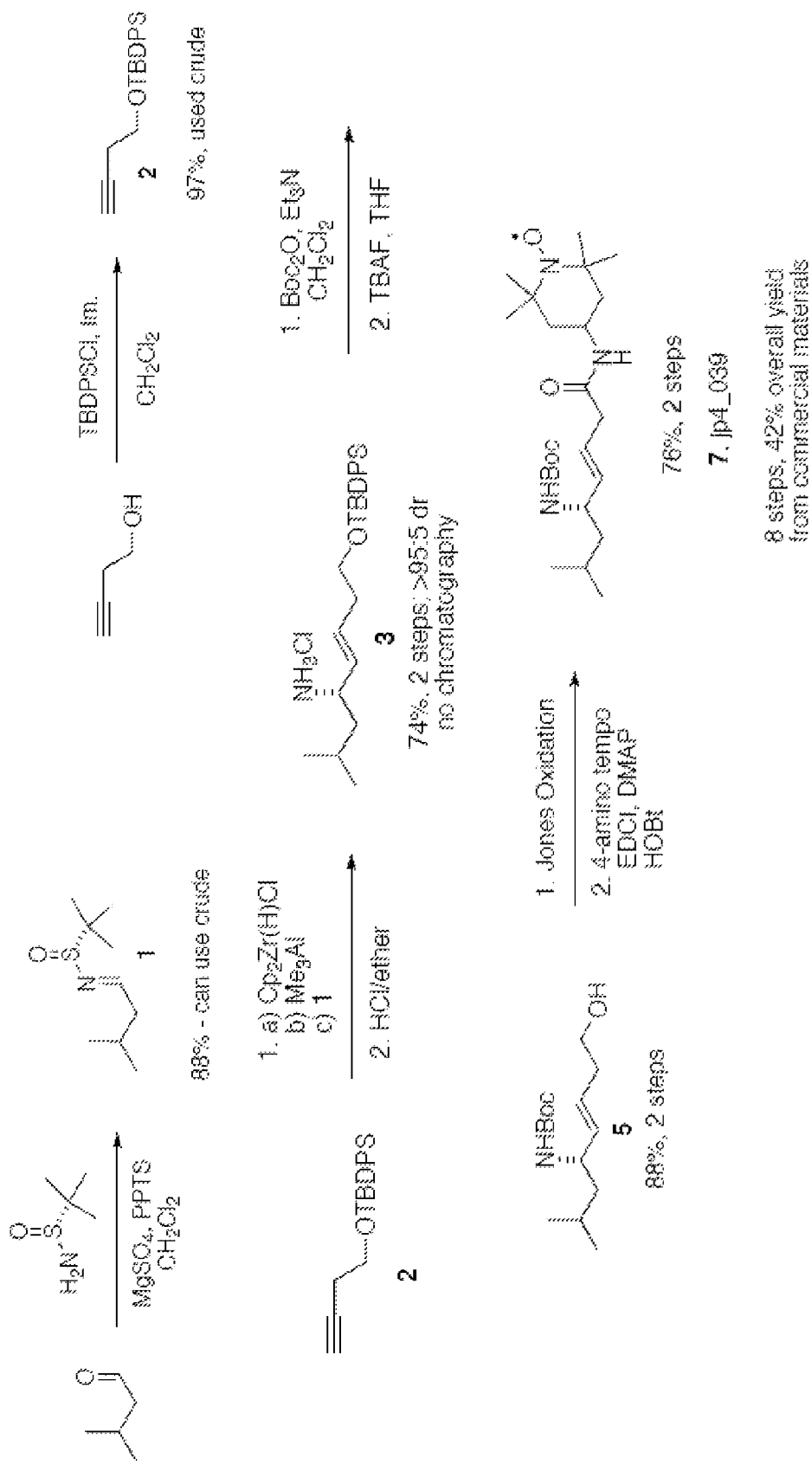
FIG. 11A is a schematic of a synthesis protocol for JP4-039, FIG. 11B provides a synthesis route for a compound of Formula 3, below.
Figure 11B:
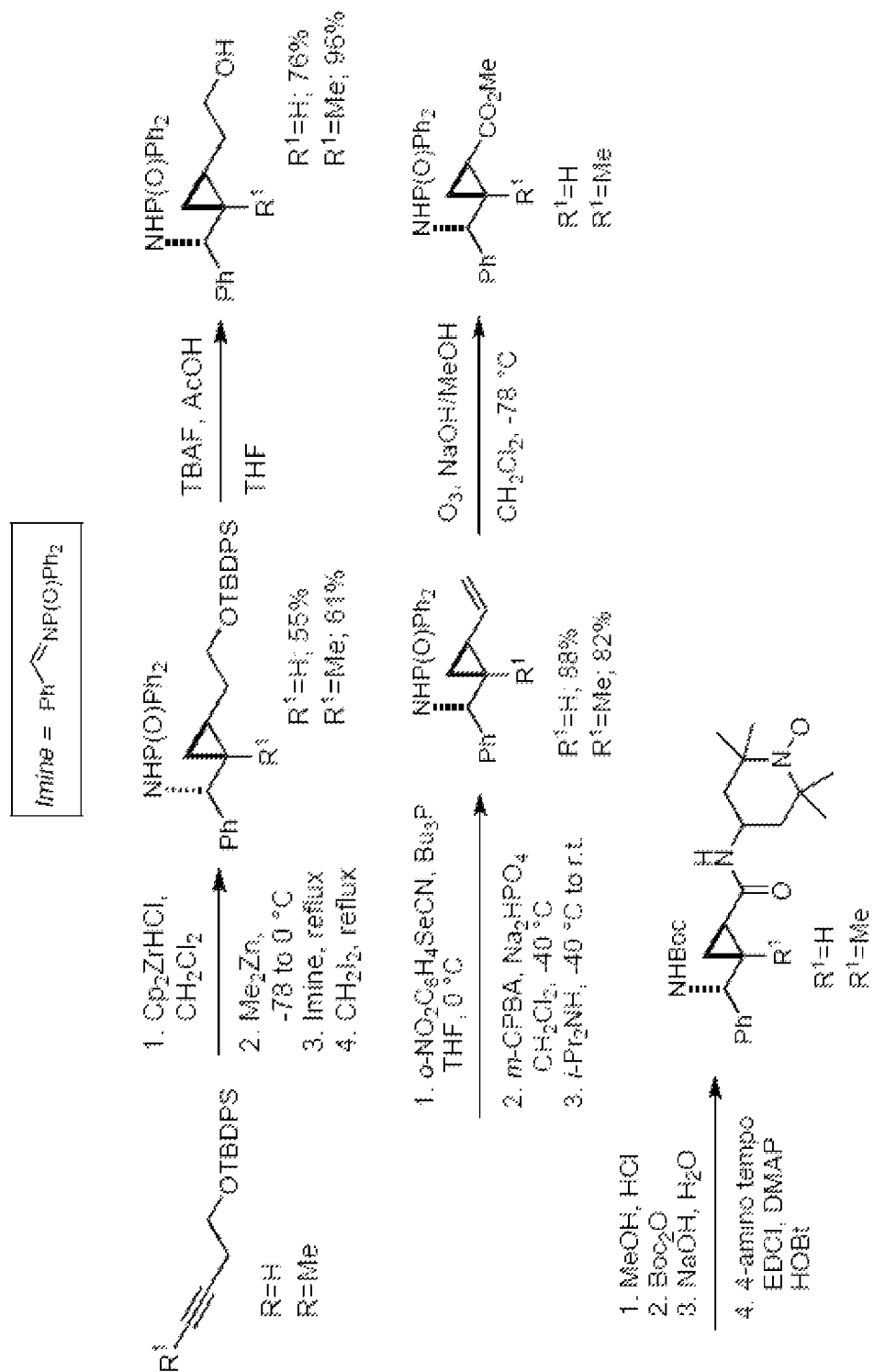

Synthesis of JP4-039 (see FIG. 11)

Synthesis of JP4-039 was accomplished according to the following.

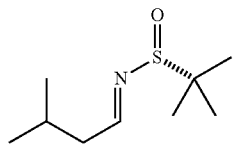

1

(R,E)-2-Methyl-N-(3-methylbutylidene)propane-2-sulfinamide (1) (Staas, D. D.; Savage, K. L.; Homnick, C. F.; Tsou, N.; Ball, R. G. *J. Org. Chem.*, 2002, 67, 8276)—To a solution of isovaleraldehyde (3-Methylbutyraldehyde, 5.41 mL, 48.5 mmol) in CH$_2$Cl$_2$ (250 mL) was added (R)-2-methylpropane-2-sulfinamide (5.00 g, 40.4 mmol), MgSO$_4$ (5.0 eq, 24.3 g, 202 mmol) and PPTS (10 mol %, 1.05 g, 4.04 mmol) and the resulting suspension was stirred at RT (room temperature, approximately 25° C.) for 24 h. The reaction was filtered through a pad of Celite® and the crude residue was purified by chromatography on SiO$_2$ (3:7, EtOAc:hexanes) to yield 6.75 g (88%) as a colorless oil. $^1$H NMR δ 8.07 (t, 1 H, J=5.2 Hz), 2.47-2.38 (m, 2 H), 2.18-1.90 (m, 1 H), 1.21 (s, 9 H), 1.00 (d, 6 H, J=6.7 Hz). As an alternative, filtration through a pad of SiO$_2$ provides crude imine that functions equally well in subsequent reactions.

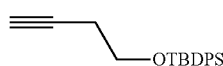

2

(But-3-ynyloxy)(tert-butyl)diphenylsilane (2) (Nicolaou, K. C.; Lizos, D. E.; Kim, D. W.; Schlawe, D.; deNoronha, R. G.; Longbottom, D. A.; Rodriquez, M.; Bucci, M.; Cirino, G. J. Am. Chem. Soc. 2006, 128, 4460)—To a solution of 3-butyn-1-ol (5.00 g, 71.3 mmol) in CH$_2$Cl$_2$ (400 mL) was added imidazole (5.40 g, 78.5 mmol) and TBDPSCl ((tert-butyl)diphenylsilane chloride)(22.0 g, 78.5 mmol) and the reaction was stirred at RT for 22 h. The reaction was filtered through a pad a SiO$_2$, the SiO$_2$ washed with CH$_2$Cl$_2$ and the colorless solution concentrated to yield 21.4 g (97%) of crude alkyne that was carried on without further purification.

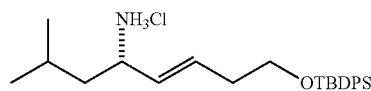

3

(S,E)-8-(tent-Butyldiphenylsilyloxy)-2-methyloct-5-en-4-amine hydrochloride (3)—To a solution of (2) (15.9 g, 51.5 mmol) in CH$_2$Cl$_2$ (300 mL) was added zirconocene hydrochloride (15.1 g, 58.4 mmol) in 3 portions and the resulting suspension was stirred at RT for 10 min. The resulting yellow solution was cooled to 0° C. and Me$_3$Al (2.0 M in hexanes, 27.5 mL, 54.9 mmol) was added and stirred for 5 minutes followed by addition of a solution of imine (1) (6.50 g, 34.3 mmol) in CH$_2$Cl$_2$ (50 mL) and the orange solution was stirred for an additional 4 h while allowed to warm to rt. The reaction was quenched with MeOH, diluted with H$_2$O and CH$_2$Cl$_2$ and HCl (1 M) was added to break up the emulsion (prolonged stirring with Rochelle's salt can also be utilized). The organic layer was separated and the aqueous layer was washed with CH$_2$Cl$_2$ (2×). The organic layers were combined, washed with brine, dried (MgSO4), filtered though a pad of Celite® and concentrated. Since the crude oil was contaminated with metal salts, the oil was dissolved in Et$_2$O (diethyl ether, Et=ethyl), allowed to sit for 2 h, and then filtered though a pad of Celite® and concentrated. Analysis of the crude residue by 1H NMR showed only 1 diastereomer (>95:5 dr).

To the crude residue in Et$_2$O (800 mL) was added HCl (4.0 M in dioxane, 17.2 mL, 68.7 mmol) and the reaction was stirred for 30 minutes, during which time a white precipitate formed. The precipitate was filtered, washed with dry Et$_2$O, and dried to afford 11.0 g (74% over 2 steps) of (3) as a colorless solid: $[α]_D$ −2.9 (c 1.0, CH2Cl2); $^1$H NMR δ 8.42 (bs, 3 H), 7.70-7.55 (m, 4 H), 7.48-7.30 (m, 6 H), 5.90 (dt, 1 H, J=14.9, 7.5 Hz), 5.52 (dd, 1 H, J=15.4, 8.4 Hz), 3.69 (appt, 3 H, J=6.5 Hz), 2.45-2.20 (m, 2 H), 1.80-1.50 (m, 3 H), 1.03 (s, 9 H), 0.95-0.84 (m, 6 H); $^{13}$C NMR δ 135.5, 134.5, 133.7, 129.5, 127.6, 127.3, 63.0, 52.9, 42.1, 35.6, 26.7, 24.4, 22.9, 21.5, 19.1; EIMS m/z 395 ([M−HCl]$^+$, 40), 338 (86), 198 (100); HRMS (EI) m/z calcd for C$_{25}$H$_{37}$NOSi (M−HCl) 395.2644, found 395.2640.

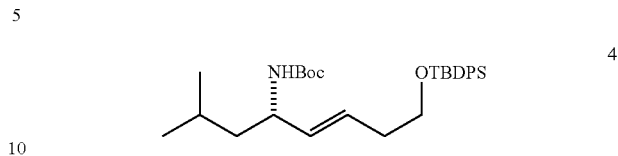

4

(S,E)-tert-Butyl 8-(tert-butyldiphenylsilyloxy)-2-methyloct-5-en-4-ylcarbamate (4)—To a solution of (3) (10.5 g, 24.3 mmol) in CH$_2$Cl$_2$ (400 mL) was added Et$_3$N (triethylamine) (3.0 eq, 10.3 mL, 72.9 mmol) and Boc$_2$O (1.05 eq, 5.74 g, 25.5 mmol) and the resulting suspension was stirred at RT for 14 h. The reaction was quenched with sat. aq. NH$_4$Cl, the organic layers separated, dried (MgSO$_4$), filtered and concentrated. The crude residue was carried onto the next step without further purification.

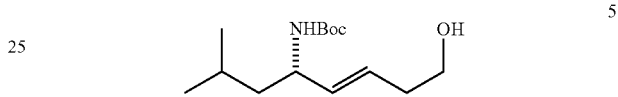

5

(S,E)-tert-Butyl 8-hydroxy-2-methyloct-5-en-4-ylcarbamate (5)—To a solution of crude (4) (12.0 g, 24.3 mmol) in THF (200 mL) at 0° C. was added TBAF (1.0 M in THF, 1.25 eq, 30.4 mL, 30.4 mmol) and the reaction was warmed to RT and stirred for 2 h. The reaction was quenched with sat. aq. NH$_4$Cl, organic layer washed with brine, dried (MgSO$_4$), filtered and concentrated. The crude residue was purified by chromatography on SiO$_2$ (3:7, EtOAc:hexanes) to yield 5.51 g (88%, 2 steps) as a colorless oil. $[α]_D$ −12.7 (c 1.0, CH$_2$Cl$_2$); $^1$H NMR δ 8.08 (t, 1 H, J=4.1 Hz), 7.40-7.15 (m, 20 H), 4.79-4.41 (m, 8 H), 4.05-3.95 (m, 3 H), 3.89-3.79 (m, 1 H), 3.79-3.70 (m, 2 H), 3.70-3.61 (m, 1 H), 2.70-2.52 (m, 1 H), 2.50-2.36 (m, 1 H), 2.04-1.80 (m, 2 H); $^{13}$C NMR δ 168.7, 138.1, 138.0, 137.9, 137.8, 128.0, 128.0, 127.9, 127.6, 127.5, 127.4, 127.2, 127.2, 127.1, 76.2, 73.8, 72.8, 72.8, 72.6, 72.1, 69.9, 67.1, 56.0, 32.1, 22.9, 21.9; EIMS m/z 257 ([M]$^+$, 10), 227 (55), 171 (65); HRMS (EI) m/z calcd for C$_{14}$H$_{27}$NO$_3$ 257.1991, found 257.1994.

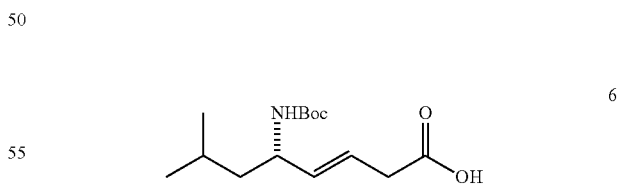

6

(S,E)-5-(tert-Butoxycarbonylamino)-7-methyloct-3-enoic acid (6)—To a solution of (5) (1.00 g, 3.89 mmol) in acetone (40 mL) at 0° C. was added a freshly prepared solution of Jones Reagent (2.5 M, 3.89 mL, 9.71 mmol) and the reaction was stirred at 0° C. for 1 h. The dark solution was extracted with Et$_2$O (3×50 mL), the organic layers washed with water (2×75 mL), brine (1×50 mL), dried (Na$_2$SO$_4$), filtered and concentrated to yield 990 mg (94% crude) of acid (6) as a yellow oil that was used without further purification.

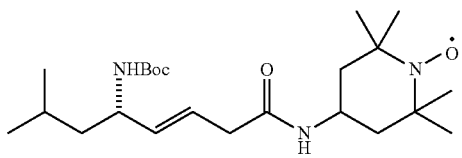

(S,E)-5-(tert-Butoxycarbonylamino)-7-methyloct-3-enoic acid-TEMPO (7)—To a solution of (6) (678 mg, 2.50 mmol, crude) in $CH_2Cl_2$ (35 mL) at 0° C. was added 4-amino tempo (1.5 eq, 662 mg, 3.75 mmol), EDCI (1.2 eq, 575 mg, 3.00 mmol), DMAP (1.1 eq, 339 mg, 2.75 mmol) and HOBt-hydrate (1.1 eq, 377 mg, 2.75 mmol) and the resulting orange solution was stirred at RT for 14 h. The reaction was diluted with $CH_2Cl_2$, washed with sat. aq. $NH_4Cl$ and the organic layer dried ($Na_2SO_4$), filtered and concentrated. The crude residue was purified by chromatography on $SiO_2$ (1:1 to 2:1, EtOAc/hexanes) to yield 857 mg (76%, 2 steps) as a peach colored solid. Compound purity determined by LCMS and $^1H$ NMR.

Figure 12:
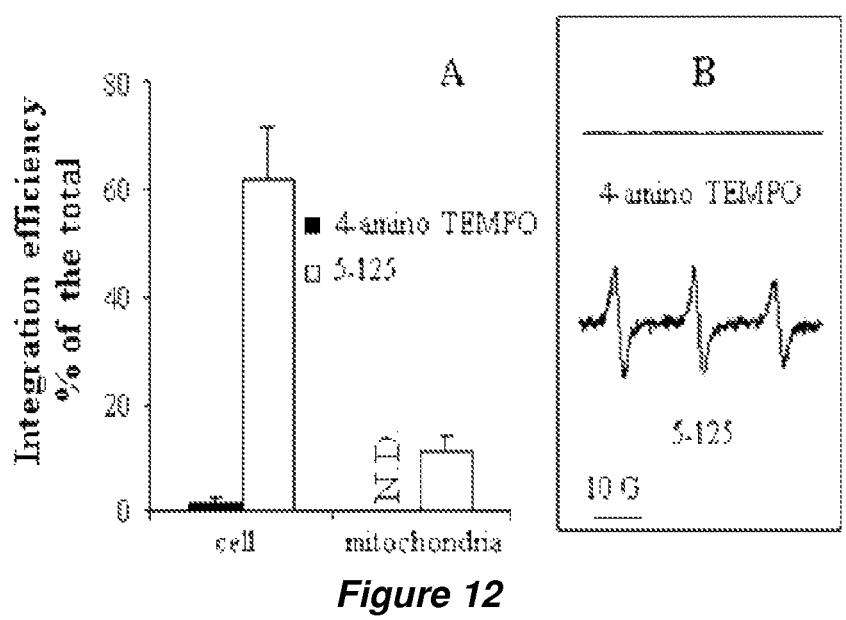
FIG. 12. shows that nitroxide conjugate XJB-5-125 integrates into cells and mitochondria much more efficiently than their parent non-conjugated 4-amino-TEMPO in mouse embryonic cells. (A) shows their cellular and mitochondrial integration efficiencies in mouse embryonic cells, and (B) shows representative EPR spectrum of nitroxides recovered from mitochondria.

The compounds shown as Formula 3, above can be synthesized as shown in FIG. 12 HERE

EXAMPLE 9

A Mitochondria-Targeted Nitroxide/Hemigramicidin S Conjugate Protects Mouse Embryonic Cells Against Gamma Irradiation
(see, Jiang, J, et al., *Int. J. Radiation Oncology Biol. Phys.*, Vol. 70, No. 3, pp. 816-825, 2008)
EPR-based Analysis of Integration and Distribution of Nitroxides.

To compare the integration efficiency, mouse embryonic cells ($1 \times 10^7$/mL) were incubated with 10 µM nitroxides for 10 min. ESR spectra of nitroxide radicals in the incubation medium, cell suspension or mitochondrial suspension were recorded after mixing with acetonitrile (1:1 v/v) after 5-min incubation with 2 mM $K_3Fe(CN)_6$ using JEOL-RE1X EPR spectrometer under the following conditions: 3350 G center field; 25 G scan range; 0.79 G field modulation, 20 mW microwave power; 0.1 s time constant; 4 min scan time. Integration efficiency was calculated as $(E_{initial} - E_{medium})/E_{initial} \times 100\%$. Mitochondria were isolated using a mitochondria isolation kit (Pierce, Rockford, Ill.) according to the manufacturer's instruction. Amounts of nitroxide radicals integrated into mitochondria were normalized to the content of cytochrome c oxidase subunit IV.
Superoxide Generation.

Oxidation-dependent fluorogenic dye, DHE was used to evaluate intracellular production of superoxide radicals. DHE is cell permeable and, in the presence of superoxide, is oxidized to fluorescent ethidium which intercalates into DNA. Briefly, cells were treated with 5 µM DHE for 30 min at the end of incubation. Cells were then collected by trypsinization and resuspended in PBS. The fluorescence of ethidium was measured using a FACScan flow cytometer (Becton-Dickinson, Rutherford, N.J.) supplied with the CellQuest software. Mean fluorescence intensity from 10,000 cells was acquired using a 585/42 nm bandpass filter.
CL Oxidation.

CL hydroperoxides were determined by fluorescence HPLC of products formed in MP-11-catalyzed reaction with a fluorogenic substrate, Amplex Red. Oxidized phospholipids were hydrolyzed by pancreatic phospholipase $A_2$ (2 U/ml) in 25 mM phosphate buffer containing 1 mM $CaCl_2$, 0.5 mM EDTA and 0.5 mM SDS (pH 8.0 at RT for 30 min) After that Amplex Red and MP-11 were added and samples were incubated for 40 min at 4° C. Shimadzu LC-100AT vp HPLC system equipped with fluorescence detector (RF-10Axl, Ex/Em=560/590 nm) and autosampler (SIL-10AD vp) were used for the analysis of products separated by HPLC (Eclipse XDB-C18 column, 5 µm, 150×4.6 mm) Mobile phase was composed of $NaH_2PO_4$ (25 mM, pH 7.0)/methanol (60:40 v/v).
Phosphatidylserine (PS) Externalization.

Externalization of PS was analyzed by flow cytometry using annexin-V kit. Briefly, harvested cells were stained with annexin-V-FITC and PI for 5 min in dark prior to flow cytometry analysis. Ten thousand events were collected on a FACScan flow cytometer (Becton-Dickinson) supplied with CellQuest software.
Gamma-irradiation Dose Survival Curves of Mouse Embryonic Cells.

Cells were plated in 35-mm Petri dishes with 2 ml culture medium at a density between 100 and 1000 cells per dish. Cells were treated with GS-nitroxide (XJB-5-125) either before (10-min) or after (1-h) γ-irradiation. XJB-5-125 was removed from the medium 4-h post-irradiation. Colonies were fixed and stained with 0.25% crystal violet and 10% formalin (35% v/v) in 80% methanol for 30 min after a 9-day incubation period, and those of ≥50 cells were counted as survivors. The surviving fraction was calculated as the plating efficiency of the samples relative to that of the control.

FIG. 12 shows that nitroxide conjugate XJB-5-125 integrates into cells and mitochondria much more efficiently than their parent non-conjugated 4-amino-TEMPO in mouse embryonic cells. (A) shows their cellular and mitochondrial integration efficiencies in mouse embryonic cells, and (B) shows representative EPR spectrum of nitroxides recovered from mitochondria.

Figure 13:
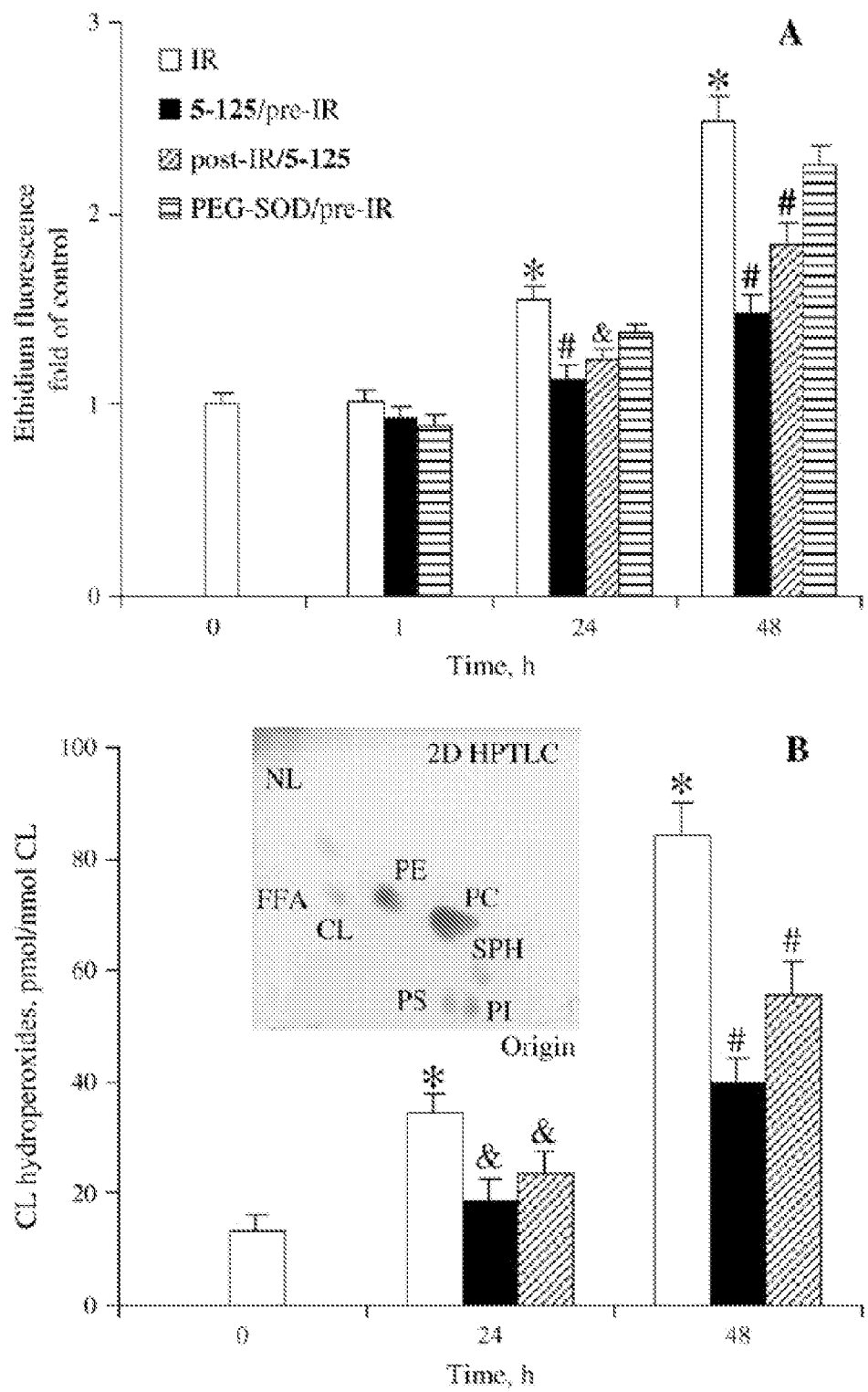
FIG. 13. reveals that nitroxide conjugate XJB-5-125 protects mouse embryonic cells against gamma irradiation induced superoxide generation and cardiolipin peroxidation. (A) superoxide generation. Cells were exposed to 10 Gy of γ-irradiation. XJB-5-125 (20 μM) was added to cells either 10-min before or 1-h after irradiation and removed after 5-h incubation. Cells were incubated with 5 μM DHE for 30 min at the indicated time points. Ethidium fluorescence was analyzed using a FACScan flow cytometer supplied with CellQuest software. Mean fluorescence intensity from 10,000 cells was acquired using a 585-nm bandpass filter. (B) Cardiolipin oxidation. Cardiolipin hydroperoxides were determined using a fluorescent HPLC-based Amplex Red assay. Data presented are means±S.E. (n=3). *$p<0.01$ vs non-irradiated cells; *$p<0.01(0.05)$ vs irradiated cells without XJB-5-125 treatment under the same condition. Insert is a typical 2D-HPTLC profile of phospholipids from cells.

FIG. 13 reveals that nitroxide conjugate XJB-5-125 protects mouse embryonic cells against gamma irradiation induced superoxide generation and cardiolipin peroxidation. (A) superoxide generation. Cells were exposed to 10 Gy of γ-irradiation. XJB-5-125 (20 µM) was added to cells either 10-min before or 1-h after irradiation and removed after 5-h incubation. Cells were incubated with 5 µM DHE for 30 min at the indicated time points. Ethidium fluorescence was analyzed using a FACScan flow cytometer supplied with CellQuest software. Mean fluorescence intensity from 10,000 cells was acquired using a 585-nm bandpass filter. (B) Cardiolipin oxidation. Cardiolipin hydroperoxides were determined using a fluorescent HPLC-based Amplex Red assay. Data presented are means±S.E. (n=3). *p<0.01 vs non-irradiated cells; *p<0.01(0.05) vs irradiated cells without XJB-5-125 treatment under the same condition. Insert is a typical 2D-HPTLC profile of phospholipids from cells.

Figure 14:
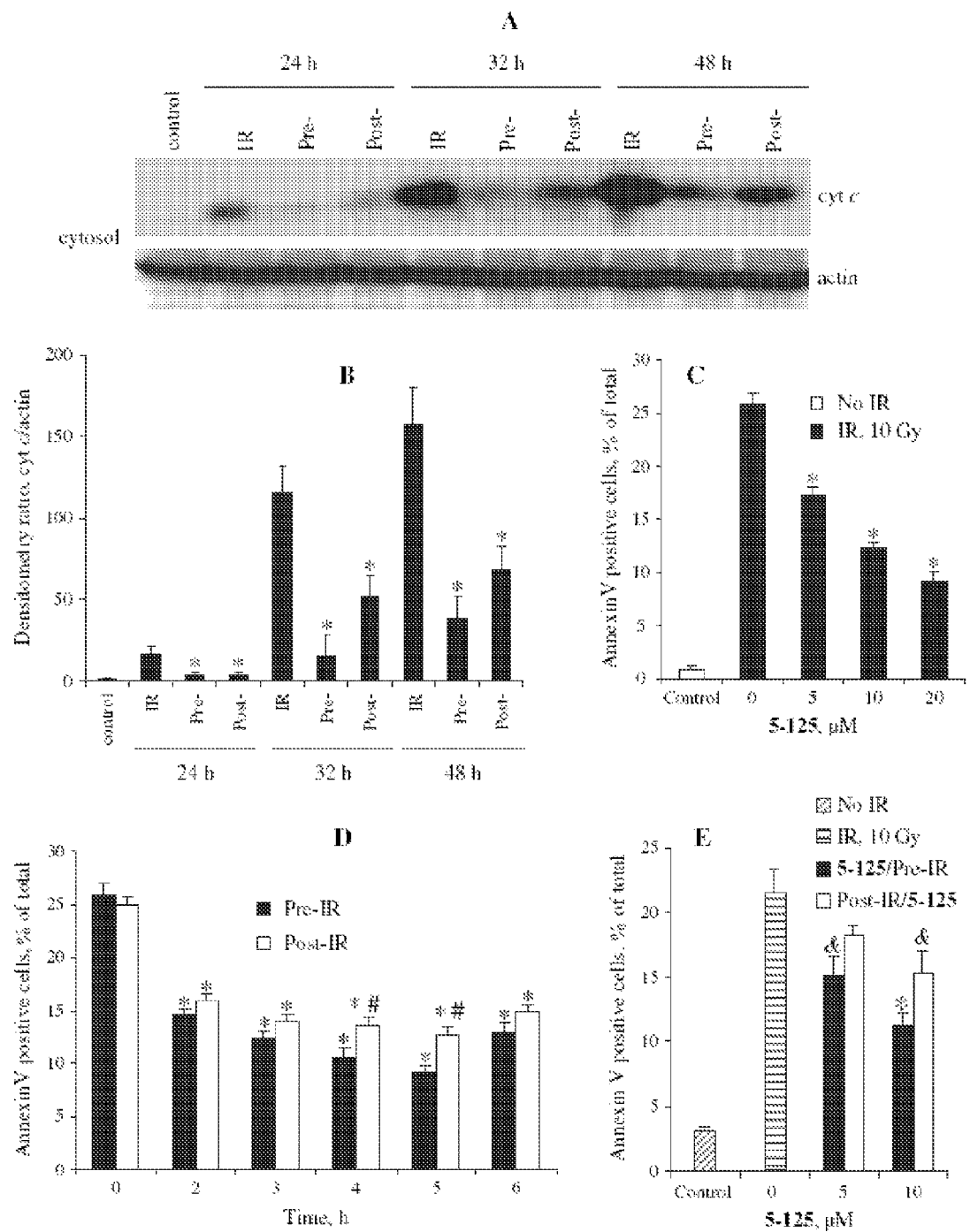
FIG. 14. reveals that nitroxide conjugate XJB-5-125 protects cells against gamma irradiation induced apoptosis. (A) XJB-5-125 blocks γ-irradiation induced accumulation of cytochrome c in the cytosol of mouse embryonic cells. (B) Densitometry ratio of cytochrome c/actin. Semi-quantitation of the bands was carried out by densitometry using Labworks Image Acquisition and Analysis Software (UVP, Upland, Calif.). The level of cytochrome c release was expressed as the mean densitometry ratio of cytochrome c over actin. (C) Dose (5, 10 and 20 μM) dependent radioprotective effect of XJB-5-125 (pre-treatment) on γ-irradiation (10 Gy) induced phosphatidylserine (PS) externalization. After 48 h post-irradiation incubation, cells were harvested and stained with annexin-V-FITC and propodium iodide (PI) prior to flow cytometry analysis. (D) Time (2, 3, 4, 5, and 6 h) dependent radioprotective effect of XJB-5-125 (20 μM) on γ-irradiation (10 Gy) induced PS externalization (48 h post irradiation) in mouse embryonic cells. (E) Effect of XJB-5-125 on γ-irradiation (10 Gy) induced PS externalization in human bronchial epithelial cell line BEAS-2B cells. Cells were treated with 5-125 (5 or 10 μM) before (10-min) or after (I-h) irradiation. Externalization of PS was analyzed 72 h post-irradiation exposure. Data shown are means±S.E. (n=3). *(&) $p<0.01(0.05)$ vs irradiated cells without 5-125 treatment, #$p<0.05$ vs cells pre-treated with 5-125.

FIG. 14 reveals that nitroxide conjugate XJB-5-125 protects cells against gamma irradiation induced apoptosis. (A) XJB-5-125 blocks γ-irradiation induced accumulation of cytochrome c in the cytosol of mouse embryonic cells. (B) Densitometry ratio of cytochrome c/actin. Semi-quantitation of the bands was carried out by densitometry using Labworks Image Acquisition and Analysis Software (UVP, Upland, Calif.). The level of cytochrome c release was expressed as the mean densitometry ratio of cytochrome c over actin. (C) Dose (5, 10 and 20 µM) dependent radioprotective effect of XJB-5-125 (pre-treatment) on γ-irradiation (10 Gy) induced phosphatidylserine (PS) externalization. After 48 h post-irradiation incubation, cells were harvested and stained with annexin-V-FITC and propodium iodide (PI) prior to flow cytometry analysis. (D) Time (2, 3, 4, 5, and 6 h) dependent radioprotective effect of XJB-5-125 (20 µM) on γ-irradiation (10 Gy) induced PS externalization (48 h post irradiation) in mouse embryonic cells. (E) Effect of XJB-5-125 on γ-irradiation (10 Gy) induced PS externalization in human bronchial epithelial cell line BEAS-2B cells. Cells were treated with 5-125 (5 or 10 µM) before (10-min) or after (1-h) irradiation. Externalization of PS was analyzed 72 h post-irradiation exposure. Data shown are means±S.E. (n=3). *(&) p<0.01(0.05) vs irradiated cells without 5-125 treatment, #p<0.05 vs cells pre-treated with 5-125.

Figure 15:
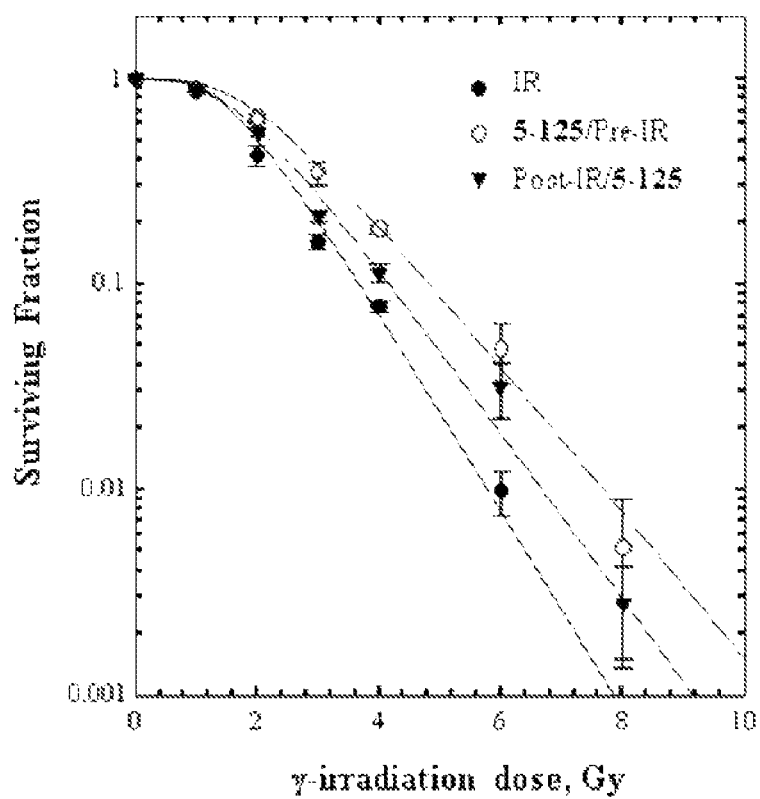
FIG. 15. shows the effect of nitroxide conjugate XJB-5-125 on gamma-irradiation dose survival curves of mouse embryonic cells. Cells were pre- (10-min) or post-treated (1-h) with XJB-5-125 (20 μM), which was removed after 4-h incubation period. The surviving fraction was calculated as the plating efficiency of the samples relative to that of the control. The data was fitted to a single-hit multitarget model using SigmaPlot 9.0 (Systat Software). Data presented are the mean±S.E. (n=3).

FIG. 15 shows the effect of nitroxide conjugate XJB-5-125 on gamma-irradiation dose survival curves of mouse embryonic cells. Cells were pre- (10-min) or post-treated (1-h) with XJB-5-125 (20 µM), which was removed after 4-h incubation period. The surviving fraction was calculated as the plating efficiency of the samples relative to that of the control. The data was fitted to a single-hit multitarget model using SigmaPlot 9.0 (Systat Software). Data presented are the mean±S.E. (n=3).

Figure 16:
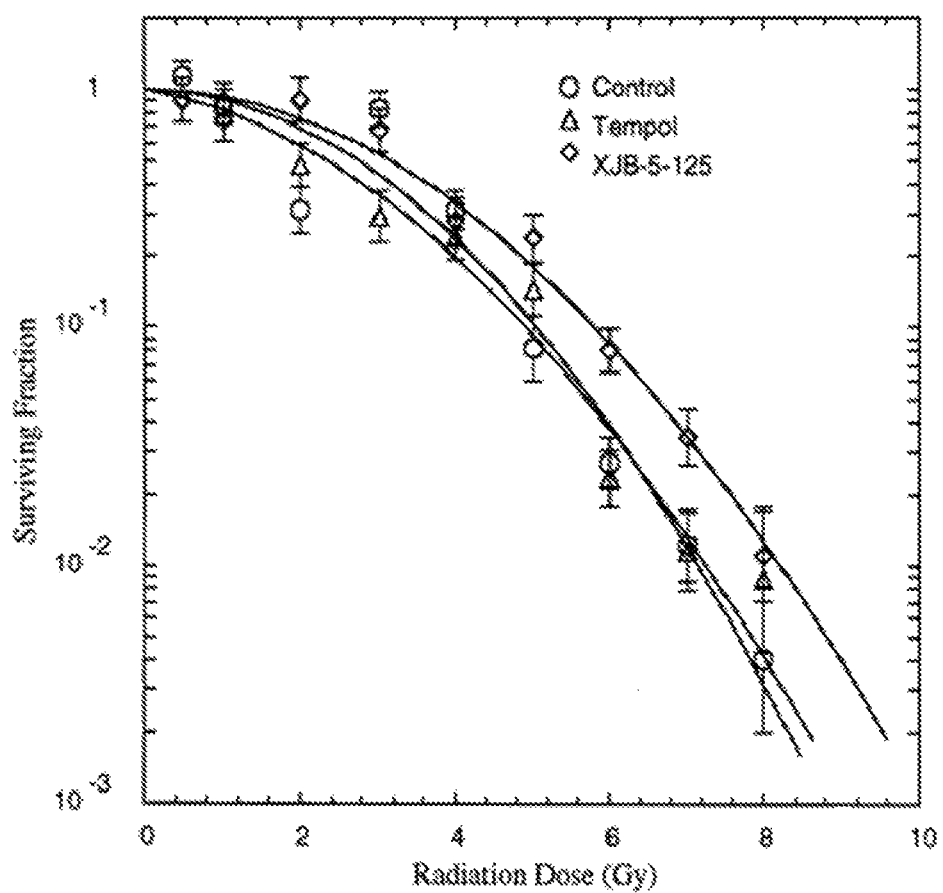
FIG. 16. illustrates the effect of GS conjugated nitroxide, XJB-5-125, on gamma-irradiation dose survival curves of 32D cl 3 murine hematopoietic cells. The cells incubated in XJB-5-125 or Tempol had an increased Do (1.138 or 1.209 Gy, respectively) compared to the 32D cl 3 cells (0.797 Gy). The cells incubated in XJB-5-125 had an increased shoulder on the survival curve with an n of 18.24 compared to 5.82 for the cells incubated in tempol.

FIG. 16 illustrates the effect of GS conjugated nitroxide, XJB-5-125, on gamma-irradiation dose survival curves of 32D cl 3 murine hematopoietic cells. The cells incubated in XJB-5-125 or Tempol had an increased Do (1.138 or 1.209 Gy, respectively) compared to the 32D cl 3 cells (0.797 Gy). The cells incubated in XJB-5-125 had an increased shoulder on the survival curve with an n of 18.24 compared to 5.82 for the cells incubated in tempol.

EZAMPLE 10

Testing of the Radioprotective Abilities of JP4-039

Figure 17:
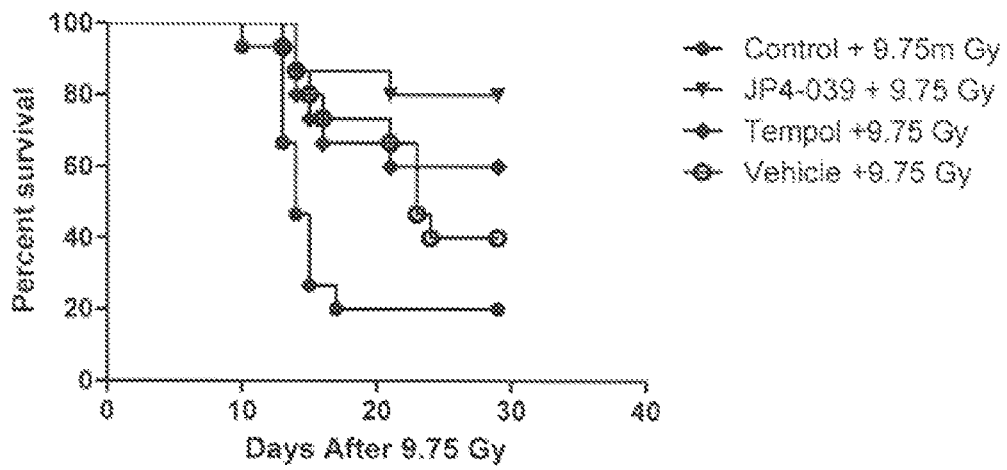
FIG. 17 is a graph showing GS-nitroxide compound JP4-039 increases survival of mice exposed to 9.75 Gy total body irradiation.

FIG. 17 is a graph showing GS-nitroxide compound JP4-039 increases survival of mice exposed to 9.75 Gy total body irradiation. Mice received intraperitoneal injection of 10 mg. per kilogram of each of the chemicals indicated in FIG. 5, then 24 hours later received 9.75 Gy total body irradiation according to published methods. Mice were followed for survival according to IACUC regulations. There was a significant increase in survival of mice receiving JP4-039 compared to irradiated control mice. (P=0.0008).

Figure 18:
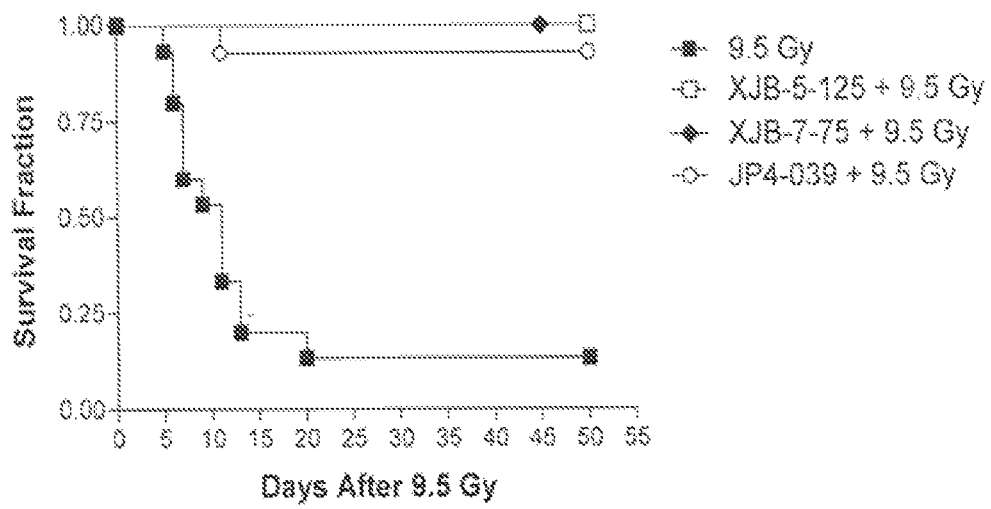
FIG. 18 is a graph showing that GS-nitroxide compound JP4-039 increases survival of mice exposed to 9.5 Gy total body irradiation.

FIG. 18 is a graph showing that GS-nitroxide compound JP4-039 increases survival of mice exposed to 9.5 Gy total body irradiation. Groups of 15 mice received intraperitoneal injection of 10 mg. per kilogram of each indicated GS-nitroxide compound or carrier (Cremphora plus alcohol at 1 to 1 ratio, then diluted 1 to 10 in distilled water). Mice received 10 mg per kilogram intra-peritoneal injection 24 hours prior to total body irradiation. Control mice received radiation alone. There was a statistically significant increase in survival in mice receiving GS-nitroxide compounds. (P=0.0005)

Figure 19:
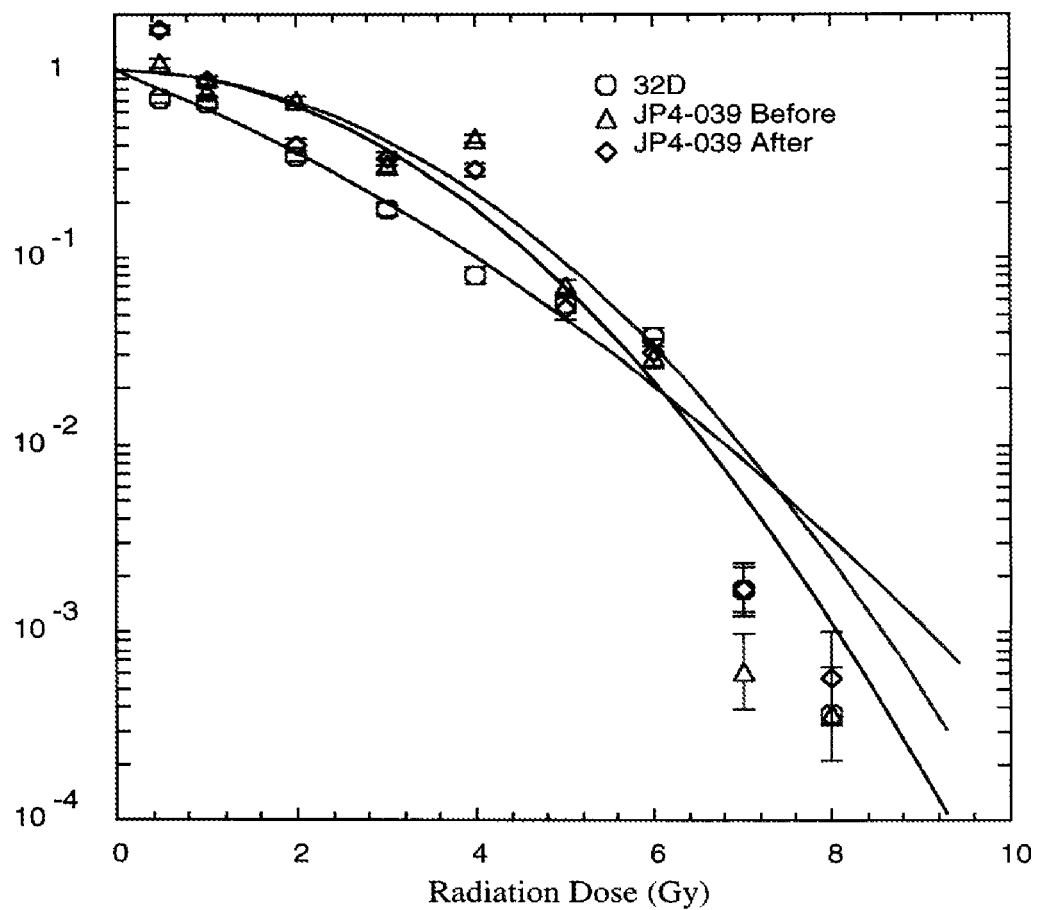
FIG. 19 is a graph showing that GS-nitroxide JP4-039 is an effective hematopoietic cell radiation mitigator when delivered 24 hr after irradiation.

FIG. 19 is a graph showing that GS-nitroxide JP4-039 is an effective hematopoietic cell radiation mitigator when delivered 24 hr after irradiation. Irradiation survival curves were performed on cells from the 32D cl 3 mouse hematopoietic progenitor cell line, incubated in 10 µM JP4-039 for 1 hour before irradiation, or plated in methycellulose containing 10 µM JP4-030 after irradiation. Cells were irradiated from 0 to 8 Gy, plated in 0.8% methycellulose containing media, and incubated for 7 days at 37° C. Colonies of greater than 50 cells were counted and data analyzed by linear quadratic and single-hit, multi-target models. Cells incubated in JP4-039 were more resistant as demonstrated by an increased shoulder on the survival curve with an ñ of 5.25±0.84 if drug was added before irradiation or 4.55±0.47 if drug was added after irradiation compared to 1.29+0.13 for 32D cl 3 cells alone (p=0.0109 or 0.0022, respectively).

Figure 20:
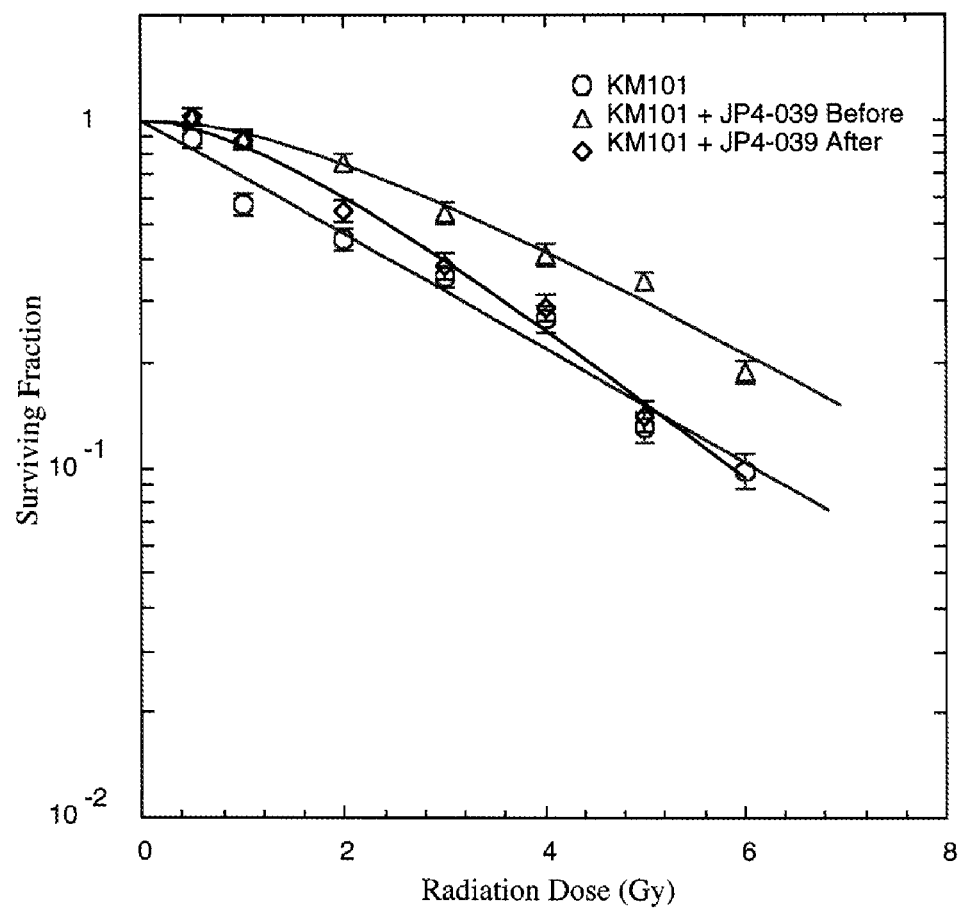
FIG. 20 is a graph showing that JP4-039 is an effective mitigator of irradiation damage to KM101 human marrow stromal cells.

FIG. 20 is a graph showing that JP4-039 is an effective mitigator of irradiation damage to KM101 human marrow stromal cells. KM101 cells were incubated in media alone or in JP4-039 (10 µM) for one hour before irradiation or 24 hours after irradiation. The cells were irradiated to doses ranging from 0 to 6 Gy and plated in 4 well plates. Seven days later the cells were stained with crystal violet and colonies of greater than 50 cells counted. Cells incubated in JP4-039 either before or after irradiation were more radioresistant as shown by an increased shoulder of n=2.3±0.2 or 2.2±0.2, respectively compared to n of 1.1±0.1for the KM101 cells (p=0.0309 or 0.0386, respectively). There was no significant change in the Do for the different conditions.

EZAMPLE 11

NOD/SCID Mouse Model to Optimize JP4-039 for a Clinical Trial

Figure 21A:
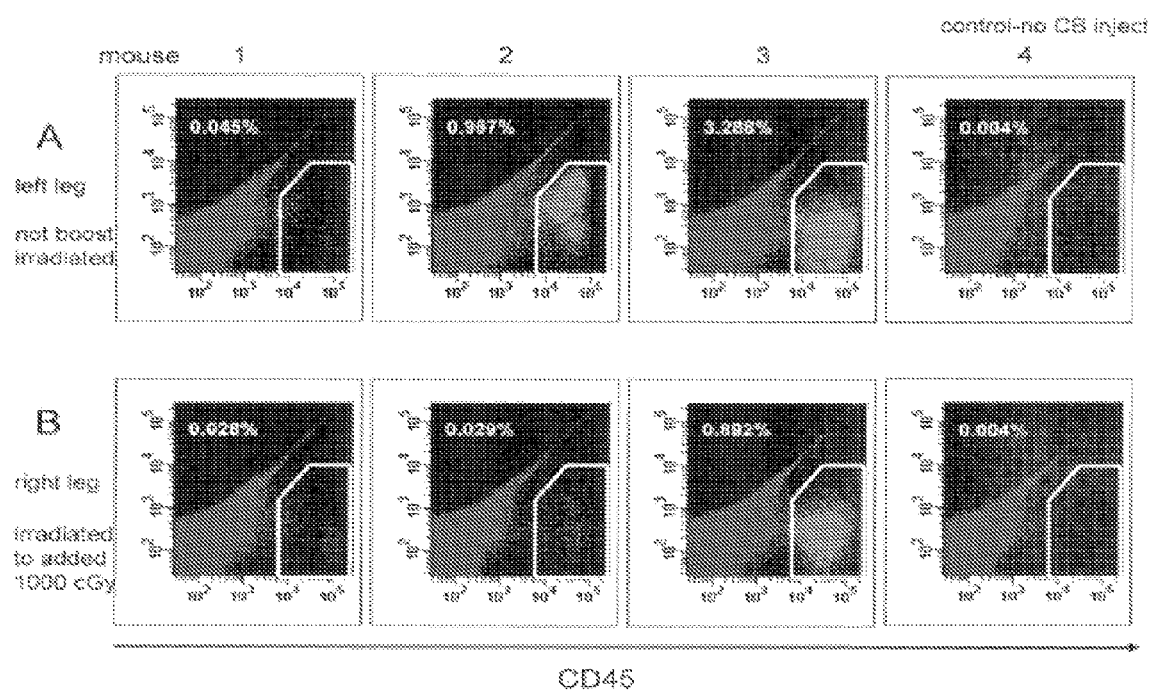
FIG. 21A shows results with detection of human cells in NOD/SCID mouse marrow harvested 27 days after cord blood transplanted I.V, showing flow cytometric analysis and identification of human CD45+ (light gray) hematopoietic cells in NOD/SCID mouse BM following irradiation, proximal tibia bone drilling (see below), and human cord blood injection.

We have significant preliminary data on use of NOD/SCID mice to test the effects of JP4-039 on human marrow stromal cell and hematopoietic stem cell recovery from total body irradiation to doses that cause the hematopoietic syndrome. FIG. 21A shows results with detection of human cells in NOD/SCID mouse marrow harvested 27 days after cord blood transplanted I.V, showing flow cytometric analysis and identification of human CD45+ (light gray) hematopoietic cells in NOD/SCID mouse BM following irradiation, proximal tibia bone drilling (see below), and human cord blood injection.

Six NOD/SCID mice were irradiated to 350 cGy and injected with $1 \times 10^7$ human cord blood (CB) mononuclear cells (MNC). Five months after the CB MNC cells were initially injected, the right leg of 6 mice was irradiated to 10 Gy. 24 hours post-irradiation holes were drilled in the tibiae. (See FIG. 21B) Drill bit size 1 mm diameter (Dremel Corp.). 24 hours post-bone drilling $1 \times 10^7$ CB MNC was injected into 3 of the 6 mice. Control mice (3) received no CB. 27 days after the CB was injected, the bones were harvested for histochemical analysis and flow cytometric analysis for human CD45+ cells (light grey) in the BM using a PE-conjugated anti-CD45 antibody (BD Biosciences). Analysis was performed on a BD LSR II flow cytometer (BD Biosciences). Human CD45+ cells were detectable in all of the mice (numbers 1-3) that received human CB MNC when compared to control mice (mouse 4). The percent of CD45+ cells ranged from 0.045-3.288 percent in the non boosted leg and from 0.028-0.892 percent in the high dose irradiated leg. There was no difference between the boost-irradiated and non boosted leg in these mice. Although the data suggest that there is a trend (the percent of human CD45+ cells was lower in the high dose irradiated leg), there was no statistically significant difference the total body irradiated non boosted compared to 1000 cGy boosted leg (p=0.25). Day 7 bone photo shown in FIG. 21B.

Figure 21B:
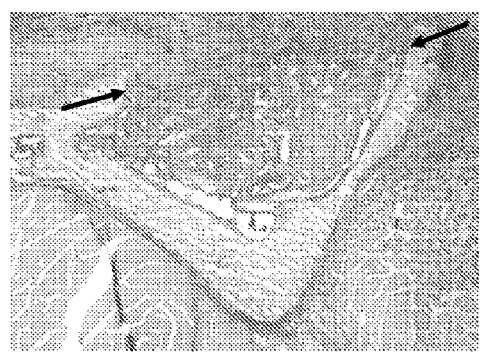
FIG. 21B is a photomicrograph of cross-section through a tibial wound 7-days after surgical construction with a drill bit of a unicortical 2-mm diameter wound in the lateral aspect of the tibia 2-mm below the proximal epiphyseal plate.

FIG. 21B is a photomicrograph of cross-section through a tibial wound 7-days after surgical construction with a drill bit of a unicortical 2-mm diameter wound in the lateral aspect of the tibia 2-mm below the proximal epiphyseal plate. Robust trabecular bone fills the intramedullary canal as well as the cortical window in this intermediate phase of spontaneous wound repair. This time point is optimal for assessing inhibition of marrow stromal cell mediated osteogenesis by irradiation and restoration by JP4-039, as proposed in this application. Arrows indicate margins of the wound. (Toluidine blue stain, x 35)(58)

EZAMPLE 12

Topical and Transdermal Absorption of GS-nitroxide

A practical skin patch is planned for delivery of JP4-039 or other compounds delivered herein. The patch can be administered to a subject before, during or after exposure to radiation, including 24 hr or later after irradiation exposure of the subject. In preliminary studies, we sought to characterize the absorption/penetration of a topically applied representative GS-Nitroxide XJB-5-125 in mouse skin. XJB-5-125 was selected as a potential topical agent based on its ability to inhibit ROS generation, inhibit apoptosis and suppress oxidative damage to mitochondrial lipids. XJB-5-125 comprises the (Leu-D-Phe-Pro-Val-Orn) segment of XJB-5-125 and has been shown to attenuate ActD-induced PS externalization in a dose-dependent manner of 2.5-20 µM. It can also inhibit the release of cytochrome c from mitochondria and suppress CL peroxidation. The physical properties of a chemical are critical to its ability to penetrate into and through the skin. Two important factors are the log octanal/water (Ko/w) partition coefficient and the molecular weight. For XJB-5-125, the log Ko/w=4.5 and molecular weight is 956. The lipophilicity "rule" is based on the need for a compound to partition out of the lipophilic stratum corneum and into the more hydrophilic epidermis and dermis. The log Ko/w and MW of XJB-5-125 are similar to ketaconazole (log Ko/w=4.34, MW=532), clotrimazole (log k/ow=6.27, $MW=_{902}$), and Indomethecin (log Ko/w=4.23, MW=358) suggesting feasibility of delivery using formulations similar to those used to effectively deliver these agents. Like JP4-039, XJB-5-125 is a radiation mitigator as well as a protector (see FIG. 15).

Figure 22:
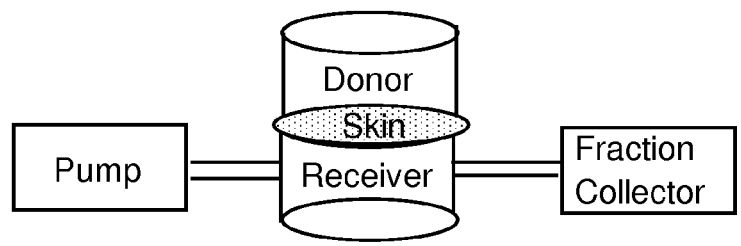
FIG. 22 is a schematic diagram of a Bronaugh diffusion system for studying in vitro transdermal flux.
Figure 23:
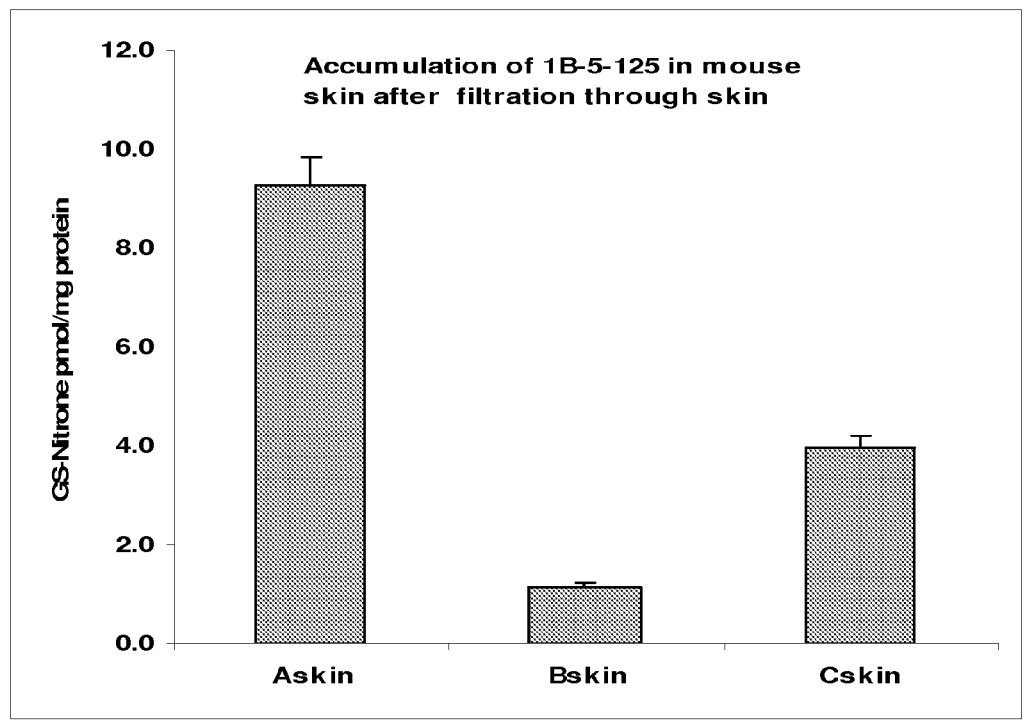
FIG. 23 is a graph showing delivery of XJB-5-125 into mouse skin after 24 hours.
Figure 24:
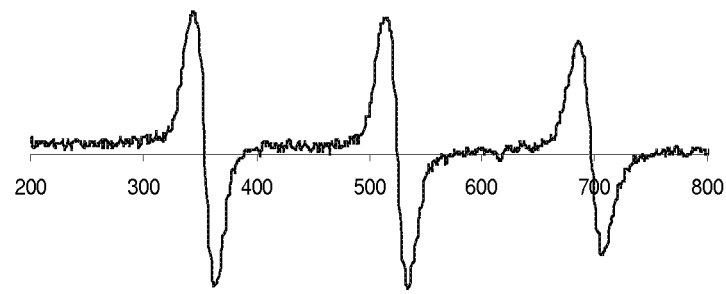
FIG. 24 shows typical EPR spectra of GS-nitroxides recorded from different fractions obtained after the filtration through the mouse skin. 1—donor fluid, 2—receiver fluid after 6 h of solution A filtration, 3—receiver fluid after 6 h of solution B filtration, 4—skin after 24 h exposure to solution A. The EPR spectra of GS-nitroxide radicals in medium, or skin homogenates were recorded in 28.5% of acetonitrile with addition of 2 mM $K_3Fe(CN)_6$
Figure 24:
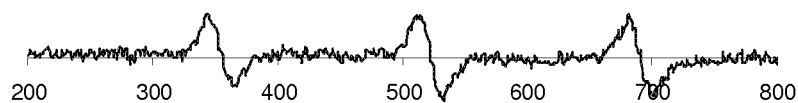
Figure 24:
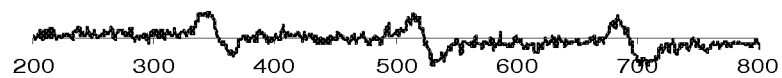
Figure 24:
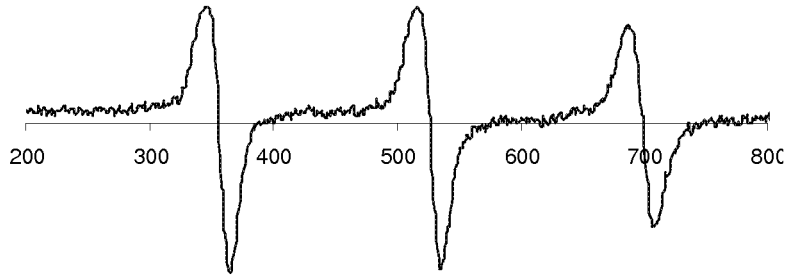
Figure 25:
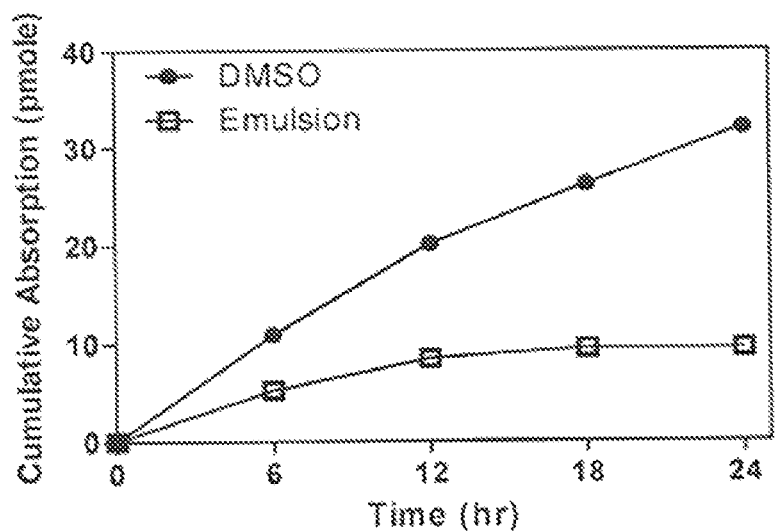
FIG. 25 is a graph showing cumulative transdermal absorption of XJB-5-125 through mouse skin over 24 hours

A small piece of skin (2 cm$^2$) was placed in a Bronaugh style flow-through diffusion cell system (PermeGear, Riegelsville, Pa.) (FIG. 22). It was then sandwiched between two pieces of the inert polymer Kel-F and clamped shut to prevent leakage. The epidermal side faces upward and is exposed to the donor solution (test solution), and the dermal side is in contact with the receptor fluid. The exposed surface area is 0.79 cm$^2$ (circular chamber with 1 cm diameter). The skin forms a water-tight seal in the flow through chamber so the receiving fluid (PBS+25% ethanol) on the dermal side will contain the XJB-5-125 only if it has penetrated through the skin. The receiver chamber was perfused with this buffer that then passes to a fraction collector via Teflon tubing. The PBS+25% ethanol was used because it is an effective sink for hydrophobic compounds and produces better in vitro/in vivo correlations than other receiver solutions. The skin was maintained at 32° C. by placing the chamber in a metal block heated via a recirculating water bath. The skin was equilibrated for 60 minutes prior to introduction of the test compound. Seventy five µL of XJB-5-125 was placed on the skin and was allowed to remain for the course of the experiment. The efflux was collected for 24 hours. (FIGS. 23-25).

To evaluate XJB-5-125 penetration in mouse skin, C57/BL6 mice were shaved using animal clippers (#40 blade), followed by a brief treatment with Nair (depilatory) to remove remaining hair. The skin was washed immediately after hair removal to prevent further irritation. The skin was allowed to recover for 24 hours prior to study. This reduces interference by hair and allows time for small abrasions to heal prior to dermal penetration studies.

Upon completion of the study, the skin was removed from the diffusion chamber. The stratum corneum, which will contain the majority of the topically applied compound, but is not relevant from a therapeutic standpoint, was removed by sequential tape-stripping (15 times) using Brookman Tape (3M, Minneapolis, Minn.). The remaining skin (viable epidermis and dermis) and transdermal effluent were assayed for XJB-5-125 via ESR.

Mouse skin was homogenized in 400 µL 50 mM PBS pH 7.4. EPR measurements were performed in gas-permeable Teflon tubing (0.8 mm internal diameter, 0.013 mm thickness) obtained from Alpha Wire Corp. (Elizabeth, N.J., USA) on a JEOL JES-RE1X spectrometer at 25° C. The Teflon tube (approximately 8 cm in length) was filled with 70 µL of sample containing 28.5% of acetonitrile and 2 mM K$_3$Fe(CN)$_6$, folded in half, and placed into an open EPR quartz tube (inner diameter of 3.0 mm) (FIG. 24)

EPR spectra were recorded at 334.7 mT, center field; 20 mW, power; 0.079 mT, field modulation; 5 mT, sweep width; 400 and 4000, receiver gain; 0.1 s, time constraint. Spectra were collected using EPRware software (Scientific Software Services, Bloomington, Ill., USA).

This preliminary experiment demonstrates that XJB-5-125 can sufficiently penetrate intact skin. Further, the total transdermal absorption after 24 hours and the level of XJB-5-125 present in the viable skin can be successfully measured using the techniques described herein. The effect of formulation on topical delivery was examined by using three different donor solutions (FIG. 25). Donor A=1 mM XJB-5-125 in DMSO, donor B=1 mM XJB-5-125 in 95% Propylene Glycol+5% Linoleic Acid, and Donor C=1 mM XJB-5-125 in 50% ETOH+40% HSO+5% Propylene Glycol+5% Brij30. A total of 75 nmole was placed on top of each piece of skin to begin these experiments (75 ul of 100 mM). The delivery of XJB-5-125 into the skin resulted in between 0.07% and 0.46% remaining within the skin after 24 hours. The higher delivery rate is in the range of other topical products.

Given the observation that XJB-5-125 is active in cells in the concentration range from 2.5-20 µM and assuming a tissue density of 1 g/cm$^3$, an order of magnitude analysis based on these data indicates that the topical delivery of XJB-5-125 method to enhance systemic blood levels to protect bone marrow is feasible.

Additionally, the fact that the total skin absorption is generally regarded as linearly related to the donor concentration implies that topical delivery will be greatly enhanced by increasing the donor concentration. These preliminary studies demonstrate feasibility of XJB-5-125 delivery to therapeutic levels and indicates that the smaller JP4-039 molecule, as well as other compounds described herein, may be useful as a skin patch-deliverable radiation mitigator of the hematopoietic syndrome.

EXAMPLE 13

Proposed

The following can be used to select and optimize the best GS-nitroxide JP4-039 (radiation damage mitigator drug) that can enhance human bone marrow stromal cell and fresh human stromal cell line seeding efficiency into irradiated limbs of NOD/SCID mice. MnSOD-overexpressing cells are a positive control.

A. Experiments with KM101-MnSOD/ds-red (control KM101-ds-red) clonal cell lines. Groups of 12 NOD/SCID mice receive 300 cGy total body irradiation (low dose leg) and a 1000 cGy boost to the left hind leg (high dose leg), then 24 hours later intravenous injection of 1×10$^5$ or 1×10$^6$ cells of each cell line (groups 1 and 2). Group 3 is mice that receive MnSOD-PL intravenously 24 hours prior to irradiation and then injection of KM101-MnSOD/ds-red. Group 4 is MnSOD-PL intravenously 24 hours prior to irradiation, then control KM101/ds-red cells. This experiment may be repeated twice. Mice will have bone marrow flushed from the hind limbs at days 1, 3, 7, 14 after cell transplantation, and scoring of the percent of total cells and number of colony forming cells recoverable which are ds-red positive thus of human origin. The scoring may be by ds-red positivity, and then by colony formation in vitro by stromal cells. We may score the total, then the percent of stromal cells of human origin.

B. Experiments demonstrating improvement in human bone marrow stromal cell line KM101 seeding by mitochondrial targeted radiation protection/mitigation JP4-039 (GS-nitroxide) administration. This experiment may be conducted essentially as described above (A), with all groups, but with a sub-group receiving JP4-039 (24 hours) after radiation (same day as cell lines are injected, or a sub-group receiving intraperitoneal JP4-039 (daily or weekly after cell line transplantation). Cells may be explanted from the high dose and low dose irradiated femurs at days 7, 14, 21, and cultured in vitro for human stromal colony forming progenitor cells (CFU-F). The percent and total number of human cells entering the high dose and low dose irradiated limbs can be quantitated by cell sorting for ds-red. Each experiment can be completed twice.

C. Experiments as in (A) above, but substituting fresh human marrow Stro1+ stromal cells from a 45 y.o. donor.

D. Experiments as in (B) above substituting Stro1+ human marrow stromal cells.

Statistical Considerations

In (A), we propose comparing at 4 different time points between 4 groups where either MnSOD or no MnSOD, and either $10^5$ or $10^6$ KM101 cells are injected, in terms of the number of DsRed-KM101 cells. In (B), we propose comparing at 3 different time points between 10 groups where different doses and schedules of the experimental compound will be used, in terms of the same endpoint as in (A). (C) and (D) are the same as (A) and (B) respectively, except that human stromal cells are used in place of KM101 cells. All the comparisons in this task are performed separately for high and low dose radiated legs. ANOVA followed by Tukey's test can be used for these analyses. Sample size can be estimated by the two sample t-test for pairwise comparisons. Due to the lack of preliminary data, sample size estimation is based on the expected difference to detect between groups in terms of the common standard deviation G. Six mice per group can be sacrificed per time point. With this sample size, there will be 82% power to detect a difference of 1.86 between groups using the two sided two sample t test with significance level 0.05.

As the secondary endpoint, the number of colony forming unit fibroblast (human) CFU-F can also be compared between groups with the same method as the primary endpoint.

It is expected that MnSOD Overexpression in KM101-MnSOD/ds-red cells will lead to a higher seeding efficiency into both the high and low dose irradiated limbs of NOD/SCID mice. We expect that MnSOD-PL treatment of the hematopoietic microenvironment prior to KM101 clonal line cell line infusion will further enhance engraftment of both KM101-MnSOD/ds-red and KM101-ds-red cell lines. We expect the highest percent of seeding efficiency will be detected in the mice receiving MnSOD-PL prior to irradiation and injection of KM101-MnSOD/ds-red cells.

We expect that JP4-039 administration daily after cell transplantation will facilitate improved stability of engraftment of all stromal cell lines by decreasing free radical production by the irradiated marrow microenvironment.

An inactive control compound for JP4-039 may be used, (JP4-039 absent the nitroxide active moiety). Based upon the results of these experiments, the optimal condition for bone marrow stromal cell seeding can be derived, and these conditions may be used in experiments described below.

EXAMPLE 14

Proposed

Selection and optimization of a GS-nitroxide JP4-039 therapy to enhance human CD34+ cord blood multilineage hematopoietic stem cell progenitor cell seeding into irradiated limbs of NOD/SCID mice that have been prepared by engraftment of human marrow stromal cells.

1. Experiments with TBI treated C57BL/6J mice and mouse marrow screening. (preliminary system test)
2. Experiments using the optimal seeding protocol for human KM101 cells into irradiated NOD/SCID mice (anticipated to be those mice receiving MnSOD-PL prior to irradiation, and then injection with KM101-MnSOD/ds-red, supplemented with JP4-039 daily). Mice can then receive intravenous injection of $1 \times 10^5$ or $1 \times 10^6$ CD34+ LIN− cells from human umbilical cord blood origin. Control cells may be CD34+ LIN+ (differentiated progenitor) cells $10^5$ or $10^6$ per injection. Groups of 12 mice.

These experiments may be carried out in two schedules.
   a. Injection of cord blood cells at the same time as KM101-MnSOD/ds-red cells.
   b. Injection of cord blood cells at time of optimal recovery of KM101-MnSOD/ds-red cells from the explant experiments of Example 13. This should be at day 7 or day 14 after stromal cell injection.

In these experiments, mice can be followed and tested at serial time points out to two months after cord blood stem cell transplantation. The percent of human peripheral blood hematopoietic cells can be scored in weekly peripheral blood samples and number of cells forming CFU-GEMM colonies can be tested in explanted bones from sacrificed mice.

At days 7, 14, 21, 28, or 60 after cord blood transplantation, mice in sub-groups may be sacrificed, and all cells flushed from the high dose and low dose irradiated femurs, and assays carried out for human multilineage hematopoietic progenitors-CFU-GEMM. Assays may be carried out by two methods:
   a. Sorting human CD34+ cells with monoclonal antibodies specific for human.
   b. Colony formation in human CFU-GEMM culture medium and then secondary scoring of human colonies as the subset of total mouse and human colony forming cells detected at days 7 and days 14 in vitro.

In vitro experiments may be carried out in parallel as follows:
KM101-MnSOD-PL plateau phase stromal cells may be irradiated in vitro to 100, 200, 500, 1000 cGy, and then CD34+ LIN− human cord blood cells co-cultivated with the stromal cells in vitro. Controls can include unirradiated KM101-MnSOD/ds-red, irradiated KM101-ds-red cells, unirradiated KM101-ds-red.

We can score human cobblestone islands (stem cell colonies) on these cultures weekly, plot cumulative cobblestone island formation, cumulative non-adherent cell production with weekly cell harvest, and assay of weekly cell harvest for CFU-GEMM formation. These studies may be carried out over two-three weeks. In vitro co-cultivation studies can only partially duplicate the in vivo hematopoietic microenvironment, and thus two weeks should be the maximum efficient time for detection of whether MnSOD-PL expression in the adherent KM101 layer will increase engraftment of cord blood stem cells.

3. Experiments with JP4-039 supplementation of the cord blood transplantation program as in (1) above to increase homing, stable quiescence, and repopulation capacity of human cord blood stem cells by removing ROS production in the irradiated marrow stromal cell environment.

Experiments in vitro supplementing in co-cultivation culture media the drug JP4-039 daily. The experiments with irradiated KM101 subclonal lines, co-cultivated with cord blood stem cells may be carried out with the addition of JP4-039, or an active analog JP4-039 daily. Control experiments can include addition of CD34+ LIN+ differentiated cord blood cells that are expected to produce fewer CFU-GEMM over time. Stromal cell cultures may be irradiated, cord blood cells added, and cultures scored as above.

Groups of 12 mice can receive the optimal protocol for human CFU-GEMM cell engraftment from the experiment above, and then sub-groups can be treated as follows:
 a. JP4-039 twice weekly.
 b. JP4-039 daily.
 c. Inactive JP4-039 analog daily.

4. Experiments as in (1) above substituting fresh human Stro1+ marrow cells for KM101 subclonal lines.
5. Experiments as in (2) above substituting human Stro1+ marrow cells for KM101 subclonal lines.

Statistical Considerations

In (1), we can compare at 5 different time points between 7 groups where we use MnSOD-KM101 and/or $10^5/10^6$ CD34+ cells, in terms of the number of CD45+ cells. In (2), we can compare at 5 different time points between 7 groups that use KM101, CD34+ cells, KM101 plus CD34+ cells, the experimental compound single or double administrations, or inactive analog of the experimental compound single or double administrations, in terms of the same endpoint as in (1). Tasks (3) and (4) are the same as (A) and (B) of Example 13, respectively, except that we can use human Stro1+ marrow cells in place of KM101 cells. All the comparisons in this task can be performed separately for high and low dose radiated legs. ANOVA followed by Tukey's test can be used for these analyses. Similar to the sample size considerations in Example 13, we will use 6 mice per group at each time point. As the secondary endpoint, the number of CFU-GEMM can also be compared between groups with the same method as the primary endpoint.

Likely Outcomes

Based on the results of Example 13, we expect that cord blood stem cell and human bone marrow stromal cell homing in vitro will be optimized by MnSOD-PL treatment of the mouse microenvironment prior to stromal cell transplantation, and that MnSOD-PL overexpressing KM101 cells will show further stability in the irradiated microenvironment. We expect that JP4-039 treatment will further enhance hematopoietic cell survival and increase CFU-GEMM in numbers.

EXAMPLE 15

Proposed

These experiments utilize osteogenesis by human stromal cells as a measure of effective mitigation of marrow injury by JP4-039. JP4-039 can be tested for repair of artificial fracture of the proximal tibiae in NOD/SCID mice by human stromal cell derived osteoblasts producing human collagen and can show enhanced fracture healing by antioxidant JP4-039 treatment.

A. Experiments with mice engrafted with KM101-MnSOD/ds-red compared to KM101 cells. Mice may have holes drilled in both proximal tibias as described above, then irradiation 300 cGy total body dose, 1000 cGy to one hind limb, and then 24 hours later injection of $1 \times 10^5$ bone marrow stromal cells of each line. Mice can be followed for 21 days and at serial seven days time points tibias explanted and assayed for relative content of human collagen in the healed bones.

B. JP4-039 weekly or daily supplemented injections in a repeat experiment of experiment described in (A) (12 mice per group).

C. Mice receiving MnSOD-PL intravenously 24 hours prior to irradiation (on the day of bone drilling), and then injection of either KM101-MnSOD/ds-red or KM101-ds-red.

D. Mice receiving scrambled sequence MnSOD-PL injection prior to cell line injection as described in (C) above.

E. Experiments as in (A-D) substituting fresh Stro1+ stromal cells for KM101 subclones.

Statistical Considerations

In (A), we compare at 3 different time points 17 groups that use KM101 cells, MnSOD, the experimental compound single or double administrations, scrambled MnSOD, or a combination of some of these, in terms of the percent of human collagen. (B) is the same as (A) except that human Stro1+ marrow cells are used in place of KM101 cells. All the comparisons in this task can be performed separately for high and low dose radiated legs. ANOVA followed by Tukey's test can be used for these analyses. Similar to the sample size considerations in Example 13, we can use 6 mice per group at each time point.

Likely Outcomes

We expect that KM101-MnSOD/ds-red will demonstrate improved osteogenic capacity in vivo. We anticipate that MnSOD-PL administration to mice 24 hours prior to irradiation will further enhance homing and osteoblast differentiation of KM101-MnSOD/ds-red.

Preliminary data show radiation survival curves of bone marrow stromal cell lines and enhancement of survival by MnSOD overexpression. Other preliminary data are expected to show that each Stro1+ cell transfected with MnSOD-PL and KM101-MnSOD/ds-red as well as KM101-ds-red are capable to differentiation to osteoblasts in vitro (osteogenic media experiments in progress) and in vivo in hole drilled NOD/SCID mice. Radiation survival curves of KM101-MnSOD/ds-red and KM101-ds-red treated with JP4-039, but not the inactive analog of JP4-039 are shown above. We anticipate that three conditions: 1) MnSOD-PL administration to the microenvironment, 2) overexpression of MnSOD in bone marrow stromal cell lines of human origin, and 3) supplementation of JP4-039 antioxidant therapy will lead to maximum osteogenic differentiation by human origin collagen producing cells. As further controls for the experiments, we can determine whether hematopoietic cells of human origin are required for optimal functioning of bone marrow stromal cells. KM101-MnSOD/ds-red stromal cell seeded NOD/SCID mice can be supplemented with injection of human cord blood CD34+ LIN−, or CD34+ LIN+ cells administered either with the stromal cells, or 24 hours later, to see if these cells produce optimal colony formation. Other controls can be CD34+ LIN−, CD34+ LIN+ hematopoietic cells only. Other controls may include STRO1+ stromal cells progenitors from cord blood alone or whole cord blood controls.

EXAMPLE 16

Bone Healing Acceleration in Mouse Model

To determine the effectiveness of novel mitochondrial targeted Tempo (GS-nitroxide, JP4-039) as a radioprotector in a combined injury (fracture/irradiation) model, we designed an in vivo assay system for measurement of the kinetics of bone healing.

Materials/Methods

Six groups of C57BL/6NHsd mice were studied. Thirty-one mice were given JP4-039 (100 ul; mg/kg) via an IP injection 10 minutes prior to 20 Gy irradiation (RT) to the right (r) hind limb. Fifty-five mice were given 100 ul (100 ug plasmid DNA) of manganese superoxide dismutase plasmid liposomes (MnSOD-PL) via tail vein injection 24 hours prior to 20 Gy RT to the r hind limb. Thirty-eight RT-control mice received 20 Gy to the r hind limb. Sixty-six control mice received no RT; 25 receiving MnSOD-PL 17 receiving JP4-039, and 24 receiving no drug. Twenty-four hours after RT, a skin incision was placed lateral to the anterior tibial crest of both hind limbs; the tibia was exposed and a unicortical wound was drilled at 5 mm below the proximal epiphysis with a 1.6 mm drill bit (Dremel, Racine Wis.). At 7, 14, 21, 28, and 35 days following drilling, groups of mice were sacrificed and limbs radiographed. X-rays were digitized into Adobe Photoshop CS3 (Adobe Systems Inc., San Jose, Calif.) for measurement of drilled holes.

Results

A significant RT-induced delay in osseus wound healing was noted at days 21 and 28 post-drilling in the 20 Gy group (mean hole diameters±SEM of 1.0±0.10 mm and 0.8±0 13 mm respectively) compared to the 0 Gy group (0.6±0.05 mm and 0.3±0.07 mm respectively, $p<0.05$). The administration of JP4-039 or MnSOD-PL prior to 20 Gy RT significantly ($p<0.05$) ameliorated this RT-induced delay. At 21 days post-drilling, the residual holes for the 20 Gy-JP4-039 and 20 Gy-MnSOD groups were 0.5±0.05 and 0.7±0.07 mm respectively, compared with 1.0±0.10 mm for the 20 Gy group ($p<0.05$). At 28 days post-drilling, significant differences in wound size persisted between the 20 Gy-JP4-039 group (0.4±0.04 mm, $p<0.05$) and the 20 Gy group (0.8±0.13 mm)

The addition of JP4-039 or MnSOD-PL conferred more rapid healing in the absence of RT. At 14 days post-drilling, the holes of the 0 Gy-JP4-039 (0.6±0.05 mm) and 0 Gy-MnSOD (0.5±0.05 mm) groups were significantly smaller ($p<0.05$) than the 0 Gy group (0.8±0.05 mm). At 21 days, a significant difference between the 0 Gy-MnSOD group (0.5±0.04 mm) and the 0 Gy group (0.6±0.04 mm) persisted ($p<0.05$).

CONCLUSION

GS-nitroxide JP4-039 is a potentially valuable radiation protector and damage mitigator in a novel murine model system for combined injury. The drug and the test system should be useful to guide the development of new small molecule radioprotectors of normal tissues.

Surprisingly it is noted that the compound is also seen to accelerate bone healing in both irradiated and non-irradiated mice, thus providing a further use for the antioxidant compounds described herein.

EZAMPLE 17

Small Molecule Gs-Nitroxide and Mnsod Gene Therapy Ameliorate Ionizing Irradiation-Induced Delay in Bone Wound Healing in a Novel Murine Model Purpose: An in vivo assay system for measurement of the kinetics of bone healing was developed and used to determine the effectiveness of novel mitochondrial targeted Tempo (GS-nitroxide, JP4-039) and Manganese Superoxide Dismutase Plasmid/Liposome (MnSOD-PL) as radioprotectors in a combined injury (fracture/irradiation) model.

Materials and Methods: Right hind legs of control C57BL/6NHsd female mice or mice pretreated with MnSOD-PL or JP4-039 were irradiated to doses of 0 to 30 Gy. Twenty-four hours later, unicortical holes were drilled into the tibiae of both hind legs. At intervals to 35 days, tibias were excised and radiographed to measure wound healing. The legs were then fixed for histological examination.

Results: Bone wounds in tibias irradiated to 20 or 30 Gy showed a significant delay in healing compared with nonirradiated tibias at 21 to 28 days. Pretreatment with MnSOD-PL or JP4-039 before 20 Gy followed by drilling of the tibias resulted in faster wound healing at days 14 and 21, compared with control 20 Gy irradiated tibias. In nonirradiated mice, pretreatment of MnSOD-PL or JP4-039 resulted in increased healing of the wounds.

The toxic effects of ionizing radiation on bone are of continued interest in radiation oncology. Whether in the treatment of primary bone tumors or in the management of tumors at other sites, including the pelvis or head and neck, significant volumes of bone can receive significant radiation dose. In pediatric patients, irradiation of bone can lead to vertebral body asymmetry, scoliosis, kyphosis, bone hypoplasia, and osteocartilaginous exostoses. The higher threshold dose for bone injury in adults is manifested primarily by osteoradionecrosis and fracture.

Irradiation of bone leads to depression of mineral metabolism, structural weakness, alteration of bone remodeling, and decreased vascularity. A number of studies in bone fracture models demonstrated that radiation significantly delays bone wound healing. It has been hypothesized that radiation impairs bone healing by damage to bone-regenerating osteoblast precursors in the bone marrow and periosteum.

Renewed interest in the effects of irradiation on bone concerns the risks of whole body/bone radiation in astronauts during long space missions and by increasing awareness of a combined injury effect of solar proton event (SPE) and galactic cosmic irradiation (GCI) with the osteoporosis of prolonged weightlessness. Some potential bone radioprotectors have been identified from studies of protection of other tissues. Amifostine is a free radical scavenger which prevents xerostomia in patients treated for head and neck cancers. Manganese superoxide dismutase plasmid liposomes (Mn-SOD-PL), which convert superoxide to hydrogen peroxide, is another antioxidant with proven in vivo and in vitro radioprotective properties.

Tempol (4-hydroxy-2,2,6,6-tetramethylpiperidine-N-oxyl) is a stable nitroxide that has been extensively studied and has demonstrated in vivo radioprotective properties against xerostomia in mice irradiated to the head and neck. By accepting one electron, nitroxide radicals are converted to hydroxylamines. Hydroxylamines act as free radical scavengers and are recycled back into nitroxides. In addition, nitroxides have superoxide dismutase mimetic activity, inhibit lipid peroxidation, and prevent the reaction of 02—with nitric oxide from forming toxic peroxynitrate (45-47).

A major mechanism of radiation-induced cell death is via mitochondrial-dependent apoptosis. The mitochondria are major sites of reactive oxygen species (ROS) production. Once production of ROS is initiated in the mitochondria by radiation, the ROS induce mitochondrial membrane permeabilization, allowing for the release of cytochrome c into the cytoplasm. Release of cytochrome c into the cytoplasm leads to apoptosis. A novel class of nitroxides have been created by coupling 4-amino TEMPO to gramicidin S (GS), thereby targeting the nitroxide to the mitochondria (Jiang J, et al. J Pharmacol Exp Ther 2007; 320: 1050-1060). By targeting the nitroxide to the mitochondria, scavenging of the ROS is increased and further prevents cell death. Hemi-GS-nitroxide JP4-039 (hemigramicidin S-conjugated 4-amino-2,2,6,6-tetramethyl-piperindine-N-oxyl) represents a unique small molecule GS-nitroxide with mitochondrial targeting.

We developed a murine combined fracture/bone wound-irradiation injury model to assess irradiation-induced delay in bone wound healing. We present evidence that antioxidant therapeutics MnSOD-PL and a novel GS-nitroxide (JP4-039) ameliorate the irradiation-induced delay in bone wound healing.

Methods and Materials

Mice: Adult female C57BL/6NHsd mice (20 to 22 g, Harlan Sprague Dawley, Chicago, Ill.) were housed according to IACUC protocols.

Experimental Design: The first phase of the study was to determine whether irradiation slowed the progression of bone wound healing and whether bone wound delay was dose-dependent. Four groups of C57BL/6NHsd mice were studied. Seventeen mice received 10 Gy to the right hind limb, 20 mice received 20 Gy, 20 mice received 30 Gy, and 13 mice received no irradiation (0 Gy). The left hind limbs of all mice were non-irradiated. Twenty-four hours after irradiation, unicortical wounds were created in the proximal tibiae of both hind limbs as described below.

The second phase of the experiments determined the effect of the antioxidant therapeutics MnSOD-PL or JP4-039 on bone wound healing. Six groups of C57BL/6NHsd mice were studied. Group 1 consisted of 24 non-irradiated control mice. Thirty-eight mice (Group 2) were given 20 Gy to the right hind limb. Groups 3 and 4 consisted of mice injected intravenously with 100 µl MnSOD-PL (100 µg of plasmid DNA in 100 µl water) 24 hr before irradiation or injected intraperitoneally with 100 µl JP4-039 (10 mg/kg as described below) 10 min prior to 20 Gy irradiation of the right hind limb. Groups 4 and 5 consisted of non-irradiated mice injected with the same above doses of MnSOD-PL or JP4-039, respectively. As another control, some mice were injected with 100 ul of a plasmid/liposome complex consisting of a plasmid missing the MnSOD transgene. Twenty-four hours after irradiation, holes were drilled in the proximal tibiae of both hind limbs.

Drug Delivery MnSOD-PL administered before irradiation is known to protect against irradiation induced damage. In these studies, MnSOD-PL and JP4-039 were administered before both irradiation and bone drilling. MnSOD-PL was injected intravenously with 100 µl of a MnSOD plasmid/liposome complex or a control blank plasmid/liposme complex containing 100 µg of plasmid DNA 24 hours prior to 20 Gy irradiation to the right hind limb (Epperly M W, et al. Radiat Res 2008; 170:437-43). JP4-039 was dissolved at a concentration of 2 mg/50 µl crempor el and 50 ul of ethanol. A volume of 100 µl of the JP4-039 stock solution was diluted 1:9 with water (900 µM. Mice were given 100 µl of JP4-039 at a dose of 10 mg/kg via intraperitoneal injection 10 minutes prior to 20 Gy irradiation to the right hind limb. After irradiation, 24 hours elapsed before tibial wounding, according to IACUC protocols to minimize stress on the animals. The 0 Gy group received MnSOD-PL 24 hours before osseous wounding or JP4-039 10 minutes before wounding.

Radiation Therapy: Radiation was delivered with a 6-MV linear accelerator (Varian Corporation, Palo Alto, Calif.) at 300 monitor units (2 Gy) per minute. Mice were anesthetized with nembutal and their right hind limbs were immobilized with paper tape within the confines of a 38×2 cm irradiation field. One centimeter of tissue-equivalent bolus was added to ensure full dose to the limbs. Doses of 10 Gy, 20 Gy, 30 Gy, 40 Gy, or 50 Gy were prescribed to 100 cm SBD (source to bolus distance) in the study to measure the effect of radiation dose on bone healing. Subsequent phases of this study exclusively used 20 Gy to the right limb.

Tibial Bone Wounds: The mouse model is based upon a model of tibial wound repair in rats (56). Mice were anesthetized by intraperitoneal injection of sodium phenobarbital (220-250 ul, 1:10 dilution in water, 70 mg/kg). Anesthetized mice were placed supine on a flat 10×5-cm Styrofoam board. Each hind limb was cleaned with alcohol (Kendall, Mansfield, Mass.), and a 15 mm incision of the skin lateral to the anterior tibial crest was created with surgical scissors. The lateral aspect of each tibia was exposed and carefully cleared of overlying soft tissue. A unicortical osseous wound was created 5 mm below the proximal epiphyseal cartilage plate with a handheld engraving drill (Dremel, Racine, Wis.) and a sharp 1.6 mm engraving cutter drill bit (Dremel, #113, Racine, Wis.). Evidence of unicortical osseous wounding was indicated by exposure of the marrow cavity. Irrigation with cold phosphate-buffered saline (PBS, 1×, Mediatech, Herndon, Va.) was used to remove bone dust and fragments. The soft tissue envelope was reapproximated and the skin was closed with two 9 mm stainless steel wound clips (Becton Dickinson, Sparks, Md.).

Radiographs and Measurements: Mice were sacrificed in groups of 5-10 at serial 7-day timepoints following drilling (days 7, 14, 21, 28, and 35 post-drilling). Radiographs of mice limbs were taken with a 35 kV x-ray machine (MX-20, Faxitron X-ray LLC., Lincolnshire, Ill.) and 1.5× magnification. Limbs were positioned with the lateral surface facing the beam. Radiographs (Kodak BioMax XAR, Rochester, N.Y.) were scanned, digitized, and imported into Adobe Photoshop CS3 (Adobe Systems Inc., San Jose, Calif.). The diameter of each hole was measured in triplicate in units of pixels with a ruler tool provided in the software package. Pixels were converted to millimeters (one pixel having been determined to be 1/100 of a millimeter). The triplicate values were averaged for statistical analysis. Measurement data for the non-irradiated left limbs of mice with irradiated right limbs were included in the non-irradiated groups for analysis.

Histological Examination: Excised tibiae were trimmed, fixed with 2% paraformaldehyde in 0.1 M cacodylate buffer (pH 7.4) for approximately one week at 4° C., rinsed in 0.1 M cacodylate buffer, and decalcified in ethylenediamine tetraacetate (EDTA 7.5% 0.1 M cacodylate buffer) for at least 5 weeks with solutions changed every two days the first week, and twice per week thereafter. The bones were embedded in glycol-methacrylate (JB-4, Polysciences, Warrington, Pa.). Five-µm cross-sections were mounted on Super-Frost slides (Fisher Scientific, Pittsburgh, Pa.) and were stained with toluidine blue (TB) and for tartrate-resistant acid phosphatase enzyme activity (TRAP) in osteoclasts (Schulten AJM, et al. Microsc Res Tech 2003; 61: 533-539).

Statistical Analysis: For the first phase of the study, two-sided two sample t-tests were used to compare drilled hole size for mice in each radiation dose group (10 Gy, 20 Gy, and 30 Gy) with that of the size of the drilled holes in mice in the 0 Gy group at each time point. For the second phase of the study, one-way ANOVA was performed to test whether the size of drilled holes in each of the six treatment groups (0 Gy, 0 Gy-MnSOD-PL, 0 Gy-JP4-039, 20 Gy, 20 Gy-MnSOD-PL, 20 Gy-JP4-039) was statistically the same at each time point. Tukey's test was used to determine the significant differences between treatment groups after the ANOVA. Tukey's test reveals significant differences between groups ($p<0.05$), but not specific p values.

Results

Ionizing irradiation delays tibial bone wound healing: There was a dose-dependent effect of irradiation in the range of 10 to 50 Gy on a delay in unicortical tibial bone wound healing. Groups of mice receiving doses of 40 Gy, or 50 Gy had significant soft tissue damage by day 28 such that bone wound healing could not be further studied and animals were euthanized according to IACUC regulations. Therefore, 10 Gy, 20 Gy, and 30 Gy groups were evaluated and compared with non-irradiated controls (Table 4). Spontaneous wound healing was detected as a time-dependent reduction in diameter in the 0 Gy group. At 7 and 14 days post drilling, no significant differences in sizes of the wounds were observed between the 0 Gy group and any of the irradiated groups. At 21 days post-drilling, significant differences were detected between the 20 Gy and 30 Gy groups (mean±SEM, 0.93±0.37 mm, p=0.008 and 1.07±0.19 mm, p=0.0002, respectively) compared with the 0 Gy group (0.68±0.27 mm) There were significant differences at 28 days post-drilling between the 10 Gy (0.76±0.15 mm, p=0.0003), 20 Gy (0.86±0.34 mm, p=0.04), and 30 Gy (0.76±0.15 mm, p=0.02) groups and the 0 Gy group (0.31±0.33 mm) By day 35, the size of drilled holes in all groups was below the sensitivity for measurement of hole size differences.

MnSOD-PL or JP4-039 ameliorate irradiation induced delay in bone wound healing: We evaluated the effects of antioxidants JP4-039 and MnSOD-PL on bone wound healing (Table 5). The set of samples not exposed to irradiation (0 Gy) showed gradual healing similar to the first control group. Comparison of the groups exposed to 20 Gy alone, 20 Gy-MnSOD, and 20 Gy-JP4-039 revealed no differences in hole size at days 7 or 14 post drilling Significant amelioration of the effects of irradiation on bone wound healing was observed at day 21 post drilling in both the 20 Gy-JP4-039 group (mean±SEM, 0.51±0.05 mm, p<0.05) and the 20 Gy-Mn-SOD-PL (0.68±0.07 mm, p<0.05) group, compared with the 20 Gy group (1.01±0.10 mm) At 28 days post-drilling, a significant difference in hole diameter was observed between the 20 Gy-JP4-039 group (0.37±0.04 mm, p<0.05) or 20 Gy-MnSOD-PL group (0.49+0.04 mm, p<0.05) and the 20 Gy group (0.76±0.13 mm)

TABLE 4

Irradiation induced delay in healing of unicortical osseous wounds in mouse tibiae.

| Day post-drilling | Treatment Group Hole Diameter presented as mean ± SEM in mm | | | |
|---|---|---|---|---|
| | 0 Gy | 10 Gy | 20 Gy | 30 Gy |
| Day 7 | 1.08 ± 0.25 | 1.13 ± 0.19 | 1.17 ± 0.04 | 1.25 ± 0.14 |
| Day 14 | 0.84 ± 0.24 | 1.27 ± 0.35 | 1.09 ± 0.37 | 1.13 ± 0.27 |
| Day 21 | 0.68 ± 0.27 | 0.76 ± 0.21 | 0.93 ± 0.20* (p = 0.008) | 1.07 ± 0.19* (p = 0.0002) |
| Day 28 | 0.31 ± 0.33 | 0.76 ± 0.08* (p = 0.0003) | 0.86 ± 0.34* (p = 0.04) | 0.76 ± 0.15* (p = 0.02) |

Unicortical osseous wounds were created by drilling of anesthetized mice and limbs were irradiated to each dose as described in the Methods (n=5 mice in each group). Hole size diameter was measured as described in the methods and is presented as mean±standard error of the mean in mm Two-sided two sample t-tests were used to compare drilled hole size in each irradiation dose group (10 Gy, 20 Gy, and 30 Gy) with that of the size of drilled holes in the control nonirradiated (0 Gy) group at each time point. Statistically significant differences in drilled hole size between the 0 Gy control group and each irradiated group are indicated by astericks. There was no significant difference in hole size by x-ray examination attributable to difficulty in measuring 0.05 mm between groups at 35 days differences below increments. Mice receiving doses higher than 30 Gy showed severe soft tissue damage and skin ulceration at day 28 preventing calculation of bone hole size diameter in these higher dose groups.

TABLE 5

Small molecule GS-nitroxide JP4-039 or MnSOD-PL ameliorate irradiation induced delay in unicortical osseous murine tibiae wound healing.

| Day post-drilling | Treatment Group (Hole Diameter presented as mean ± SEM in mm) | | | | | |
|---|---|---|---|---|---|---|
| | 0 Gy alone | 0 Gy-MnSOD-PL | 0 Gy-JP4-039 | 20 Gy alone | 20 Gy-MnSOD-PL | 20 Gy-JP4-039 |
| Day 7 | 1.10 ± 0.05 (21) | 1.12 ± 0.05 (13) | 1.02 ± 0.07 (9) | 1.20 ± 0.11 (7) | 1.23 ± 0.11 (5) | 1.14 ± 0.04 (5) |
| Day 14 | 0.84 ± 0.05 (21) | 0.49 ± 0.05* (31) | 0.55 ± 0.03* (11) | 1.01 ± 0.08 (8) | 0.87 ± 0.08 (13) | 0.92 ± 0.08 (5) |
| Day 21 | 0.64 ± 0.05 (22) | 0.41 ± 0.04* (29) | 0.47 ± 0.04* (16) | 1.01 ± 0.10 (8) | 0.68 ± 0.07** (16) | 0.51 ± 0.05** (8) |
| Day 28 | 0.30 ± 0.07 (20) | 0.38 ± 0.05 (16) | 0.23 ± 0.04 (16) | 0.76 ± 0.13 (8) | 0.49 ± 0.04** (16) | 0.37 ± 0.04** (8) |

Unicortical wounds were created as described in the Methods section and in the legend for Table 4. Number of mice in each group is shown in ( ). Hole diameter is presented as mean±standard error of the mean in mm A one-way ANOVA was performed to determine significant differences in the diameters of drilled holes in each of the six treatment groups at each time point. Tukey's test was then used to determine significant differences between treatment groups after ANOVA. Statistically significant differences (p<0.05) in hole diameters between nonirradiated control (0 Gy) and drug treated nonirradiated treatment groups are indicated by one asterisk. Statistically significant differences (p<0.05) in hole size between the 20 Gy irradiation control group and 20 Gy drug treatment groups are indicated by two asterisks.

Comparison of the non-irradiated groups (0 Gy alone, 0 Gy-MnSOD-PL, 0 Gy-JP4-039) revealed no significant differences in hole diameters at day 7 following drilling. At day 14, significant differences were observed in comparisons between either the 0 Gy-JP4-039 (0.55±0.03 mm, p<0.05) or 0 Gy-MnSOD-PL groups (0.49±0.05 mm, p<0.05), with the 0 Gy alone group (0.84±0.05 mm) At 21 days post-drilling, a therapeutic effect of MnSOD-PL and JP4-039 was observed (0 Gy-MnSOD-PL: 0.41±0.04 mm or JP4-039: 0.47+0.04 mm, versus 0 Gy alone: 0.64±0.05 mm, p<0.05). No significant differences were observed between MnSOD-PL or JP4-039 treatment compared with control irradiation groups at 28 days post drilling.

Figure 26:
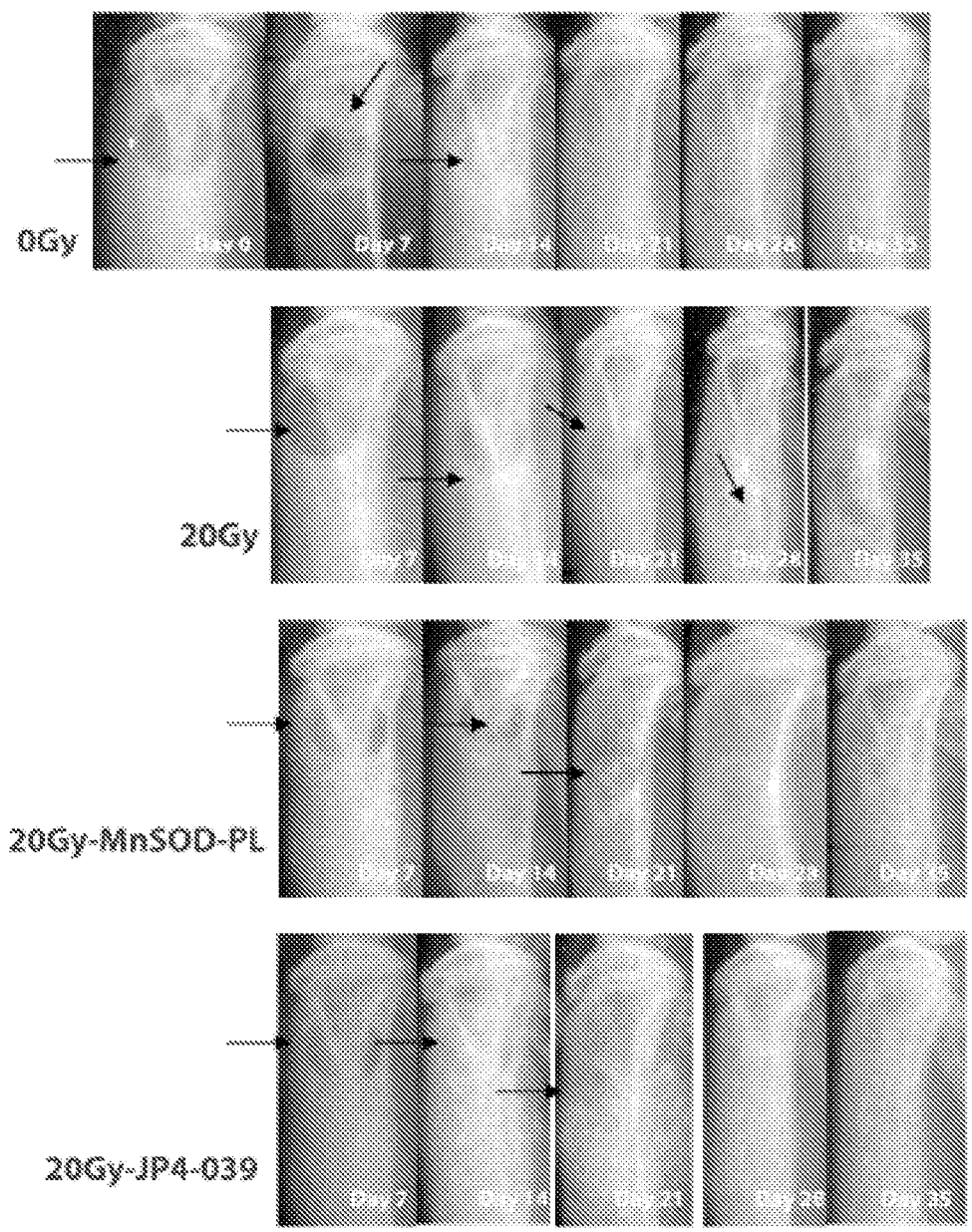
FIG. 26: Radiographs of representative unicortical bone wounds in the tibia of control mice and mice with irradiated legs without and with pretreatment with MnSOD-PL or JP4-039. Top two groups display mice irradiated to 0 or 20 Gy respectively to the right hind limb twenty-four hrs prior to creation of tibial wounds. The bottom two groups represent mice pretreated with MnSOD-PL or JP4-039 before 20 Gy irradiation and subsequent creation of tibial wounds. Subgroups of mice in each group were sacrificed on day 7, 14, 21, 28, or 35 days after drilling, and excised limbs were radiographed. Arrows indicate tibial wounds. Time-dependent reduction in wound diameter was prevented by 20 Gy irradiation and was restored in mice that were pretreated with either MnSOD-PL or JP4-039. (Magnification ×1.5).

Representative radiographs of proximal tibiae from the 0 Gy, 20 Gy, 20 Gy-MnSOD-PL, and 20 Gy-JP4-039 groups reveal the effects of time and treatment on bone wound healing (FIG. 26). Excised mouse tibiae were x-rayed using a 35 kV x-ray machine (MX-20, Faxitron X-ray LLC, Lincolnshire, Ill.). Photographs of representative tibiae at each time point are presented. Arrows show persistent visible holes at day 21 and day 28 in the 20 Gy irradiation compared to nonirradiated controls (0Gy) or irradiated MnSOD-PL or JP4-039 treated irradiated mice. Radiographs in the 0 Gy group demonstrated decrease in wound size. In contrast, holes in 20 Gy irradiated bones were persistent and visible through 28 days. Radiographs of bones from 20 Gy irradiated mice which had been pre-treated with MnSOD-PL or JP4-039 demonstrated persistence of holes though day 21, with healing by day 28.

Figure 27:
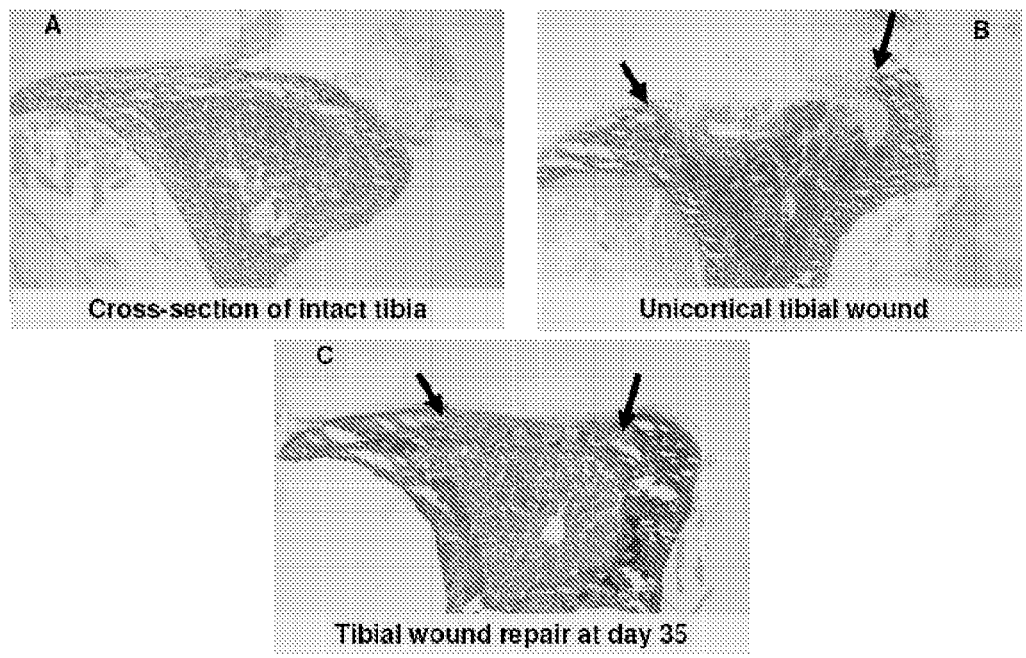
FIG. 27: Photomicrographs of A: intact tibia, B: tibia after creation of unicortical tibial wound, and C: tibia 35 days after creation of tibial wound. Decalcified bones were embedded in glycol-methacrylate, cross-sectioned at 10-1 μm, and stained with toluidine blue. Arrows indicate margins of the wound. Complete wound healing is evidenced by osseous bridging at day 35. (Magnification 28×).
Figure 28:
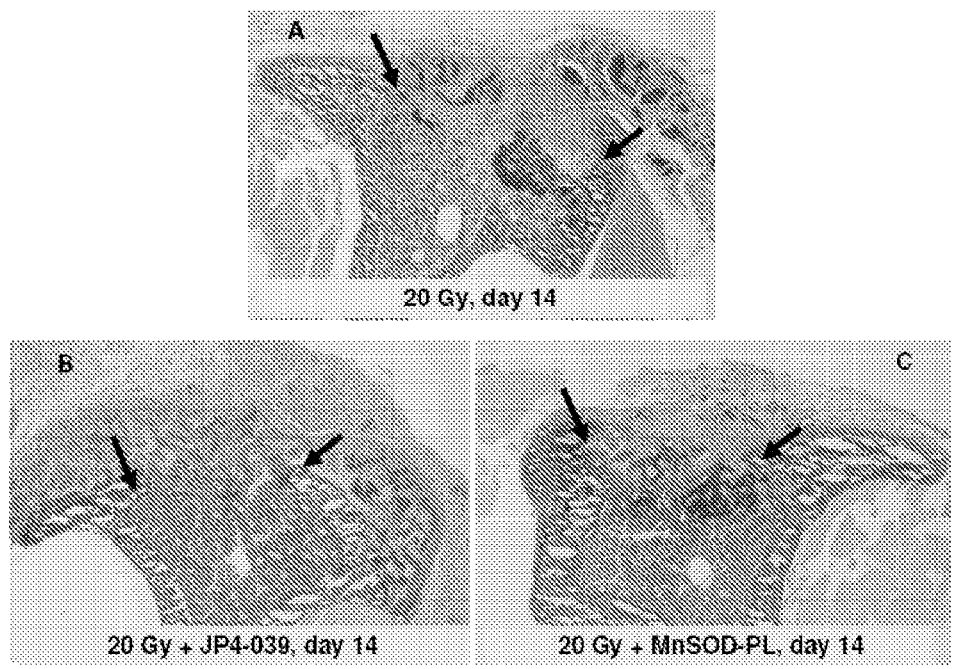
FIG. 28: Photomicrographs of tibia 14 days after creation of wounds in mice with A: 20 Gy irradiation; B: 20 Gy irradiation and pretreatment with JP4-039; and C: 20 Gy irradiation and pretreatment with MnSOD-PL. Decalcified bones were embedded in glycol-methacrylate, cross-sectioned at 10-μm, and stained with toluidine blue. Arrows indicate margins of the wound. The wound from a mouse with limb irradiated to 20 Gy was filled with fibrous connective tissue and robust neo-osteogenesis is visible in wounds from mice that were irradiated and pre-treated with either JP4-039 or MnSOD. (Magnification 28×).

Histopathological evaluation of controls indicated that tibial wounds spontaneously healed, with complete bridging with new bone by 35 days (FIG. 27). Specimens from mice with irradiation of limbs prior to wounding revealed more fibrous tissue than reactive bone in the wounds (FIG. 28). Specimens from animals that were pre-treated with JP4-039 or MnSOD-PL prior to irradiation revealed more bone fill than in specimens from irradiated mice (FIG. 29). These histological findings confirm the irradiation-induced delay in bone wound healing and the ameliorating effects of JP4-039 or MnSOD-PL.

The histopathology of fracture healing and the effects of ionizing irradiation on the process represent a potentially complex setting. Normally, upon a bone fracture, a hematoma/fibrinous clot is formed, followed by phases of inflammation and ischemia. Local growth factors recruit polymorphonuclear cells, macrophages, mast cells, and mesenchymal stem cells (MSCs) to the fracture site The MSCs differentiate into chondrocytes and osteoblasts. In addition, osteoblastic precursors are mobilized systemically from the peripheral circulation and home to the fracture site. The osteoblast precursors undergo migration, proliferation, and differentiation. The stages in fracture healing include cartilage formation, calcification, angiogenesis, cartilage removal, bone formation, and bone remodeling.

Histological evaluation of bone repair following irradiation demonstrated loss of osteocytes, absence of osteoblasts from the bone surface, hyaline necrosis of blood vessels, and replacement of bone marrow by fibrous connective tissue. It is thought that radiation impairs bone healing by impairing the proliferation of bone-regenerating precursor cells located in the bone marrow. The loss of precursor cells leads to a quantitative reduction of bone forming osteoblasts. In addition, vascular injury by radiation is thought to impair bone healing by reducing angiogenesis at sites of new bone formation. Endochondrial ossification has been demonstrated to be dependent on adequate vascularity (Chan CKF, et al. Nature 2009; 457: 490-495).

A number of studies have demonstrated a delay in bone fracture healing with irradiation (Datta R. Med Phys 1983; 10: 243-245; Hamilton S A, et al. J Appl Physiol 2006; 101: 789-793; Markbreiter L A, et al. J Ortho Res 1989; 7:178-183; Pelker R et al. Clin Orthop Relat Res 1997; 341:267-282; Pelker R, et al. J Ortho Res 1984; 2:90-96; Regen E M, et al. J Bone Joint Surg 1936; 18:69-79; Spittler A W, et al. Arch Surg 1954; 68:93-104; and Widmann R F, et al. J Orthop Res 1993; 11: 422-428). The present study confirms the observation of a irradiation-induced delay in bone wound healing. At 21 days post-drilling, the wounds in the 20 Gy and 30 Gy groups were significantly larger than in the 0 Gy group. By 28 days, all irradiated groups (10 Gy, 20 Gy, and 30 Gy) had persistent holes in size significantly greater than that of the 0 Gy control. At 35 days post-drilling, no significant differences were noted, but the sensitivity of measurements was not likely able to determine differences in residual small and irregular wounds. In addition, these studies do not rule out the possibility that there was significant recovery after these single doses of irradiation. Arnold et al. demonstrated a dose-dependent impairment of early bone wound repair in rats given 10-22 Gy 24 hours prior to injury of the femur (Arnold M, et al. Radiat Res 1995; 143: 77-84). There was severe impairment of bone wound healing at doses >19 Gy with reduced deposition of callus. Similarly, in our study, delay in bone wound healing appeared to be dose-dependent. Tibiae irradiated to >20 Gy showed a significant delay in bone wound healing compared with the 0 Gy group.

Few studies have provided methods of ameliorating combined fracture-irradiation injury. Wurzler et al. found that recombinant human bone morphogenic protein-2 led to more rapid healing of bone defects in the rat calvaria irradiated to 12 Gy prior to creation of the defect (Wurzler K, et al. J Craniofac Surg 1998; 9: 131-137). In the present study, we demonstrated that antioxidants JP4-039 and MnSOD-PL ameliorated the effects of irradiation on bone wound healing. Bone wound healing was restored in both the 20 Gy-JP4-039 and 20 Gy-MnSOD-PL groups compared with the 20 Gy alone group (day 21). At 28 days, there was more bone healing in the 20 Gy-JP4-039 group compared with the 20 Gy alone.

Another interesting finding in our study was the increased early bone wound healing with the addition of JP4-039 or MnSOD compared with controls in the absence of irradiation. At 14 days post-drilling, wounds in the 0 Gy-JP4-039 and 0 Gy-MnSOD-PL groups were significantly smaller than the 0 Gy group. At 21 days post-drilling, a significant benefit of MnSOD-PL persisted. Because of the generation of damaging free radicals produced by fracture, it is possible that the agents used in this study improved bone healing because of their antioxidant effects. Benefits of common antioxidants in fracture healing have been suggested in the literature. Dygulu et al. reported that daily injections of vitamin C mitigated the damaging effect of 5 days of intraperitoneal injections of zymosan on fracture healing, but they did not examine effects on fracture healing in rats not treated with zymosan (Duygulu F, et al. Arch Orthop Trauma Surg 2007; 127:493-501). Similarly, Durmus et al. found more rapid bone healing in dogs given vitamin E daily for one week following radial diaphysis fracture (Durmus A S, et al. Firat University Journal of Health Sciences 2008; 22:141-146).

Thus, using a unique murine model of combined bone wound/irradiation injury, we demonstrate ameliorating effects of GS-nitroxide JP4-039 and MnSOD in irradiation-induced delay of bone wound healing. Even in the absence of irradiation, these antioxidants may stimulate bone wound healing. These classes of antioxidant drugs and this test system will be of value in developing new small molecule radioprotectors and radiomitigators.

EXAMPLE 18

Exemplary JP4-039 Formulations

All compositions are sterile filtered (e.g.) using a 0.2 micron filter (non sterile).
A. 0.1% DMSO 99.9% and RMPI 1640. Comments: with the low water solubility of JP4-039, DMSO is used in vitro experiments since it is a universal solvent which has been used in radiation biology experiments without any toxic effects.
B. 10% CrEL(Cremophor EL), 10% ethanol and 80% DI water. Comments: JP4-039 has a low solubility in water. This formula dissolves the JP4-039.
C. Suspension of JP4-039 in F14 emulsion: Comments: F14 is a mixture of sesame oil, egg-phosphatidyl choline, Tween 80, and Span85 at ratios of 1:0.5:0.25:0.25 w/w, respectively. This formula has been administered to mice IV and has demonstrated irradiation protection equivalent to the JP4-039 Cr EL formulation and ethanol when given 10 minutes after irradiation exposure.
D. JP4-039 in F14-III—Formulation. Comments: Sesame Seed Oil (100 mg/ml), Soy Phosphatidyl Chlorine (50 mg/ml), JP4-039 (2 mg/ml), and Phosphate Buffered Saline.
Low dose (JP4-039): 5 mg/kg, 0.5 mg/ml.
Medium dose (JP4-039): 10 mg.kg, 1.0 mg/ml.
High dose (JP4-039): 20 mg/kg, 2.0 mg/ml.
Placebo/Vehicle (JP4-039): 0 mg/kg, 0 ing/ml
Exemplary dose (mouse): 200 µl of volume
E. JP4-039 dissolved in a solution of 45% 2-hydroxypropyl-β-cyclodextrin and 55% water. Comments: Cyclodextrins have a hydrophobic interior which compounds such as JP4-039 can complex in a rapid and reversible reaction. P-cyclodextrins have a cavity with an inner diameter of approximately 7.5 Å which is well suited for JP4-039. This cyclodextrin has been demonstrated to increase drug solubility.

EXAMPLE 19

Bone Healing Acceleration in SAMP6 Mouse Model

SAMP6 mice are used to test the expected delay in unicortical bone wound healing in these mice. Compared to SAMR1 (control littermates and C57BL/6 controls), SAMP6a mouse derived from bone marrow stromal cells show typical characteristics of premature cellular senescence (Lecka-Czernik, et al., Journal of Gerontology A Biology Science Medical Science, 52:B331-6, 1997). These mice also show low bone density and are an excellent model of human osteoporosis (Kasai, et al., JBMR, 42:207-214, 2004). The mice are an excellent example of the collagen deficits in human osteoporosis (Silva, et al., *JBMR,* 21:78-88, 2006). There are numerous other data indicating that SAMP6 mice are an excellent model for human osteoporosis.
The experiments in progress are of two categories
1. The effects of SAMP6 genotyping on expected delay in cortical bone healing using the unicortical wound modeling.
2. Effects of irradiation on bone wound healing delay in SAMP6 mice compared to controls.
3. The effect of JP4-039 administered in F14-III emulsion on accelerating bone wound healing in the absence of irradiation in SAMP6 mice.
4. Effects of JP4-039 in the F14 emulsion on decreasing irradiation-induced bone wound healing delay in SAMP6 mice compared to control mice.

To determine the effectiveness of novel mitochondrial targeted Tempo (GS-nitroxide, JP4-039) as a radioprotector in a combined injury (fracture/irradiation) model, we designed an in vivo assay system for measurement of the kinetics of bone healing. Experiments will be carried out essentially as described in Examples 16 and 17. SAMP1 and

EZAMPLE 20

Effects of JP4-039 on Accelerating Bone Wound Healing as Facilitated by Donor Bone Marrow Stromal Cells We have experiments in progress now with unicortical bone wound healing in NOD/SCID mice injected with human cord blood cells. The hypothesis is that human cord blood cells will facilitate wound healing, and that we will be able to document this by not only detection of human osteoblasts in the wound sites by histomorphometry, but also detection of human collagen in the bone wound sites. Bones from NOD/SCID mice receiving 20 Gy to the irradiated leg, and control leg with no irradiation (tibia wounds in both legs) were monitored for the 35 days of bone wound healing. A subgroup received human umbilical cord blood intravenously 24 hours after wounding. These mice are being evaluated for the effect of irradiation on decreasing the role of human cells in pushing healing of the drilled holes (1 mm, as above). The next set of experiments will involve JP4-039 administered in the F14 emulsion immediately after wound healing, after cord blood injection, or after irradiation. The protocol now is to drill the holes (1 mm, as above), then irradiate, and then deliver the human cord blood intravenously (e.g. $5 \times 10^6$ cells). The other combinations have experimental procedure will be included in which the JP4-039 is given after the bone drilling, but before irradiation, or the JP4-039 is given after drilling, after irradiation, but before the cord blood injection, and, of course, the other combinations of experiments in which JP4-039 F14 emulsion is given at all three times. In these experiments one tibia is irradiated, the other is unirradiated. There are unicortical tibia wounds in both sides. We expect these experiments will show two things relevant to JP4-039:
1. JP4-039 is expected to show increased homing and biological functioning of the human cord blood derived cells in the tibia wounds and an effect of irradiation on decreasing this therapeutic effect of the donor cells.
2. It is expected that JP4-039 alone will stimulate bone wound healing in the absence of cord blood injection and will further facilitate healing in those mice that receive both cord blood injection and JP4-039.

Whereas particular embodiments of this invention have been described above for purposes of illustration, it will be evident to those skilled in the art that numerous variations of the details of the present invention may be made without departing from the invention as defined in the appended claims.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

We claim:

1. A method of accelerating bone healing, growth or repair in a subject, comprising administering to the subject during or after bone injury, damage or deficiency in the subject, a composition comprising an amount of a targeted nitroxide compound effective to accelerate bone repair in the subject, wherein the targeted nitroxide compound comprises a mitochondria targeting group and a nitroxide-containing group, wherein the targeted nitroxide compound is chosen from one of:

a) a compound having the structure:

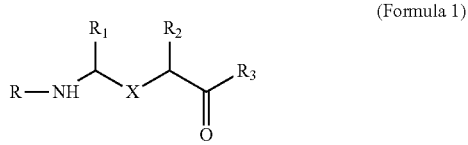

(Formula 1)

wherein X is

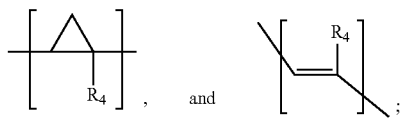

$R_1$ is $C_1$-$C_6$ straight or branched-chain alkyl, or a $C_1$-$C_6$ straight or branched-chain alkyl further comprising a phenyl ($C_6H_5$) group, that is unsubstituted or is methyl-, hydroxyl- or fluoro-substituted, $R_2$ and $R_4$ are independently selected from hydrogen, $C_1$-$C_6$ straight or branched-chain alkyl, or a $C_1$-$C_6$ straight or branched-chain alkyl further comprising a phenyl ($C_6H_5$) group, that is unsubstituted or is methyl-, hydroxyl- or fluoro-substituted; $R_3$ is —NH—$R_5$, —O—$R_5$ or —CH$_2$—$R_5$, and $R_5$ is an —N—O., —N—OH or N=O containing group; R is —C(O)—$R_6$, —C(O)O—$R_6$ or diphenylphosphate, and $R_6$ is $C_1$-$C_6$ straight or branched-chain alkyl or $C_1$-$C_6$ straight or branched-chain alkyl further comprising one or more phenyl (—$C_6H_5$) groups that are independently unsubstituted, or methyl-, ethyl-, hydroxyl- or fluoro-substituted, and wherein the compound is not XJB-5-208;

b) a compound having the structure R1—R2—R3 in which R1 and R3 are the same or different and have the structure —R4—R5, in which R4 is a mitochondria targeting group and R5 is —NH—R6, —O—R6 or —CH$_2$—R6, wherein R6 is an —N—O., —N—OH or N=O containing group and R4 and R5 for each of R1 and R3 may be the same or different; and R2 is a linker; or c) from 2-10 consecutive amino acids of a gramicidin S polypeptide attached to a nitroxide-containing group.

2. The method of claim 1, the compound having the structure:

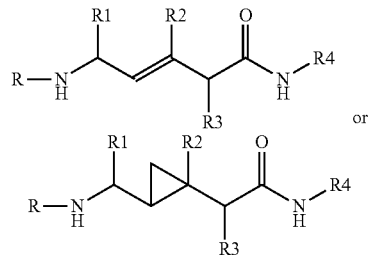

or in which R1 is $C_1$-$C_6$ straight or branched-chain alkyl, or $C_1$-$C_6$ straight or branched-chain alkyl including a phenyl ($C_6H_5$) group that is unsubstituted, methyl-, hydroxyl- or fluoro-substituted; R2 and R3 are, independently, H, $C_1$-$C_6$ straight or branched-chain alkyl, or $C_1$-$C_6$ straight or branched-chain alkyl including a phenyl ($C_6H_5$) group that is unsubstituted, methyl-, hydroxyl- or fluoro-substituted; R4 is an —N—O, —N—OH or N=O containing group; R is —C(O)—R5, —C(O)O—R5 or diphenylphosphate, and R5 is $C_1$-$C_6$ straight or branched-chain alkyl, or $C_1$-$C_6$ straight or branched-chain alkyl including a phenyl ($C_6H_5$) group that is unsubstituted, methyl-, hydroxyl- or fluoro-substituted.

3. The method of claim 2, in which R5 is Boc or Cbz.

4. The method of claim 2, in which R1, R2 and R3 independently are methyl, ethyl, propyl, 2-propyl, butyl, t-butyl, pentyl, hexyl, benzyl, hydroxybenzyl, phenyl and hydroxyphenyl.

5. The method of claim 2, in which R4 is 2,2,6,6-Tetramethyl-4-piperidine 1-oxyl.

6. The method of claim 2, having a structure chosen from:

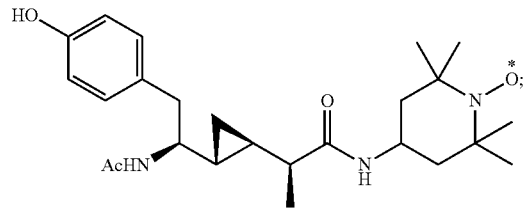

D1

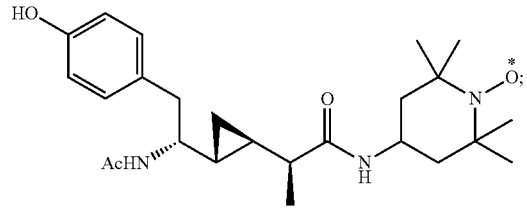

D2

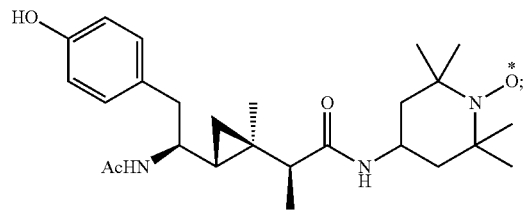

D3

A1

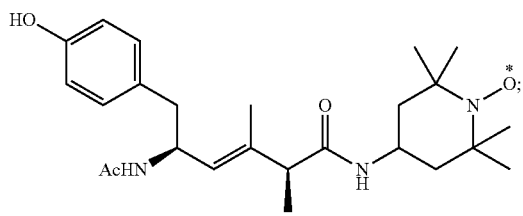

A2

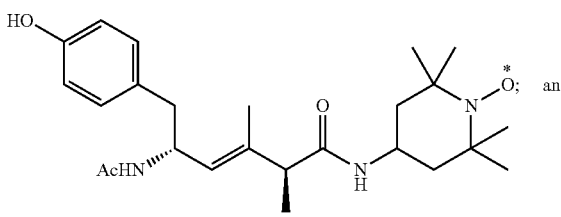 and

A3

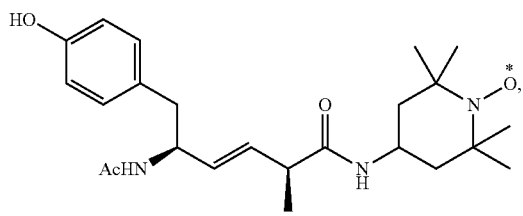

wherein Ac is acetyl.

7. The method of claim 2, wherein the compound is JP4-039 or JP4-049.

8. The method of claim 1, in which the targeted nitroxide compound is a compound having the structure R1—R2—R3 in which R1 and R3 are the same or different and have the structure —R4—R5, in which R4 is a mitochondria targeting group and R5 is —NH—R6, —O—R6 or —CH₂—R6, wherein R6 is an —N—O., —N—OH or N=O containing group and R4 and R5 for each of R1 and R3 may be the same or different; and R2 is a linker.

9. The method of claim 8, wherein R1 and R2 are the same.

10. The compound of claim 8, wherein R6 for one or both of R1 and R2 is 2,2,6,6-Tetramethyl-4-piperidine 1-oxyl.

11. The method of claim 8, in which R4, independently for each of R1 and R3 comprises a hemigramicidin derivative comprising a β-turn and TEMPO.

12. The method of claim 11, in which R1 and R3, independently are chosen from XJB-5-131 and XJB-5-125.

13. The method of claim 8, in which R2 comprises a linear or branched saturated $C_4$-$C_{20}$ alkyl.

14. The method of claim 13, in which R2 has the structure:

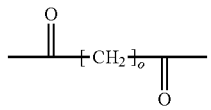

in which n is 4-18.

15. The method of claim 14, in which n is 10.

16. The method of claim 1, in which the amount effective to accelerate bone repair in the subject ranges from 0.1 to 100 mg/Kg in the subject.

17. The method of claim 16, in which the amount effective to accelerate bone repair in the subject ranges from 1 to 100 mg/Kg in the subject.

18. The method of claim 1, in which the compound is chosen from one or more of XJB-5-133, XJB-5-208, XJB-2-300, XJB-2-70, XJB-5-131, XJB-5-125, XJB-5-197, XJB-7-53, XJB-7-55, and XJB-7-75.

19. The method of claim 1, wherein the compound comprises a hemigramicidin attached to a nitroxide-containing group.

20. The method of claim 1 in which the subject has low bone density.

21. The method of claim 20, in which the subject has osteoarthritis.

22. The method of claim 1, in which the subject has not been exposed to 10 Gy or more of radiation within about 24 hours of administration of the compound.

23. The method of claim 1, wherein the compound is JP4-039 or JP4-049.

24. A method of accelerating bone healing, growth or repair in a subject, comprising administering to the subject during or after bone injury, damage or deficiency in the subject, a composition comprising an amount of a targeted nitroxide compound effective to accelerate bone repair in the subject, wherein the targeted nitroxide compound is:

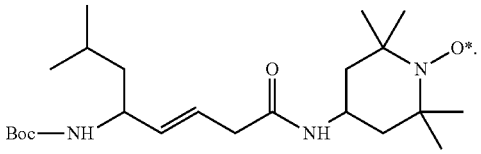

25. The method of claim 24 in which the subject has low bone density.

26. The method of claim 25, in which the patient has osteoarthritis.

27. The method of claim 26, in which the subject has not been exposed to 10 Gy or more of radiation within about 24 hours of administration of the compound.

28. A method of accelerating bone healing, growth or repair in a subject, comprising administering to the subject during or after bone injury, damage or deficiency in the subject, a composition comprising an amount of a targeted nitroxide compound effective to accelerate bone repair in the subject, wherein the targeted nitroxide compound is JP4-039.

29. The method of claim 1, wherein the subject has bone breakage or removal of bone.

30. The method of claim 1, wherein the subject has a bone disease state.

* * * * *